(12) United States Patent
Funaro et al.

(10) Patent No.: US 8,338,172 B2
(45) Date of Patent: Dec. 25, 2012

(54) METHODS FOR OBTAINING IMMORTALIZED ANTIBODY SECRETING CELLS

(75) Inventors: Ada Funaro, Turin (IT); Gianni Garotta, Lucinges (FR); Marianne Murphy, Carouge (CH)

(73) Assignee: Ribovax Biotechnologies S.A., Petit-Lancy (CH)

( * ) Notice: Subject to any disclaimer, the term of this patent is extended or adjusted under 35 U.S.C. 154(b) by 776 days.

(21) Appl. No.: 12/097,675

(22) PCT Filed: Dec. 15, 2006

(86) PCT No.: PCT/EP2006/069780
§ 371 (c)(1),
(2), (4) Date: Jan. 15, 2009

(87) PCT Pub. No.: WO2007/068758
PCT Pub. Date: Jun. 21, 2007

(65) Prior Publication Data
US 2009/0270268 A1 Oct. 29, 2009

(30) Foreign Application Priority Data
Dec. 16, 2005 (WO) ................ PCT/EP2005/056871

(51) Int. Cl.
*C12N 5/00* (2006.01)
*C12N 5/02* (2006.01)
(52) U.S. Cl. ...................... 435/346; 435/377; 435/372.2
(58) Field of Classification Search .................. None
See application file for complete search history.

(56) References Cited

U.S. PATENT DOCUMENTS

| 4,997,764 | A | 3/1991 | Dalla Favera | |
|---|---|---|---|---|
| 7,807,415 | B2 * | 10/2010 | Groen et al. | 435/70.21 |
| 2010/0021470 | A1 * | 1/2010 | Lanzavecchia | 424/141.1 |

FOREIGN PATENT DOCUMENTS

| CA | 2035381 | 8/1991 |
|---|---|---|
| EP | 1 566 442 | 8/2005 |
| WO | WO-91/04336 | 4/1991 |
| WO | WO-96/40252 | 12/1996 |
| WO | WO-02/46233 | 6/2002 |
| WO | WO-2004/076677 | 9/2004 |
| WO | WO 2004076677 | * 9/2004 |

OTHER PUBLICATIONS

International Search Report in PCT/EP2006/069780 dated Apr. 5, 2007.
Morgenthaler et al., "Human Immunoglobulin G Autoantibodies to the Thyrotropin Receptor from Epstein-Barr Virus-Transformed B Lymphocytes: Characterization by Immunoprecipitation with Recombinant Antigen and Biological Activity," Journal of Clinical Endocrinology and Metabolism, 81(9): 3155-3161 (1996).
Niedbala et al., "A Comparison of Three Methods for Production of Human Hybridomas Secreting Autoantibodies," Hybridoma, 17(3):299-304 (1998).
Steenbackers et al., "Efficient Generation of Human Anti-Cytomegalovirus IgG Monoclonal Antibodies from Preselected Antigen-Specific B Cells," Hybridomas, 4:166-173 (1993).

* cited by examiner

*Primary Examiner* — Michail Belyavskyi
(74) *Attorney, Agent, or Firm* — Marshall, Gerstein & Borun LLP

(57) ABSTRACT

The present Invention provides novel methods for immortalizing cells that secrete antibodies of one or more specific isotypes. Polyclonal, oligoclonal, and monoclonal populations of cells obtained using the methods of the Invention can be screened on the basis of the functional and/or binding activities of the antibodies they secrete, for example directed to antigens of human or viral origin having medical interest, in cell culture conditions. Using these methods, human B cells that secrete antibodies binding human Cytomegalovirus, Herpes Simplex Virus, or HSP60 protein have been efficiently immortalized with Epstein-Barr virus.

8 Claims, 15 Drawing Sheets

```
              10        20        30        40        50        60
              ....|....|....|....|....|....|....|....|....|....|....|....|
HC 9G8   MGSTAILALLLAVLQGVCAEVQLVQSGAEVKKPGESLKISCKGSGYTFDSYWIGWVRQMP
                                                          HCDR1

70        80        90       100       110       120
              ....|....|....|....|....|....|....|....|....|....|....|....|
HC 9G8   GKGLEWMGIIYPGDSDTRYSPSFQGQVTISADKSISTASLQWSSLRASDTAMYYCARHTY
                  HCDR2

130       140       150       160       170       180
              ....|....|....|....|....|....|....|....|....|....|....|....|
HC 9G8   PGPNSGYDYFEYWGQGTLVTVSSASTKGPSVFPLAPSSKSTSGGTAALGCLVKDYF
         HCDR3
```

B)

```
              10        20        30        40        50        60
              ....|....|....|....|....|....|....|....|....|....|....|....|
VL 9G8   FLLLLWLPDTTGEIVLTQSPATLSLSPGERVTLSCRASQSVYNYLAWYQQKPGQAPRLLI
                                            LCDR1

70        80        90       100       110       120
              ....|....|....|....|....|....|....|....|....|....|....|....|
VL 9G8   YDASNRATGIPARFSGSGSGTDFTLTISSLEPEDFAVYYCQLRRGTFGQGTKVEIKRTVA
            LCDR2                                 LCDR3

130       140       150
              ....|....|....|....|....|
VL 9G8   APSVFIFPPSDEQLKSGTASV
```

METHODS FOR OBTAINING IMMORTALIZED ANTIBODY SECRETING CELLS

CROSS REFERENCE TO RELATED APPLICATIONS

This is the U.S. national phase application of International Application No. PCT/EP2006/069780, filed Dec. 15, 2006, which claims the benefit of International Application No. PCT/EP2005/056871, filed Dec. 16, 2005.

TECHNICAL FIELD

The present Invention relates to methods for obtaining immortalized cells that secrete antibodies, in particular those of human origin and secreting antibodies having high specificity for antigens of medical interest.

BACKGROUND OF THE INVENTION

Antibodies are naturally occurring proteins produced by immune systems in order to fight infections and eliminate pathogenic factors. Antibodies exert their functions by binding protein or non-protein antigens and triggering a defensive response for eliminating them.

In recent years, an entire therapeutic approach (named passive immunotherapy or passive serotherapy) has been built on the antigen-binding features of antibodies directed against both human and non-human molecules. Passive immunotherapy consists of the administration of pharmaceutical compositions comprising therapeutic antibodies with a defined antigen specificity for a pathogenic molecule (a toxin, a protein, a virus, a parasite, or a cell, for example) to patients whose immune system is unable to produce them in the amounts and/or with the specificity required to block and/or eliminate the pathogen (Dunman P M and Nesin M, 2003; Keller M A and Stiehm E R, 2000).

This approach has been successfully introduced into clinical practice in the early 1980s, and since then the use of therapeutic antibodies has rapidly expanded the opportunities for the treatment of a wide variety of diseases, including infectious diseases, immune-mediated diseases and cancer, resulting in constant growth of the therapeutic monoclonal antibody sector (Chatenoud L, 2005; Pavlou A and Belsey M, 2005; Laffy E and Sodoyer R, 2005).

Therapeutic antibodies suitable for passive immunotherapy are those having homogeneous, well-defined specificity and activities. These properties can be determined most accurately and reliably for a monoclonal antibody (i.e. an antibody secreted by a single clone of antibody-secreting cells) rather than for a polyclonal antibody (i.e. a complex mixture of antibodies secreted by different clones of antibody-secreting cells).

Since the 1970s, different technologies have been developed to isolate, propagate, and maintain large sets of cell lines, each derived from a single monoclonal cell culture secreting a monoclonal antibody (mAb), to be tested, using the appropriate assays, for identifying those having the desired properties.

Two important technical issues are common to all of these methods:

a) How to provide the antibody in amounts sufficient for the functional assays that are required for identifying and characterizing the antibody before performing any in vivo experimentation;

b) How to guarantee that the therapeutic antibody is not recognized itself as an antigen by the patient's immune system, triggering the elimination of the therapeutic antibody and/or immune inflammatory reactions that may be dangerous to the patient.

The first issue is related to the difficulty in propagating and maintaining natural antibody-secreting cells in culture in enough time to have the biological material to test. This inconvenience has been solved by either immortalizing and maintaining in culture the primary antibody-secreting cells in which the nucleic acids encoding the antibodies have been initially generated and expressed, or by using recombinant DNA techniques for isolating antibody-encoding nucleic acids from these cells and transferring them into immortalized cells, in which they can be expressed and maintained.

In the past, primary antibody-secreting cells have been immortalized in cell culture conditions either by fusing them with cells already immortalized (forming hybrid cells or hybridomas that can be more easily maintained), or by using agents (such as virus) that alter the cellular machinery of primary antibody-secreting cells in a way that the cells propagate almost indefinitely.

The problem of guaranteeing the patient's safety has been solved in the past either by making use of cells and nucleic acids of human origin for producing antibodies, or by modifying the genes encoding non-human antibodies, that have an immunogenic potential, with sequence of human origin, an "humanization" process performed using recombinant DNA technologies.

In conclusion, passive immunotherapy can confer an efficient and rapid protection against infections and other pathologies. However, each method to isolate, screen, and produce monoclonal antibodies fully compatible with treatment in humans suffers from a different type of drawback, as briefly reviewed below.

The hybridoma technology, first described by Kohler and Milstein (Kohler G and Milstein C, 1975), allowed the isolation of continuously growing clones of antibody-secreting cells after being fused to an appropriate immortalized cell type. Hybridomas have been derived from human antibody-secreting cells (Olsson L and Kaplan H, 1980), but the process to produce human hybridomas has not proved to be robust, due to the lack of suitable human myeloma or lymphoblastoid fusion partners, and to the instability of human/human homohybridomas and human/murine heterohybridomas.

The humanization of murine antibodies can be achieved by grafting the antigen-binding region of the murine monoclonal antibody onto the backbone of a human antibody molecule, producing a chimeric molecule, and by substituting specific murine residues with other human amino acids to reduce antigenicity through molecular approaches (Hwang W and Foote J, 2005; Carter P, 2006).

There are numerous "humanized" antibodies currently in use or in clinical trials. However, these antibodies still contain 5-10% murine (or non-fully human) protein sequences and may elicit an immune response that limits the therapeutic efficacy of these drugs. In addition, the humanization process is labor-intensive and sometimes results in changes to antibody binding.

Therefore, this method has been mostly used with antibody-secreting cells originated in rodents immunized with the relevant antigen. Given that sequences of murine origin can be immunogenic in humans, the resulting mAbs can elicit toxic human-anti-murine responses, having an impaired antibody-dependent cellular cytotoxicity, and/or be rapidly cleared from the body. Moreover, even variable-region-identical antibodies may present different functional and immunogenic properties (Torres M et al., 2005).

Main approaches for producing fully human monoclonal antibodies are based on the cloning and the expression of human immunoglobulin genes using recombinant DNA technologies.

In a first case, libraries of DNA sequences encoding antibody fragments, including antigen-binding regions, can be amplified from human tissues and inserted into bacterial phage, allowing the "display" of antigen-binding fragments on the surface of the phage and the subsequent screening. Monoclonal antibodies against human pathogens have been produced, starting from the large antibody repertoire derived from patients that was cloned and screened using phage display technologies (Mancini N et al., 2004).

However, as employed under most circumstances, these libraries may be ineffective for identifying therapeutic antibodies since the antibody genes are not selected as the immune system does in vivo, on one side, for eliminating sequences in the human antibody repertoire that may elicit an immune response, and, on the other side, for selecting antibody sequences resulting from affinity maturation. Thus, complex in vitro affinity maturation and other technologies allowing direct sequence alterations are sometimes needed to improve antibodies from such libraries (Hoet R et al., 2005).

In a second case, transgenic mice expressing human antibody genes can be immunised with antigens of interest to produce murine cells expressing fully human antibodies (Kellermann S and Green L, 2002). This methodology has an advantage over traditional phage display methodologies because the antibodies are selected in vivo and may contain an increased frequency of high affinity antibodies. However, the mouse immune system acting in the mouse environment may not generate human antibodies with the appropriate specificity for an effective therapeutic use.

Thus, the ideal therapeutic antibody for passive immunotherapy is a human monoclonal antibody that is derived from human immune cells that have matured in a human being. However, the selection and the production of such antibodies is a complex and time-consuming process since conventional methods for producing and isolating populations of viable, immortalized human cells that secrete antibodies in cell culture conditions are inefficient.

The development and proliferation processes of human B cells, leading to their antigen specificity and long-term responses in vivo, and means to study the process in vitro using cells obtained from the immune system have been extensively reviewed (Banchereau J and Rousset, F, 1992; Crotty S and Ahmed R, 2004; Carsetti R, 2004; McHeyzer-Williams L and McHeyzer-Williams M, 2005). However, the isolation of human B cells expressing mAbs of interest has been hampered by the technical inability to produce stable human antibody-secreting cell lines, even when relevant binding or neutralizing activities can be detected.

Many different populations of antibody-secreting cells can be isolated from human donors having specific profiles (e.g. naive, vaccinated, more or less recently infected and seropositive individuals) and from different tissues (e.g. blood, tonsils, spleen, lymph nodes) where B cells reside and exert their activities (Viau M and Zouali M, 2005).

The identification of human monoclonal antibodies requires the extensive screening of the populations of immortalized B cells, wherein each cell secretes a specific monoclonal antibody in sufficient amounts for its characterization in cell culture conditions (Cole S et al., 1984; James K and Bell G, 1987; Borrebaeck C, 1989). However, the technologies for the selection, activation, and immortalization of antibody-secreting cells are still suffering from technical problems (yield of antibody, immortalization efficiency, overrepresentation of certain isotypes, cell stability and growth), leading to an insufficient number of cells and secreted antibodies available for screening assays.

Given the difficulty in obtaining stable hybridomas from human antibody-secreting cells, one method that has been extensively used to produce and isolate human antibody-secreting cells is the immortalization of human B cells with Epstein Barr Virus (EBV), which is also known to induce polyclonal B cell activation and proliferation (Sugimoto M et al., 2004; Bishop G and Busch L K, 2002).

Antibody-secreting cells have been produced by EBV immortalization using different sources of human B cells such as the peripheral blood of healthy subjects preselected using a labelled antigen (Casali P et al. 1986), lymph nodes, spleen, or peripheral blood from patients (Yamaguchi H et al., 1987; Posner M et al., 1991; Raff H et al., 1988; Steenbakkers P et al., 1993; Steenbakkers P et al., 1994), tonsils (Evans L et al., 1988), or pleural fluids (Wallis R et al., 1989).

However, because of low transformability, low clonability, and the inherent instability and heterogeneity of EBV-infected human B cells, valuable antibody-secreting B cells are often lost during this procedure (Chan M et al., 1986; James K and Bell G, 1987), obliging an additional cell fusion procedure to be applied after EBV infection (Bron D et al., 1984; Yamaguchi H et al., 1987; Posner M et al., 1991). In fact, some authors concluded that the best method for producing stable, human IgG antibody-secreting human monoclonal cell cultures was based on the fusion of human lymphocytes with a myeloma cell line (Niedbala W and Stott D, 1998; Li J et al., 2006), despite the technical difficulties with human hybridomas discussed above.

Various attempts have been directed at improving the immortalization process, for example by combining different approaches (immortalization with oncogenic virus, transformation with oncogenes, mini-electrofusion, mouse-human heterofusion) in a single process (U.S. Pat. No. 4,997,764; Steenbakkers P et al., 1993; Dessain S K et al., 2004). Human monoclonal antibodies have been isolated from B cells that have been activated and immortalized (in the presence or in the absence of an antigen), and by combining various manipulations in cell culture (Borrebaeck C et al., 1988; Davenport C et al., 1992; Laroche-Traineau J et al., 1994; Morgenthaler N et al., 1996; Niedbala W and Kurpisz M, 1993; Mulder A et al., 1993; WO 91/09115; Hur D et al., 2005; Traggiai E et al., 2004; Tsuchiyama L et al., 1997; WO 04/076677; WO 88/01642; WO 90/02795; WO 96/40252; WO 02/46233).

In general, the literature on methods for isolating and immortalizing cells that secrete antibodies, especially of human origin, does not provide a clear understanding on how to design the whole process for obtaining the largest repertoire of immortalized antibody-secreting cells, starting from the purification of cells that express antibodies from biological samples up to the screening of the antibodies that are secreted in cell culture conditions.

It would be clearly advantageous to provide methods for establishing more optimized processes in which, by applying specific means and conditions in cell culture for improving selection and viability of the antibody-secreting cells in an antigen-independent manner (but having specific isotypes of interest), a high throughput analysis of the secreted antibodies can be performed on the largest possible population of immortalized antibody-secreting cells maintained in cell culture conditions. Such a process would also expedite methods making use of molecular approaches to clone antibody genes because the population of B cells from which the antibodies having an isotype of interest are cloned may be repeatedly analyzed for the detection of cells secreting antibodies with a desired activity and stored in a viable state for future analysis.

DISCLOSURE OF THE INVENTION

The present Invention is based on the observation that conditions and means for selecting, stimulating, and immortalizing antibody-secreting cells have not been chosen and combined in an effective manner in the literature to improve the cell viability in culture conditions and their sensitivity to immortalizing agents.

In fact, it was surprisingly found that specific combinations of such conditions and means not only improve cell immortalization but considerably enhance the throughput and the reproducibility of the whole process for generating, in an antigen-independent manner, populations of immortalized cells that secrete antibodies of specific isotypes in high amounts and that can be stored in a viable state.

The methods of the Invention actually provides polyclonal populations of cells that can be used and maintained as libraries of antibody-secreting, isotype-specific cells. Using this approach, specific oligoclonal or monoclonal populations of cells that secrete, in cell culture conditions, antibodies having different functional and/or binding activities can be detected and isolated at any desired moment (FIG. 1).

The present Invention provides a method for immortalizing a population of cells that secrete antibodies of one or more specific isotypes comprising the following steps:

a) Selecting the population of cells that secrete antibodies from one or more biological samples in an antigen-independent manner and on the basis of the expression of at least a cell surface marker;

b) Stimulating said population of selected cells with at least a stimulating agent in cell culture conditions;

c) Eliminating said stimulating agent from the cell culture;

d) Selecting the population of stimulated cells that expresses antibodies of said specific isotypes from said cell culture;

e) Exposing said population of selected and stimulated cells to the immortalizing agent in cell culture conditions f) Eliminating said immortalizing agent from said cell culture;

Wherein the immortalizing agent is a viral immortalizing agent.

In addition, the following steps may be performed after step (f):

g) Maintaining the population of cells obtained from said cell culture in cell culture conditions;

h) Determining the number, the viability, and/or the proliferation activity of the population of cells that secrete antibodies of said specific isotypes in said cell culture.

This schematic process can be integrated and adapted by applying additional conditions and means relating to:

The identification of donors or biological samples from which the cells can be isolated;

The specific means for selecting, stimulating, and/or immortalizing antibody-secreting cells;

The cell culture conditions that allow the maintenance, the growth, and the proliferation of the population of immortalized antibody-secreting cells in cell culture conditions;

The means for determining the number, the viability and/or the proliferation activity of the population of cells that secrete antibodies of said specific isotypes in said cell culture;

The desired properties of the antibody and the related assays that are chosen for screening the immortalized antibody-secreting cells.

The methods of the Invention provide means and conditions for optimizing the selection, stimulation, immortalization, and cloning of antibody-secreting cells at the scope of obtaining the largest diversity and number of such cells that can be maintained as a population of immortalized cells in cell culture conditions. In fact, the resulting population of cells can be considered as a library of immortalized cells that secrete antibodies and that can be subjected to the desired screening assay(s) immediately after its production according to the methods of the Invention, or, in part or totally, frozen and used later in one or more screening assays.

The population of cells obtained by the methods of the Invention can be divided into multiple oligoclonal or monoclonal population of cells that secrete antibodies in cell culture conditions, and in particular that secrete monoclonal antibodies with a desired antigen specificity and/or biological activity. In fact, the supernatant of these cell cultures is used for detecting the culture(s) containing the antibodies having such antigen specificity and/or biological activity. Such antigen-binding specificity and/or biological activity can be directed to any human, mammalian, viral, bacterial, plant, parasite, organic, or inorganic antigen of interest.

The successful isolation of such population of cells depends on the growth of such cells, the assay used to screen them, and the frequency of antigen-specific B cells in starting material (generally, peripheral blood from a donor or a pool of donors). In fact, the immortalized antibody-secreting cells should be cultured under conditions that allow for maximal cell proliferation and immunoglobulin secretion, as well as the direct use of cell culture supernatants for detecting the desired activity. If needed, the population of cells may be further divided for screening the pools of cells showing the desired antigen specificity and/or biological activity, until one or more cell cultures, each of them secreting a monoclonal antibody having the desired antigen specificity and/or biological activity in the cell supernatant, is isolated.

A monoclonal antibody with a desired antigen specificity and/or biological activity can be therefore produced by expanding the cell culture, and purifying the monoclonal antibody from the supernatants of this cell culture. Additionally, the DNA encoding the monoclonal antibody can be then isolated and used for the recombinant expression of the antibody in host cells.

Further objects of the present Invention are populations of immortalized antibody-secreting cells maintained in cell culture conditions (in particular polyclonal, oligoclonal and monoclonal cell cultures of antibody-secreting cells) obtained by the methods of the Invention that can be used for identifying and producing monoclonal antibodies having the desired antigen specificity and/or biological activity. The antibodies can be directly purified from the cell cultures or produced as recombinant proteins using the DNA sequences encoding them and isolated from the specific cell culture. In addition, DNA libraries comprising DNA sequences that encode antibody sequences of one or more specific isotypes, can be prepared using nucleic acids isolated from a population of cells of the Invention, in particular from a population of cells that has been shown to secrete antibodies having any kind of binding and/or biological activity of interest.

Other objects of the present Invention are related to the use of the population of cells, of the cell cultures, of the cell culture supernatants, and of the DNA libraries obtained by the methods of the Invention from antibody-secreting cells for identifying and producing monoclonal antibodies. These products obtained by the methods of the Invention can also be included in kits for identifying and producing a monoclonal antibody having the desired antigen-binding specificity and/or biological activity, or used for determining the features of the isotype-specific, immune response to an autologous or heterologous antigen, a virus, a bacterial cell, a toxin, a parasite cell, or a vaccine in an individual (or in population of individuals).

The populations of cells and the cell cultures obtained by the methods of the Invention can be included in methods for producing cell cultures that secrete monoclonal antibodies in the cell culture supernatant, and that can be expanded at the scope of purifying monoclonal antibodies.

The Examples provide means and conditions for applying the methods of the Invention at the scope of generating EBV-immortalized populations of human B cells for obtaining, from the same biological sample, monoclonal or oligoclonal populations of cells expressing antigen- or virus-specific human IgG antibodies.

DESCRIPTION OF FIGURES

FIG. 15: Protein sequence of variable regions in the heavy chain (A; VH; SEQ ID NO: 3) and light chain (B; VL; SEQ ID NO: 8) for the antibody secreted by the cells in well 9G8 (see FIG. 14). The CDR sequences for the heavy (HCDR1, SEQ ID NO: 4; HDCR2, SEQ ID NO: 5; HCDR3, SEQ ID NO: 6) and light (LCDR1, SEQ ID NO: 9; LDCR2, SEQ ID NO: 10; LCDR3, SEQ ID NO: 11) chain are predicted on the basis of different methodologies comparing known antibody sequences, such as the V-Quest, provided by IMGT (Giudicelli V. et al., 2004; available at http colon-slash-slash imgt-.cines.fr/IMGT_vquest/share/textes/index.html) and are underlined. Ten thousand cells from this cell culture were used for determining the two sequences using standard protocols. Cells were pelleted and mRNA was extracted in order to produce the cDNA by 5' RACE amplification using degenerate VH and VL primers. The sequences were then cloned in plasmids used for transforming bacterial cells. The consensus DNA sequences encoding of variable regions in the heavy chain (SEQ ID NO: 2) and light chain (SEQ ID NO: 7) were determined using the sequences from at least 4 independent bacterial cell clones.

DETAILED DESCRIPTION OF THE INVENTION

Figure 1:
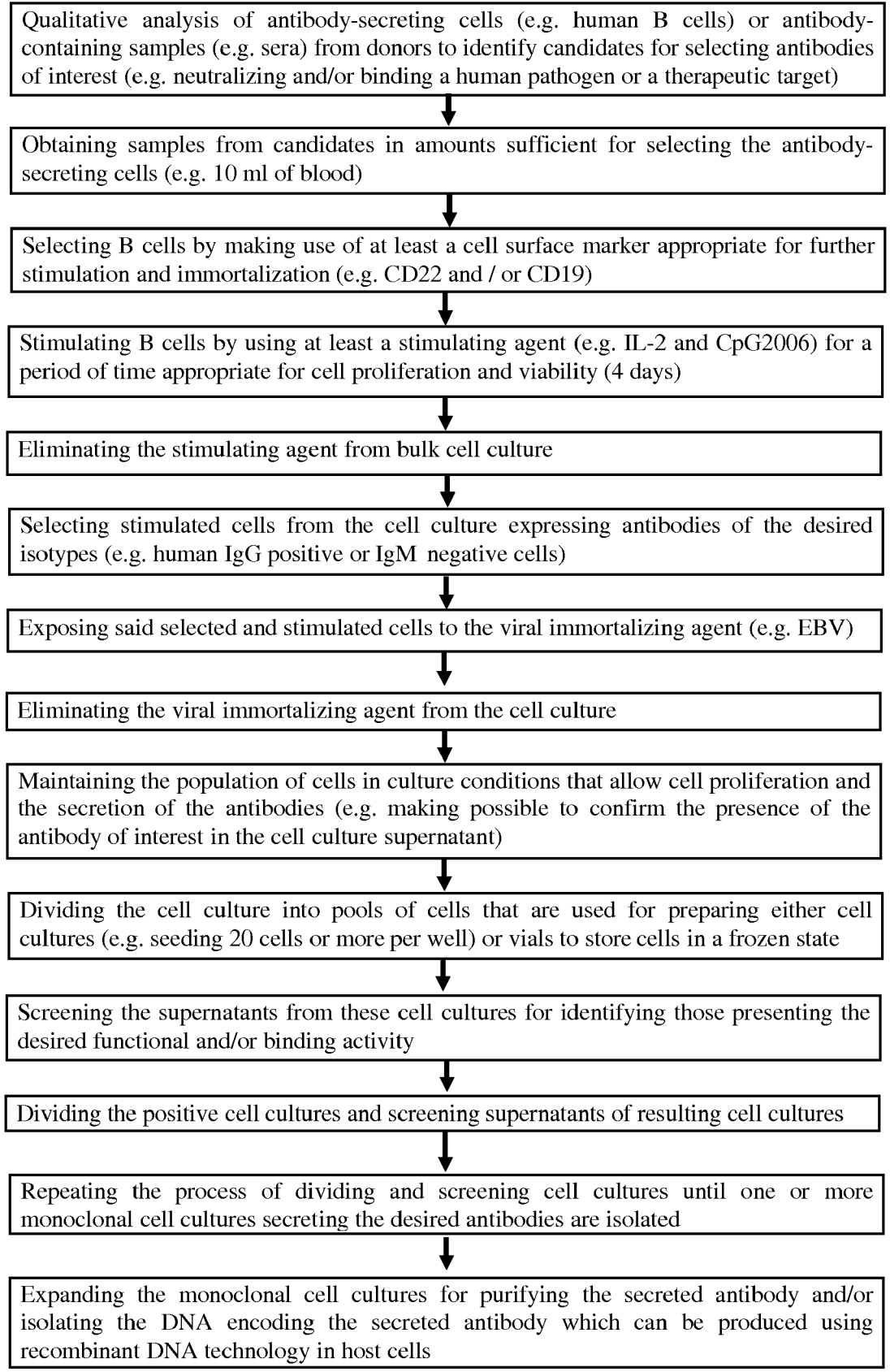
FIG. 1: Schematic representation of a process for isolating and expressing monoclonal antibodies including the methods of the Invention for obtaining immortalized antibody-secreting cells.

The present Invention provides methods for improving the efficiency by which immortalized antibody-secreting cells can be produced and screened on the basis of the antigen specificity and/or biological activity of the secreted antibodies.

In particular, the Examples show how the proliferating activity, viability and antibody secretion of human B cells in cell culture conditions that are immortalized using Epstein-Barr virus can be improved by applying appropriate combinations of means and conditions on primary cells isolated from donors.

It has been found that the choice of specific means and conditions related to cell selection and stimulation has unexpected and important enhancing effects for obtaining viable and proliferating antibody-secreting cells, contributing to a larger diversity and number of immortalized antibody-secreting cells that can be later screened directly using the cell culture supernatants.

The Examples also show that the initial selection of the cells from the biological samples can be based on one or more cell surface markers, followed by a stimulation phase in which cells are exposed to one or more stimulating agents. However, the stimulating agents exert their maximal activity, without affecting cell viability and proliferation, only if applied, at defined concentration ratios, on specifically selected populations of cells for an appropriate period of time. Moreover, a clear temporal and physical distinction between the stimulation and immortalization steps should be made, being evident the negative effects of simultaneously exposing the cells to the stimulating and the immortalizing agents.

In particular, the Examples show how these elements can be combined to establish efficient and reproducible methods for the EBV immortalization of human IgM negative (or IgG positive) B cells that can be subsequently cloned and screened, using their cell culture supernatants and according to the binding and/or functional features of the antibodies they produce (such as neutralizing cytomegalovirus infection on human cells) and, finally, that can then be isolated and cloned for further characterization and production of the antibodies as recombinant proteins.

Sequential approaches involving separate steps of cell selection and activation before immortalization have been disclosed in the literature only in connection to antigen-specific populations of cells that were previously in vitro immunized, often using fusion with myeloma cells in addition to (or instead of) a viral immortalizing agent.

Thus, the initial populations of B cells were either depleted of specific cell types using a cytotoxic agent and then exposed to the antigen combined with cytokines and growth factors (Borrebaeck C et al., 1988; Davenport C et al., 1992; Laroche-Traineau J et al., 1994) or exposed to an antigen-specific panning procedure, and then expanded over a feeder cell layer before being selected (Steenbakkers P et al., 1993; Steenbakkers P et al., 1994).

Populations of antibody-secreting cells have been immortalized either using a standard EBV immortalization, or using combined EBV- and oncogene-mediated transformation (U.S. Pat. No. 4,997,764), EBV immortalization or non-specific cell activation followed by the fusion with a myeloma cell line (Niedbala W and Stott D, 1998; WO 02/46233), selection of cells expressing antibodies having a specific isotype after EBV immortalization (Morgenthaler N et al., 1996), or selection of cells followed by the use of EBV immortalization in the presence of a B cell activating agent (WO 91/09115; Hur D et al., 2005; Traggiai E et al., 2004; Tsuchiyama L et al., 1997; WO 04/076677).

However, none of these documents provide an effective process associating the means and conditions for obtaining cell selection and activation before immortalization and the efficiency of a viral immortalization process that provides, in particular, polyclonal populations of cells that can be extensively and directly used for identifying oligoclonal or monoclonal populations of cells expressing antibodies having the desired isotype and biological activity.

The main object of the present Invention consists in a method for immortalizing a population of cells that secrete antibodies of one or more specific isotypes comprising the following steps:

a) Selecting the population of cells that expresses antibodies from one or more biological samples in an antigen-independent manner and on the basis of the expression of at least a cell surface marker;
b) Stimulating said population of selected cells with at least a stimulating agent in cell culture conditions;
c) Eliminating said stimulating agent from the cell culture;
d) Selecting the population of stimulated cells that expresses antibodies of one or more isotypes from said cell culture;
e) Exposing said population of selected and stimulated cells to the immortalizing agent in cell culture conditions;
f) Eliminating said immortalizing agent from said cell culture;

Wherein the immortalizing agent is a viral immortalizing agent.

This method can be integrated with a series of additional steps that are related to the analysis and the use of the population of cells that is obtained by applying this method (FIG. 1). In particular, the following two steps should be performed after step (f) since they are important for establishing cell cultures comprising this population of cells:

g) Maintaining the population of cells obtained from said cell culture in cell culture conditions;
h) Determining the number, the viability, and/or the proliferation activity of the population of cells that secrete antibodies of said specific isotypes in said cell culture.

The text and the figures provide further details on how the methods of the Invention can be applied, in particular on human B cells isolated from peripheral blood samples, to provide monoclonal cell cultures secreting antibodies of interest.

In fact, the methods of the Invention allow obtaining, on one hand, populations of cells that efficiently represent, in an antigen-independent manner, the heterogeneity of the antibody repertoire of the desired isotypes expressed in the primary cells taken from the individuals and captured through the viral immortalization.

On the other end, the more uniformly viable and highly proliferating populations of immortalized antibody-secreting cells that are obtained by the methods of the Invention, allows a deeper analysis of such antibody repertoire by means of different biological products that can be obtained either in cell culture conditions (e.g. population of cells, cell culture supernatants containing high amounts of antibodies) or as other molecular entities (e.g. DNA libraries prepared using nucleic acids extracted from oligoclonal populations of cells).

Moreover, the methods of the Invention provide the possibility to obtain enough antibodies and immortalized cells that secrete antibodies to be characterized directly in the cell cultures generated by dividing the polyclonal population of immortalized antibody-secreting cells (freshly prepared or previously prepared, frozen, and thawed) in pools statistically containing 20 or less cells and grown in standardized conditions. The lower number of cloning steps (virtually a single one, rather than the usual two or more steps) shortens the time for identifying immortalized cells that secrete antibodies of interest, limiting the risk of losing them in subcloning steps and speeding up the characterization of antibodies in different in vivo or in vitro assays. This is of particular importance for the isolation of rare antibodies specific for therapeutic targets that can be more rapidly and successfully accomplished.

Figure 11:
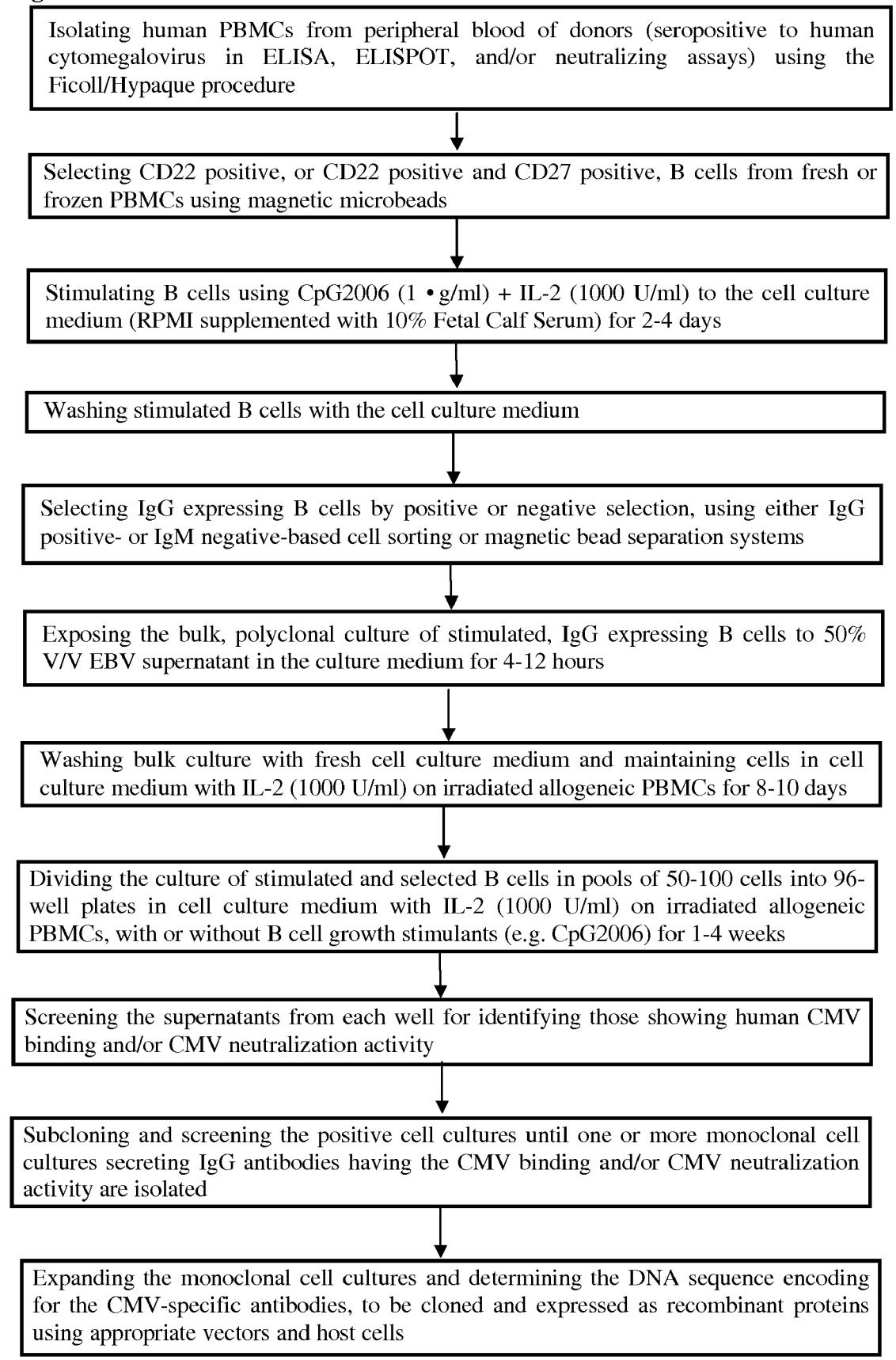
FIG. 11: Schematic representation of a general process for identifying human B cells secreting IgG antibodies that bind and/or neutralize human cytomegalovirus (CMV) comprising the methods of the Invention for immortalizing antibody-secreting cells, such as human B cells.
Figure 13:
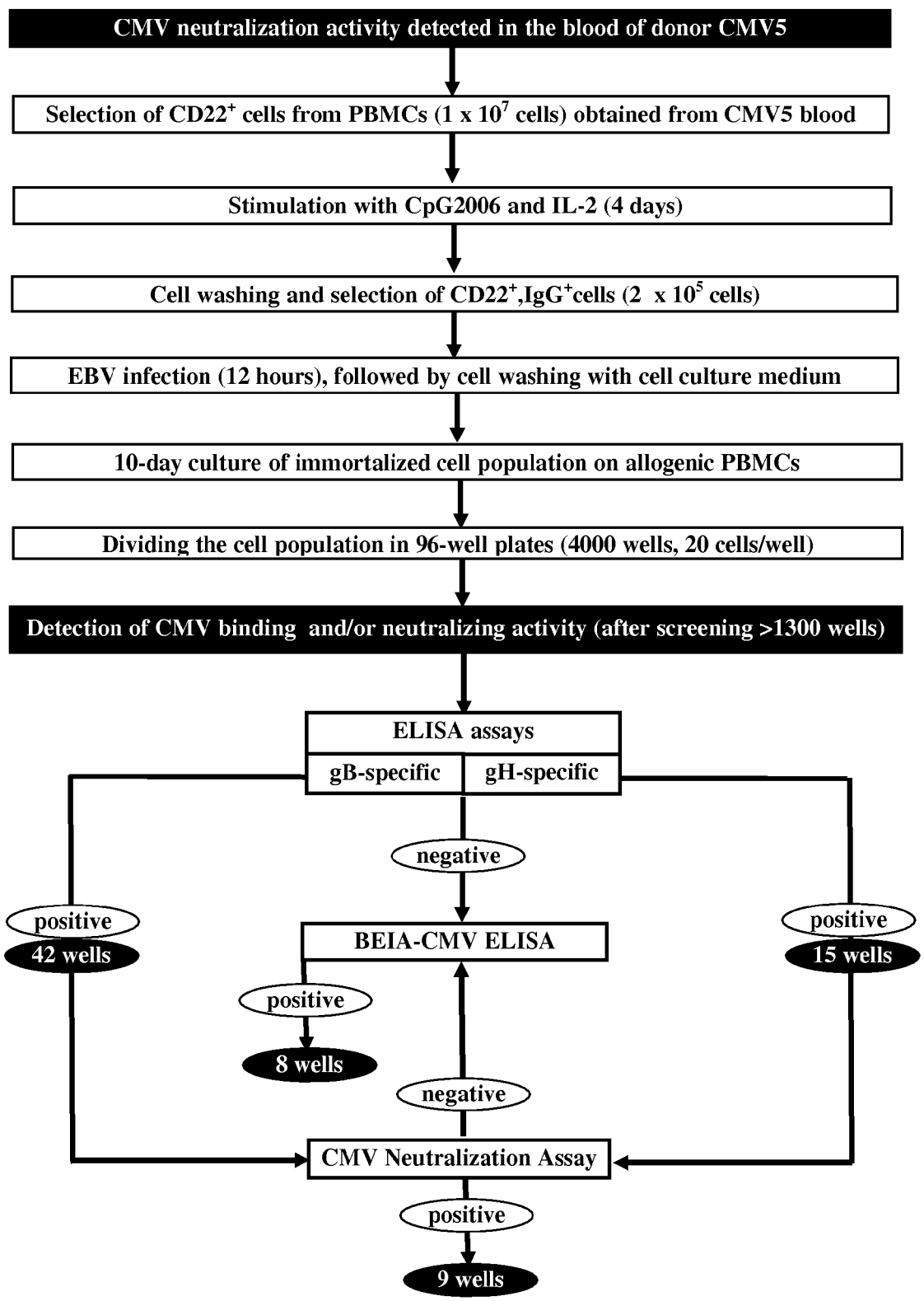
FIG. 13: Overview of the procedure for preparing the populations of immortalized antibody-secreting cells according to the methods of the Invention starting from the blood of a human donor showing CMV neutralizing activity. Oligoclonal and monoclonal populations of immortalized cells have been identified according to the properties of the antibodies identified in the cell culture supernatants: secreting antibodies that bind total CMV protein extract (as tested using a kit, BEIA-CMV ELISA), that bind specific antigens (tested using fragments of the CMV proteins gB and gH), and/or that neutralize CMV infection in an in vitro assay.

Therefore, the methods of the Invention can be adapted and integrated in more complex methods for identifying and producing monoclonal antibodies of specific isotypes that are summarized in the text (see in particular in Example 3), and in the figures (see in particular FIGS. 1, 11, and 13).

Definitions and further details on the means and the conditions applicable to the methods of the Invention are provided in the following paragraphs, together with the description of the possible uses of the said methods and of the products that can be obtained using said methods (populations of cells, cultures of cells, supernatants of the cell culture, and antibodies, in particular human monoclonal antibodies).

The term "population" of cells refers in general to any group of cells (antibody-secreting cells, in the present case) that are isolated using the same criteria or generated using the same methods. For instance, populations of cells are those resulting from a selection step (e.g. cell sorting), a treatment (e.g. with stimulating or viral immortalizing agents), or the division of a culture or a population of cells into smaller pools of cells having statistically the same amount of cells (e.g. when subcloning a cell culture or preparing vials of immortalized cells to be frozen for long-term maintenance). A population of cells should be viable but not necessarily exerting a specific biological activity (e.g. growing, proliferating, or secreting antibodies), as it happens in cell culture conditions.

The term "culture" of cells refers to a population of cells that is maintained in a container (e.g. the well of a plate, a Petri dish, a flask, a bottle) at the scope of making the cells perform biological activities (e.g. growing, proliferating, or secreting antibodies), and/or of treating them with specific compounds (e.g. stimulating or viral immortalizing agents). These experimental conditions (that is, cell culture conditions) include the use of incubators maintained at a temperature and in an atmosphere (together with the use of cell culture medium) appropriately chosen for the growth and the proliferation of the cells.

A cell culture is therefore composed of the population of cells together with the cell culture medium (comprising sera, growth factors, cytokine, nutrients, etc.) and, as in the case of antibody-secreting cells, of additional cells that are also cultured for supporting the growth and the proliferation of the population of cells (the so-called "feeder cells"). After a few days or weeks, the composition of cell culture medium is altered not only by the consumption of the cells but also by the large variety of molecules that cells secrete, or simply release when they enter into apoptosis or die. Thus, the cell culture medium is regularly substituted with a new one, or it can be partially removed to analyze the content of the cell culture medium. The used cell culture medium (defined in the literature as "supernatant" of the cell culture, as well as "spent" or "conditioned" cell culture medium) can be collected at fixed time points to determine, for example, the content and the activity of the antibodies that have been secreted by the population of cells in cell culture conditions. This information, together with the data on the viability and the proliferation of such cells, should be used to define the status and the possible use of the cell culture (e.g. for isolating mRNA, in screening assays, for purifying monoclonal antibodies, for collecting cells to be frozen, etc.)

The term "polyclonal" refers to a culture or a population of cells that express a high number of different antibodies (e.g. $10^3$, $10^4$, $10^5$ or more) each of them expressed by a single or group of cells within the culture or the population. In particular it applies to a culture or a population of cells obtained by the methods of the Invention (since generated in an antigen-independent manner from cells present in a biological sample) that is not divided in cultures or populations, or, at most, divided in cultures or populations initially of 50 or more cells (e.g. 200, 500, 1000 or more cells) as it can be statistically determined on the basis of the dilution of the original polyclonal culture or population.

The term "oligoclonal" refers to a culture or a population of cells resulting from the division of a culture or population of cells into cultures or populations initially containing less than 50 cells (40, 20, 10, 5, 1, or less than 1 cell), as it can be statistically determined on the basis of the dilution of the original culture or population.

Oligoclonal cultures or populations of cells that result from the division of a culture or population of cells into cultures or populations initially containing 20 cells or less are of particular importance. In fact, if a single, or a largely predominant, biological feature is detected in the resulting cell culture (e.g. an antibody identified as a protein secreted in the cell culture supernatant using a biological assay or as a transcribed gene in the mRNA isolated from the culture using RT-PCR), such cell culture can be considered as a monoclonal cell culture.

A "monoclonal cell culture" is a cell culture comprising only (or a large majority of) cells identical to each other, being originated by the proliferation (and optionally differentiation) of a single cell (clone), at least as it can be evaluated on the basis of a specific biological feature (e.g. secretion of a specific antibody) that has been used for selecting the cell culture. Thus an antibody, a population of cells, or a cell culture derived from such a culture can be indicated as being "monoclonal" even though further experimental activities may be needed for establishing the clonality in a more precise manner.

The term "immortalized" refers in general to the cultures and populations of cells obtained from the methods of the Invention, after exposing the selected and stimulated population of cells to the viral immortalizing agent. Even though the viral immortalization can be associated with the presence of specific viral products (e.g. proteins, transcripts), the cells are defined as immortalized when they show continuous growth and proliferation in cell culture conditions. As shown in Examples, primary human B cells that are obtained from a biological sample and express antibodies, were successfully used to obtain polyclonal populations of cells that were then used to generate oligoclonal cell cultures containing at least $10^4$ cells. When the culture is started from 100, 50, 20 or even 5 cells, such a total number of cells is compatible only with a number of cell divisions (10 or more cell divisions) that in general only immortalized cells can perform in cell culture conditions.

The term "antibody-secreting cells" refers to primary cells that contain the genes for expressing antibodies and that have the capability to secrete them in the extracellular space (e.g. in the blood in vivo or in the cell culture supernatant in vitro).

The term "immortalized antibody-secreting cells" refers to antibody-secreting cells that, following exposure to a viral immortalizing agent, grow, proliferate, and secrete antibodies in cell culture conditions indefinitely, or at least for a period of time and/or for a number of cell divisions largely superior to that observed if the primary cells are not exposed to the viral immortalizing agent. In particular, the polyclonal populations of cells obtained by the methods of the Invention are enriched in viable, growing lymphoblasts that are the immortalized antibody-secreting cells which will then form the oligoclonal and monoclonal populations of cells in cell culture conditions.

The term "stimulating agent" refers to a compound, or a specific combination of compounds, capable of producing a stimulation response mediated by antibody-secreting cells, inducing a proliferating and blastic state of these cells and forming lymphoblasts (large viable cells, as measured by microscopy and by forward/orthogonal scatter on FACS) in cell culture conditions.

The term "stimulation phase" refers to the period of time during which the selected antibody-secreting cells are exposed to the stimulating agent.

The term "viral immortalizing agent" refers to any kind of viral particle, DNA, or protein, which allows generating immortalized cells from primary cells isolated from biological samples. In the present case, the primary cells are antibody-secreting cells, in particular human B cells, for which different viral immortalizing agents have been identified.

The term "immortalization phase" refers to the period of time during which the selected and stimulated antibody-secreting cells are exposed to the viral immortalizing agent.

A step preliminary to performing the methods of the Invention is the identification of individuals or tissues from which biological samples containing antibody-secreting cells should be isolated.

As indicated in the Background of the Invention, cells that express and secrete antibodies have been isolated and immortalized from different tissues and organs, including blood, tonsils, spleen, biological fluids (such as cerebrospinal or pleural fluids), lymph nodes, and other lymphatic organs.

Cells that can be immortalized using the methods of the Invention should be extracted from these mammalian tissues and organs. Obviously, cells of human origin are preferred for producing cell cultures secreting human monoclonal antibodies having therapeutic or diagnostic use. Nonetheless, the methods may be applied on non-human, antibody-secreting cells (cells of rodent or simian origin, for example).

Many different types of populations of primary antibody-secreting cells can be isolated from human donors having profiles that can be preferable according to the state of the immune cell donor, as well as the isotype and the activity of the antibody that is sought.

The methods of the Invention can be applied for the identification of monoclonal antibodies expressed by human B cells selected from donors, such as patients exposed to an infective agent or having specific forms of cancer or autoimmune disease. Thus, the donor can be naive, vaccinated, affected by one or more diseases or infections, already exposed and/or resistant to specific therapeutic treatments, presenting a specific clinical index or status, inadvertently exposed to a pathogen, etc.

Donor's sera can be used as such for an initial determination of their seropositivity to an antigen, since the specificity and long-term maintenance of the adaptive immune responses (even years after the last exposure to this antigen) may allow a qualitative determination that is sufficient for selecting donors. The nature and sensitivity of the screening assay used is critical in identifying the most suitable donor and, preferably, the assay used to screen donor serum should be the same as that used to screen supernatants from immortalized antibody-secreting B cells and designed to detect an antibody with the desired functional activity (i.e. prevention of viral entry into cells, or binding to a tumor-associated antigen)

In the clinical context, the choice of the tissue or the organ from which the cells are purified can be dictated from the availability of the cells in sufficient amount for performing the whole process. Given that cells may be obtained from human clinical samples in small quantities and/or prepared in locations different from where the immortalization methods may be performed, the cells can be obtained from frozen samples and/or from samples obtained from a number of individuals that have been pooled to provide enough starting material.

Thus, a preliminary screen can be done on a panel of candidate donors, using samples containing antibody-secreting cells (such as total peripheral blood or serum). In particular, mononuclear cells can be isolated from blood or lymphatic tissues using standard separation techniques for isolating peripheral blood mononuclear cells (PBMCs), such as gradient centrifugation. After and/or before this separation step, the samples of sera (or plasma), cell culture supernatants, or cells (obtained from different patients, from different tissues, and/or at different time points) can be pre-screened using standard technologies for detecting the presence of antibodies and antibody-secreting cells (e.g. ELISA, BIACORE, Western blot, FACS, SERPA, antigen arrays, neutralization of viral infection in a cell culture system, or ELISPOT assays).

The literature provides several Examples of these technologies showing, for example, the use of ELISPOT for characterizing the immune response in vaccinated donors (Crotty S et al., 2004), the use of antigen microarrays as diagnostic tools for newly infected patients (Mezzasoma L et al., 2002), and other technologies for measuring antigen-specific immune responses (Kern F et al., 2005). The choice of the donors may also be based on the association of the seropositivity for specific virus with oncogenesis-related alterations (Butel J, 2000).

This preliminary qualitative analysis of antibody response to the therapeutic target (evaluated at the level of the total or of the isotype-specific activity) should allow the identification of the donors having B cells expressing higher antibody titers directed to the desired purified antigen (e.g. a specific human recombinant protein related to a cancer or a specific viral protein), a mixture of related antigens (e.g. obtained from partially purified viral preparation), or a bioassay (e.g. neutralization of viral infectivity).

Once one or more donors are selected, the source of B cells can be spleen, blood, lymph nodes, bone marrow, tumor infiltrating lymphocytes, lymphocytes from sites of chronic infection/inflammation. However, peripheral blood is usually easier to obtain from donors, to store, and to monitor for the serological response against an antigen over a defined period of time.

For example, starting from 5-50 ml of peripheral blood, approximately 10-100 million of PBMCs (peripheral blood mononuclear cells) can be purified, a number of cells that should allow obtaining a sufficiently large population of antibody-secreting cells to be screened after being immortalized using the methods of the Invention.

After the isolation of PBMCs from the biological samples, a specific selection of antibody-secreting cells can be performed, using one of the many methods described in the literature, on the basis of the expression of cell surface markers on their surface and, if appropriate, of other proteins, as well as the proliferation activity, the metabolic and/or morphological status of the cells.

In particular, various technologies for the purification of antibody-secreting cells from human samples make use of different means and conditions for positive or negative selection. These cells are more easily and efficiently selected by physically separating those expressing cell surface markers specific for cells that express and secrete antibodies (e.g. human B cells). Specific protocols can be found in the literature (see Callard R and Kotowicz K "Human B-cell responses to cytokines" in Cytokine Cell Biology: A practical Approach. Balkwill F. (ed.) Oxford University Press, 2000, pg. 17-31).

The selection is usually performed using antibodies that bind specifically to one of these cell surface proteins and that can be linked to solid supports (e.g. microbeads or plastic plates) or labeled with a fluorochrome that can be detected using fluorescence-activated cell sorters (FACS). For example, human B cells have been selected on the basis of their affinity for supports (such as microbeads) binding CD19, CD27, and/or CD22 microbeads, or for the lack of binding affinity for antibodies specific for certain isotypes prior to EBV immortalization (Li H et al., 1995, Bernasconi N et al., 2003; Traggiai E et al., 2004).

However, the choice of the cell marker may be relevant for the efficiency of the immortalization process, probably due to intracellular signals that are triggered by the selection process and that may alter cell growth and viability. In fact, the Examples of the present patent application show that CD22, which is a B-cell restricted transmembrane protein that controls signal transduction pathways related to antigen recognition and B cell activation (Nitschke L, 2005), appears as a preferred molecule for the initial B cell selection. Since the CD22 positive population contains cells that express antibodies having different isotypes and specificities, other cell surface markers can be used for selecting the cells, either before or after the stimulation phase.

Alternatively or additionally, a specific enrichment of antibody-secreting cells can be obtained by applying a CD27-based selection in addition to the CD22-based selection. CD27 is known to be a marker for human B cells that have somatically mutated variable region genes (Borst J et al., 2005). Additional markers such as CD5, CD24, CD25, CD86, CD38, CD45, CD70, or CD69 could be used to either deplete or enrich for the desired population of cells. Thus, depending on the donor's history of exposure to the antigen (e.g. viral, bacterial, parasite), the antibody titer, a decision can be taken as to whether to use total, CD22 enriched B cells, or further enriched B cell subpopulations such as CD27 positive B cells.

Following cell selection, but before the immortalization phase, the population of cells should be exposed to an appropriate stimulating agent. In the context of the present Invention, three major categories of compounds are envisaged as applicable stimulating agents that can be used, especially in combination.

A first group of stimulating agents is represented by an activator of the innate immune response, such as an agonist of a Toll-Like Receptor which is expressed on B cells. The Toll-like receptors (TLR) are known to play an important role in the recognition of bacterial oligonucleotides and other compounds eliciting polyclonal activation of a wide variety of cells involved in both innate and acquired immunity (Akira S and Takeda K, 2004; Peng S, 2005). This pathway of innate immune responses mediated in part by the Toll Receptors is one of the earliest responses by the body to invading organisms and plays an important role in creating the appropriate environment and cytokine milieu required to elicit the potent and specific response mediated by the B and T cells of the adaptive immune response (Gay et al., 2006). This responsiveness of human cell lines and primary cells is due to some Toll-like receptors (TLR2, TLR4, TLR6, TLR7, TLR8, TLR9, TLR10), each having specific expression profiles, preferred ligands and recognition requirements.

In particular human TLR9 recognizes oligonucleotides, more specifically CpG-based oligonucleotides (Hemmi H et al., 2000). TLR9-mediated activation by CpG-based compounds such as the one known as CpG2006 triggers alterations in cellular redox balance and the induction of cell signaling pathways including the mitogen activated protein kinases (MAPKs) and NF kappa B, followed by the production of proinflammatory cytokines, interferons, and chemokines. (Takeshita F et al., 2001; Hartmann G et al., 2000; Hartmann G and Krieg A, 2000; Ulevitch R, 2004). Human naive and memory B-cell subsets have specific proliferation and differentiation properties in response to polyclonal stimuli, such as CpG oligonucleotides, as a consequence of the tight regulation of the expression of TLRs (Bernasconi N et al., 2003; Bernasconi N et al., 2002; Bourke E et al., 2003). CpG oligonucleotides induce activation of innate immunity and can protect against lethal challenge with a wide variety of pathogens (Krieg A, 2002). For example, those oligonucleotides containing the motif called CpG-B are especially potent activators of primary B cells (Krieg A et al., 1995; Gursel M et al., 2002; Klinman D, 2004; Eaton-Bassiri A et al., 2004).

Several categories of compounds that are active as agonists for one Toll-like receptor have been identified (Coban C et al., 2005; Kandimalla E R et al., 2005; Hayashi E et al., 2005; Bourke E et al., 2003; Ambach A et al., 2004; Sen G et al., 2004) and specific screening technologies are available, also for determining the differential production of immunoglobulin classes and subclasses (Henault M et al., 2005; Cognasse F. et al., 2005).

A second group of stimulating agents is represented by cytokines, in particular interleukins known to have such immunostimulating activities (IL-2, IL-4, IL-6, IL-10, IL-13) and that have been compared in the literature (see Callard R and Kotowicz K "Human B-cell responses to cytokines" in Cytokine Cell Biology: A practical Approach. Balkwill F (ed.) Oxford University Press, 2000, pg. 17-31).

A third group of stimulating agents is represented by agonists of cell membrane receptors of the TNF receptor family, in particular those activating the NF-kB pathway and proliferation in B cells, such as APRIL, BAFF, or CD40L (Schneider P, 2005; He B et al., 2004; Craxton A et al., 2003; Tangye S et al., 2003).

It is important to point out that the choice and the concentration of the stimulating agent, their combination, as well as the length of the stimulation phase, has to be chosen to obtain an optimal effect on both cell stimulation and expression of proteins allowing for, or enhancing, immortalization of the antibody-secreting cells.

The Examples show that useful stimulating agents, in particular when the viral immortalizing agent is Epstein-Barr virus, can be chosen amongst the following combination of compounds:

a) A combination of a CpG-based oligonucleotide and a cytokine;
b) A combination of an agonist of a cell membrane receptor of the TNF receptor family and a cytokine.

On the basis of its stimulatory properties, CpG2006 has been used simultaneously with EBV for producing immortalized human B cells (Traggiai et al., 2004; WO 04/76677), as has been done with soluble CD40 Ligand or agonistic antibodies against CD40 (WO 91/09115; WO 94/24164; Tsuchiyama L et al., 1997; Imadome K et al., 2003).

However, a similar approach affects negatively the maintenance and the screening of the immortalized B cells since polyclonal activators such as CpG2006 are known to have potent effects on a variety of cell types that may be present during the cloning and/or the following screening process in cell culture (Hartmann G and Krieg A, 2000; Hartmann G et al., 2000}. In particular, CpGs are potent inducers of cytokines such as IL-12 and IFN-gamma by mononuclear cells and the presence of such cytokines should be avoided in subsequent bioassays, particularly when screening for antiviral antibodies. (Klinman D et al., 1996, Fearon K et al., 2003; Abel K et al., 2005).

The Examples show how an optimized response of human CD22 positive B cells to a combination of CpG2006 and IL-2 is obtained by using specific concentrations of compounds, and that a number of other known stimulating agents (e.g. LPS or SAC) do not provide such a response.

The length of time during which the selected antibody-secreting cells are exposed to the stimulation agents is of great importance for establishing effective methods for immortalizing such cells. In fact, the Examples show that a combination of stimulation agents (CpG2006 and IL-2) exerts a maximal effect on cell viability and proliferation in particular within a specific time frame (for example from about 2 to about 4 days of stimulation). However, alternative combinations of stimulating agents and time frame can be equally effective for EBV immortalization, or for other viral immortalizing agents.

The combination of stimulating agents can be added to the cell culture medium before the immortalization phase at the same time or sequentially (e.g. adding a first stimulating agent immediately after the initial cell selection and a second stimulating agent hours or days later), if this proves to be useful to obtain a better response from the antibody-secreting cells.

The stimulating agents can be directly added in the cell culture medium from diluted stock solutions, or after being appropriately formulated, for example using liposomes or other compounds that can improve their uptake and immunostimulatory activity (Gursel I et al., 2001). The stimulating agents may also be attached to solid matrices (microbeads or directly on the cell culture plates) also allowing a more effective removal.

Given the observations made above on the importance of applying the stimulating agents for a specific period of time and in a specific step of the methods of the Invention, the antibody-secreting cells should be then manipulated in a way that the stimulating agent is efficiently eliminated, in order to avoid any negative effect on the later immortalization and maintenance in cell culture conditions.

Thus, cells can be washed with fresh medium one or more times and, optionally, maintained in normal cell culture medium (for example, from 1 up to 6 days) in order to further dilute and eliminate any remaining effect of the stimulating agents, which may be even inhibited by adding specific compounds into cell culture.

The methods of the Invention are applied on cells that are further selected on the basis of the isotype of the expressed antibody after stimulating the cells and before exposing said selected and stimulated cells to the immortalizing agent (i.e. between the stimulation phase and the immortalization phase).

The isotype-based selection of the cells should be performed by applying means for either positive (allowing the isolation of the specific cells) or negative (allowing the elimination of unwanted cells) selection. For example, given that most therapeutic antibodies approved for pharmaceutical use are IgG (Laffy E and Sodoyer R, 2005), only a population of stimulated IgG positive cells can be selected positively (by FACS or magnetic cell separators) or by depleting cells that express IgM from the population of cells, and consequently enriching for cells that express IgG. Separation technologies for antibody-secreting cells using fluorescence activated or magnetic cell separators are known in the literature (Li H et al., 1995; Traggiai E et al., 2004). Depending on the source of antibody-secreting cells and their final use, depletion (or enrichment) of IgD or IgA expressing cells may also be desired.

A similar approach can be used for isolating cells on the basis of the specific subclass, if such a precise selection is desired (e.g., distinguishing human B cells that express IgG1, IgG2, IgG3, or IgG4 antibodies).

The selected and stimulated population of cells that express antibodies having specific isotypes is now ready for being immortalized using a viral immortalizing agent. Literature shows that different immortalizing agents can be used on antibody-secreting cells, and sometimes even combined in a single process in order to obtain immortalized antibody-secreting cells.

Amongst the viral immortalizing agents, a virus that infects and immortalizes antibody-secreting cells should be preferably used in the methods of the Invention. Viruses having such preference are commonly known as lymphotropic viruses and are grouped in the gamma class of herpesviruses. Members of this virus family infect lymphocytes in a species-specific manner, and are associated with lymphoproliferative disorders and the development of several malignancies (Nicholas J, 2000; Rickinson A, 2001).

EBV (Epstein-Barr virus, also known as herpesvirus 4), and HHV-8 (human herpesvirus 8, also known as KSHV, Kaposi's Sarcoma associated Herpervirus) infect and immortalize human lymphocytes. MHV-68 (murine herpesvirus 68), HVS (herpesvirus Samiri), RRV (Rhesus Rhadinovirus), LCV (primate Lymphocryptovirus), EHV-2 (Equine Herpesvirus 2) HVA (Herpesvirus Ateles), and AHV-1 (Alcelaphine Herpesvirus 1) are other oncogenic, lymphotropic herpesvirus having some common genetic features conserved amongst them and similar pathogenic effects in different mammalian host cells. These viruses can be used whenever the methods of the Invention are applied on antibody-secreting cells obtained from such mammals.

However, not only full virus can immortalize B cells since recombinant DNA constructs that contains specific viral proteins obtained by such specific virus and other virus have been successfully used to immortalize B cells (Damania B 2004; Kilger E et al., 1998). Similar vectors containing viral genes can be transduced into cells, sometimes making use of retroviral systems or virus-like particles into packaging cell lines which provide all the necessary factors in trans for the formation of such particles, can also be used in the methods of the Invention.

Figure 9:
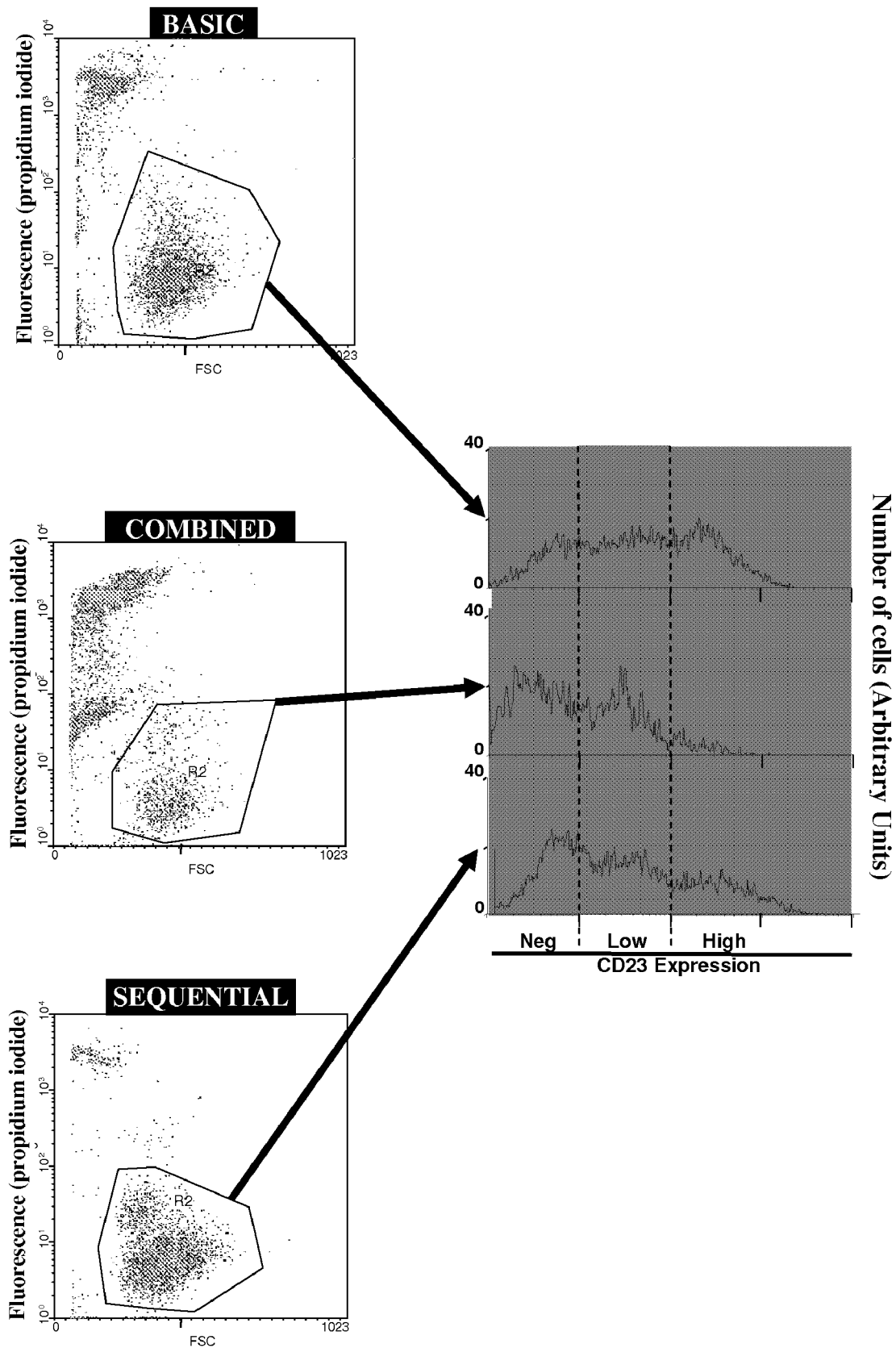
FIG. 9: CD22 positive, IgG positive B cells were prepared using the BASIC, COMBINED, or SEQUENTIAL protocols, as described in FIG. 8 and in Example 2. The resulting populations of cells were analyzed by flow cytometry (by propidium iodide exclusion; left panel) and, in particular for those cells gated under R2, for CD23 expression (using direct immunofluorescence; right panel) at the end of the 10 day culture. The level of CD23 expression in these cells, that are essentially viable lymphoblasts, is indicated as log fluorescence on the horizontal axis (high, medium) and the relative number of cells expressing a given amount of CD23 is shown on the vertical axis. The level of fluorescence considered as negative (neg) was determined using a labeled, isotype-matched negative control antibody.

The immortalization phase can last between 1 and several hours, up to 2-4 days, even though the Examples shows that a longer immortalization phase can be detrimental for cell viability and, in the case of EBV at least, 4 hours can be sufficient to establish polyclonal populations of lymphoblasts (large viable cells, as measured by microscopy and or FACS; see FIG. 9) that provide immortalized antibody-secreting cells.

The Examples show that human B cells can be efficiently immortalized using EBV supernatants if first selected for CD22 expression, then stimulated for an appropriate time (from about 2 days to about 4 days) and with an appropriate combination of stimulating agents (CpG2006 and IL-2), and finally selected on the basis of a preferred isotype (IgG positive or enriched; IgM negative or depleted).

EBV-mediated immortalization of B cells requires the expression of the cell surface receptor CD21 which is considered as the main EBV receptor. CD21 is present on most B cell subpopulations and regulates B cell responses by forming a complex with CD19 and the B cell antigen receptor (Fearon D and Carroll M, 2000). However, CD21 is lost from the cell surface following extensive activation of cells, and as they transform in to plasma cells. Thus, the ability to transform cells with EBV may be aided by the addition of B cell stimulating agents, but the conditions must ensure that CD21 is maintained on the cell surface, allowing EBV immortalization at high efficiency.

The present Invention shows how immortalized populations of antibody-secreting cells can be efficiently obtained. In fact, cell culture populations enriched for B cells that are selected and immortalized have a greater likelihood to produce useful therapeutic antibodies, while maintaining their ability to grow when immortalized with EBV virus in a latent, and not lytic, state. Unlike other methods in which B cells may be stimulated to secrete IgG, the process of immortalization allows the population to be "captured" in a state of high proliferative and IgG-secreting capacity. The supernatant from the population of immortalized B cells may be analyzed for the presence of antibodies with the desired activity. The population of immortalized B cells may then be cloned to isolate clones of antibody-secreting cells, submitted to molecular approaches to isolate antibody genes or stored in a frozen state for future analysis.

EBV-mediated immortalization is a complex process involving the immortalization of B cells due to proteins that are expressed by EBV, followed by the immortalization regulated by the interaction between EBV and host cells proteins (Sugimoto M et al., 2004; Bishop G e and Busch L K, 2002). In fact, the immortalization process can be followed by measuring the expression of specific EBV proteins and transcripts such as EBNA2, EBNA1, LMP2, LMP1, or EBERs (Thorley-Lawson D A, 2001). These proteins can be detected by PCR, immunofluorescence, Western blot, or other methods allowing the detection of EBV DNA and proteins in infected cells (Schlee M et al., 2004; Park C H et al., 2004; Humme S et al., 2003; Konishi K et al., 2001; Haan K et al., 2001).

The amount of EBV supernatant to be added to the cell culture can be that commonly indicated in the literature (10%, 20%, 30%, or more), but it appears that the methods can work properly in conditions in which the amount of EBV supernatant is relatively high (50% V/V) but the exposure is relatively short (from about 4 to about 24 hours).

It is however important that the viral immortalizing agent is eliminated (similarly to what indicated for the stimulating agent), for example by washing and culturing the population of cells into fresh cell culture medium.

The EBV supernatants that can be used in the methods of the Invention can be produced using common techniques for infecting human or rodents cell cultures with any of the EBV laboratory, partially deleted, or recombinant strains (as well as mini-EBV and other EBV-based vectors), and separating the infected cells from the EBV-enriched supernatants (Speck P et al., 1999; Oh H M et al., 2003; Bass H and Darke C, 2004; Radons J et al., 2005; U.S. Pat. No. 5,798,230).

The experimental evidences presented in the Examples suggest that a similar approach can be used with other immortalizing agents. The appropriate combination of selection means for purifying antibody-secreting cells from biological samples and in cell culture conditions, of stimulating agents, as defined above, and of a stimulation phase maintained within a range of hours or days (but always separated from the immortalization phase) may improve the immortalization mediated not only by EBV but also by other viral immortalizing agents, such as the infection with other oncogenic viruses and/or the transformation mediated by oncogenes.

After eliminating the viral immortalizing agent from the cell culture, the resulting population of cells is particularly enriched (when compared to other methods) in viable, proliferating lymphoblasts (see FIG. 9), without the dying, or differentiated cells, that are not only unusable for establishing oligoclonal and monoclonal cell cultures, but also release substances (such as cytokines, reactive oxygen intermediate) in the cell culture medium that can negatively affect the growth, the proliferation, and/or the antibody secretion of the selected and stimulated cells.

In this sense, a polyclonal population of cells obtained according to the methods of the Invention is particularly useful, as well as the oligoclonal or monoclonal populations of cells (containing immortalized antibody-secreting cells) that are obtained by dividing such polyclonal population.

These populations of cells can be used for a series of applications, in particular related to antibody isolation, characterization and production.

For example, a DNA library comprising DNA sequences that encode antibodies of one or more specific isotypes, wherein said DNA library is prepared using nucleic acids isolated from these population of cells. Using common molecular biology techniques, the mRNA or the genomic DNA can be extracted from a sample of cells, retrotranscribing (if necessary) and amplifying specifically all the sequences present in the sample that encode an antibody, in its entirety or only partially (e.g. only the variable regions that bind an antigen), as described in the literature for immunized animals or hybridomas, at the scope of expressing these sequences as recombinant proteins to be screened (Gilliland L K et al., 1996; Lightwood D et al., 2006).

Therefore, the methods of the Invention provide populations of cells, cultures of cells, supernatants of cell cultures, and DNA libraries that can be used for identifying and producing monoclonal antibodies having the desired antigen-binding specificity and/or biological activity.

Alternatively, such biological products, if obtained from antibody-secreting cells provided by an individual, can be used for determining the features of the isotype-specific, immune response to an autologous or heterologous antigen, a virus, a bacterial cell, a toxin, a parasite, or a vaccine in the specific individual (for example, identifying the antibodies prevalently produced and/or the antigens prevalently recognized by the immune system in the individual).

Given the extensive use and stability (as frozen samples) of such biological products (i.e. populations of cells, cultures of cells, supernatants of cell cultures, and DNA libraries of the Invention) can be comprised in kits for identifying and producing a monoclonal antibody having the desired antigen-binding specificity and/or biological activity. For example, the user of the kit can screen in the laboratory a panel of cell culture supernatants or of DNA libraries for the presence of monoclonal antibodies having the desired properties.

The present Invention provides polyclonal populations of immortalized antibody-secreting cells obtained using the methods described above. These populations of cells can be used in a method for producing a cell culture secreting a monoclonal antibody with a desired antigen specificity and/or biological activity comprising the following steps:
  a) Dividing a population of cells of claim 5 or a cell culture of claim 6 in cell cultures each containing 50 or more cells;
  b) Screening the supernatant of said cell cultures for detecting those showing the desired antigen-binding specificity and/or biological activity;
  c) Dividing the cell cultures showing the desired antigen specificity and/or biological activity in cell cultures or populations;
  d) Repeating steps (b) and (c) on said cell cultures until one or more cell cultures, each secreting a monoclonal antibody having the desired antigen-binding specificity, and/or biological activity in the supernatant of the cell culture.

Alternatively, these populations of cells can be used in a method for producing a cell culture secreting a monoclonal antibody with a desired antigen specificity and/or biological activity comprising the following steps:
  a) Screening the supernatant of cell cultures obtained by multiple populations of claim 6 for detecting one or more that secrete antibodies having the desired antigen specificity and/or biological activity;

b) Determining the sequence of the antibody secreted by each of the cell cultures that shows said activity in the supernatant;

c) Isolating the cell cultures that secrete a monoclonal antibody in the cell culture supernatant having such activity.

In order to perform correctly such methods, the polyclonal, oligoclonal, and monoclonal populations of cells have to be maintained in appropriate cell culture conditions for measuring their properties, in particular concerning the antigen-binding and/or functional activity of the antibody they secrete in the supernatant of the cell culture.

In this sense, the choice of the cell culture conditions after the immortalization phase is of particular importance, in order to support viability, proliferation, and antibody secretion of the immortalized antibody-secreting cells.

In this context, the choice of the cell culture conditions can be determinant for establishing, selecting, and growing oligoclonal and monoclonal cell cultures. At this scope, the pools of antibody-secreting cells can be maintained in a cell culture medium containing one or more agents stimulating B cell growth.

In the case of EBV-mediated immortalization, the EBV infection should be maintained in a latent stage, to enhance viability, proliferation and IgG production of the cells. However, the choice of specific cell culture conditions may enhance cloning efficiency and the selection of the monoclonal cell cultures of interest as reviewed in the past (James K and Bell G, 1987).

A first important aspect is the feeder layer used for culturing the antibody-secreting cells following the immortalization phase, when cells are cultured at low density. The feeder layer can be constituted by irradiated non-/allogeneic peripheral blood cell preparations, lymphoblastoid or fibroblast cell lines, cord blood lymphocytes, or different types of embryonic cells. An example of a cell line having such properties is EL4-B5, mutant EL4 thymoma cell lines that efficiently supports the growth and the proliferation of B cells (Ifversen P et al., 1993; Wen et al., 1987).

A second important aspect is how the cells are maintained in culture using a container. Different procedures and materials can be used including stationary culture (in wells or flasks), homogeneous suspension culture (in continuous stirred reactor or roller bottles), or immobilized culture (on hollow fibers or other supports).

A third important aspect is the choice of the cell culture medium to maintain viability and growth of the cells when both performing the methods of the Invention and culturing the cells after the immortalization phase. Especially in this latter period, the choice of cell culture medium (such as IMDM or RPMI-1640) and of cell nutrients (e.g. amino acids, serum) is important to enhance the growth and the replication of the population of cells even when seeded at low cell density, as in the oligoclonal cell cultures.

Finally, a fourth important aspect is the addition of specific B cell growth promoting agents in the cell culture medium, such as any of those used in the stimulation phase, as summarized above (e.g. CpG-based oligonucleotides, Interleukins), or any other compound known to have similar growth promoting effects on immortalized antibody-secreting cells, in particular after EBV immortalization, such as 4-Hydroxynonenal (Ranjan D et al., 2005), forms of thioredoxin (Wendel-Hansen V et al., 1994), soluble CD40 Ligand or agonistic antibodies against CD40 (WO 91/09115; WO 94/24164; Tsuchiyama L et al., 1997; Imadome K et al., 2003), or cyclosporin (Tanner J E and Menezes J, 1994; Chen C et al., 2001).

The choice of the B cell growth promoting agent, as well as of the period of time in which the agent is applied (e.g. only in the days immediately after the immortalization of the cells) depends also on the type of screening assay that is later used. If such agent may interfere, in the case of cell-based assays, by modifying the response of the target cells, the cell culture supernatants cannot be used directly in the assay, unless the specific agent is eliminated or substituted from cell culture medium. Alternatively, antibodies may be at least partially purified from the cell culture supernatants (e.g. by protein precipitation, dialysis, and/or affinity purification). It is however preferable to proceed with the screening assays as soon as possible after seeding the pools of cells, and without the need to eliminate B cell growth promoting agents (or any other element present in cell culture supernatant) by establishing appropriate conditions that do not elicit problems in the screening assays, by washing the cells, or by changing the cell culture medium The antibody-producing cells are isolated, stimulated, and immortalized according to the methods of the Invention, and then can be kept in bulk cultures for a variable number of days (e.g. from 1 up to 10 days, or for longer periods of time such 2-4 weeks) before being subdivided into several pools, each representing a population of cells, that are cultured separately (e.g. in 6-, 12-, 24-, 32-, or 96-well plates).

This bulk, polyclonal population of cells maintained in cell culture conditions may be tested using the assays performed already on sera to select the donor, or any other assay relevant for future use of the cells, in order to confirm the presence of cells. Moreover, some aliquots of the polyclonal population of cells may be put in vials and stored as frozen cells (as normally done for established mammalian cell lines), to be thawed and cultured again later.

The pools of cells are multiple, and they can be 10 up to several hundreds (or even thousands, as shown in Example 3), each containing, statistically, 10, $10^2$, $10^3$, $10^4$, $10^5$ or more cells. The Examples show how cell cultures secreting antibodies can be established starting from populations containing statistically 5, 20, 50 and 100 cells. After a variable number of days (e.g. from 1 up to 10 days, or for longer periods of time such 2-4 weeks), these pools of cells should have secreted antibodies in an amount sufficient for their characterization, for example by using cell culture supernatants (directly or after a partial purification of the antibodies contained herein) in a cell-based or any other binding assay.

Cell cultures that contain at least $10^3$, $10^4$, or $10^5$ cells can secrete an amount of antibodies that is accumulated in the cell culture supernatant (e.g. between 1 and 300 µg/ml of total or more) that can be easily measured with commercial ELISA kits and is generally sufficient for performing similar in vitro analysis. Moreover, $10^5$, $10^4$, $10^3$ or even less cells are sufficient to obtain the sequence of the secreted antibody by extracting, amplifying, cloning, and sequencing the associated mRNA from these cells (as shown in Example 3).

Thus, aliquots of the cell culture supernatant can be then screened for their binding and/or functional activity in a high throughput manner, in order to identify the positive well(s) presenting the desired activity, possibly using a dose-response analysis with serially diluted culture supernatants or partially purified antibody preparations (e.g. obtained by affinity chromatography on protein A columns) in parallel experiments.

The positive pools of cells (i.e. those showing the desired antigen specificity and/or biological activity) can be then used to generate a new series of pools of cells to further restrict the screening to the level of cell culture(s) and consequently isolate the cell cultures secreting a monoclonal antibody having the desired specificity and activity, at least at the level of the initial screening assay. The selected monoclonal antibodies should be then re-evaluated using other more demanding functional assays and characterized at the level of isotype and of VH/VL sequence, after isolating them from stable EBV-immortalized clones using the recombinant DNA technologies applicable on B cells.

This initial characterization, if corroborated by further data obtained using relevant models and clinical experimentation, can lead to the identification of the monoclonal antibody purified from said supernatants (or later expressed as a recombinant protein) as having diagnostic and/or therapeutic uses. In particular, if the original population of cells that has been immortalized according to the methods of the Invention was an IgG positive population of human B cells, this monoclonal antibody is a human monoclonal IgG antibody that can be directly used for treating infections and diseases in humans.

A scale-up of the antibody production can be performed using mammalian, bacterial, or plant cell systems in which the cloned sequences encoding the entire heavy and light chains (or their antigen-binding regions only) of the selected antibodies are cloned using vectors and expressed as recombinant proteins.

The methods of the Invention provide immortalized oligoclonal and monoclonal cell cultures of antibody-secreting cells that can be isolated on the basis of the desired antigen specificity and/or biological activity, as it can be determined for example by screening the cell culture supernatant obtained from the original polyclonal populations of antibody-secreting cells and the oligoclonal or monoclonal cell cultures of antibody-secreting cells. These cells can be then used for identifying and producing a monoclonal antibody having the desired antigen specificity and/or biological activity. At this scope, specific technologies are amenable to automation, allowing antibody production throughput from several monoclonal cell cultures to be significantly increased (Chambers R, 2005).

The screening assays to be used with the cell culture supernatants and purified preparations should be chosen and established in order to detect the antibodies of interest with the highest possible precision. The screening assays should contain and have appropriate positive and negative controls (e.g. other antibodies originated in other screenings or of commercial origin) and should as well be sensitive enough to measure binding and/or functional activities in the range of concentrations that is appropriate for the desired use of the antibody (e.g. for diagnostic, therapeutic, or prophylactic use).

For example, if the antibody is expected to be used as a therapeutic compound, the assay should indicate that a significant activity is detectable with a concentration of antibody of 100, 10, or 1 µg/ml (or lower). Nonetheless, at this early stage of the antibody characterization, the activity measured by the assay is generally being sensitive enough to just be predictive in some way of an activity that is therapeutically useful. Additional assays on purified or recombinant IgG are more critical in respect to therapeutic efficacy and to the associated dose to be possibly administered.

The screening assays should be established to determine the antigen-binding specificity and/or biological activity to which the antibodies are directed, and can make use of auto/alloantigens (human, mammalian, bacterial, viral, parasite, organic, chemicals, and any other antigenic/allergenic compounds) that have been purified and included in a cell-based or biochemical assay providing a demonstration of the specificity of the interaction with an antigen, or of an effect on cells, tissues, virus, or animal models.

Alternatively, the assays may also be established for determining antigen-binding specificity and/or biological activity towards complex biological, non purified targets such as cells or tissues (e.g. migration in endothelial cells, oncogenic cell growth, etc.).

The results of these assays performed on polyclonal or, even better, oligoclonal populations of cells in cell culture conditions may be used for selecting the populations that should be either stored in frozen vials or used for constructing DNA libraries comprising DNA sequences that encode antibodies of one or more specific isotypes.

Several technologies have been described in the literature for screening antibodies in vitro that can be relevant for specific uses of monoclonal antibodies, and that allow as well a precise and high-throughput characterization of the antibodies. Together with more classical technologies such as immunoprecipitation, western blotting, ELISA, and immunofluorescence, more elaborated approaches make use of small organ cell/organ cultures, chips or multicolored nanoparticles for effective screening assays (Bradbury A et al., 2003; Haab B B, 2005; Lal S P et al., 2002; Olivo P, 1996; Potera C, 2005; WO 05/82926; WO 05/003379; WO 05/83064; WO 05/76013).

Depending on the origin of the antibody-secreting cells and of the screening assays used for selecting specific monoclonal cell cultures and characterizing the monoclonal antibodies, many different uses of such antibodies can be envisaged, such as diagnostic tools (for viral, bacterial or parasite infections, tumors, or cell typing), as prophylactic or therapeutic tools (in particular for treating malignancies infections, immune-mediated or inflammatory disorders, or in the management of transplant patients), for investigating the immune system, and in general antigens of clinical relevance. Thus, these antibodies, in particular human monoclonal antibodies, can be used for preparing pharmaceutical compositions comprising a monoclonal antibody or an antibody fragment, and a pharmaceutically acceptable carrier, for the manufacture of a medicament for treatment of a patient, and for the diagnosis of infectious, oncogenic, autoimmune or allergic diseases in humans.

The present Invention also provides a method for producing a monoclonal antibody comprising the following steps:
a) Expanding a cell culture produced by a method described above; and
b) Purifying the monoclonal antibody from the supernatants of said cell culture.

In particular, a distinct advantage to EBV immortalization is that cell cultures, after having performed the initial characterization and validation of the secreted antibody, may be directly used to purify sufficient amount of antibody (from the microgram to the milligram range) to perform more extensive antibody characterization and validation using in vitro or in vivo assays (further biochemical, tissue- or cell-based assays, disease models established in rodents, biophysical methods for affinity measurements, epitope mapping, etc.).

At this scope, the original cell culture, after controlling the clonality of said culture, can be further optimized by adapting culture medium and conditions for maintaining cell growth and improving antibody expression and secretion (Ling N, 2000). Antibody can be then purified from cell culture supernatants by applying technologies known from the literature for the isolation of antibodies from complex protein mixtures using affinity chromatography (Nisnevitch M and Firer M A, 2001; Huse K et al., 2002). These methods for antibody purification can be based on the general affinity of antibodies for substrates such protein A, protein G, or synthetic substrates (Verdoliva A et al., 2002; Roque A C et al., 2004;

Danczyk R et al., 2003), as well as by antigen- or epitope-based affinity chromatography (Murray A et al., 2002; Sun L et al., 2003; Jensen L B et al., 2004). Other preparative separation devices for antibodies have been elaborated, for example based on electrophoresis (Thomas T M et al., 2003).

Obviously, a monoclonal cell culture can be also used to identify the DNA sequences that encode the monoclonal antibody, by amplifying and cloning them in a vector, before proceeding to the expression of the recombinant antibody in the appropriate host cells. The protein sequence of the antibodies secreted by the selected clonal cell cultures can be easily determined by isolating nucleic acids encoding these antibodies using recombinant DNA technologies that are known in the literature (Poul M A et al., 1995; Jovelin F et al., 1995; Heinrichs A et al., 1995; Dattamajumdar A K et al., 1996; Norderhaug L et al., 1997; Chardes T et al., 1999; Jarrin A and Andrieux A, 1999; Essono S et al., 2003).

These technologies can also be used for further structural and functional characterization and optimization of therapeutic antibodies (Kim S J et al., 2005), or for generating vectors allowing the stable in vivo delivery of monoclonal antibodies (Fang J et al., 2005).

Briefly, mRNA can be prepared from the cell culture and retrotranscribed into a cDNA library, which can be used as a template for a Polymerase Chain Reaction (PCR) including degenerate primers for specifically amplifying full heavy and light chains or only portions of these chains (such as the variable regions). In the case where only the variable regions (responsible of antigen-binding) are isolated, these sequences can be cloned in a vector allowing the fusion of this sequence to constant (Fc) regions of the desired isotype (for example, human IgG gamma1). The PCR-amplified DNA fragments can be directly sequenced or cloned, using adaptors or restriction sites, into vectors for sequencing the coding sequence that can be adapted and recloned in other vectors for expressing antibodies as recombinant proteins.

The mRNA of the polyclonal or oligoclonal populations of cells can also be used for constructing cDNA libraries specific for antibody-secreting cells of specific isotypes that can be made available, for example, as phage display libraries, bacterial libraries, yeast libraries, or any other format of biological library that can be used for replicating and maintaining DNA, in particular DNA encoding proteins. For instance, a library of recombinant antibody sequences can be generated using the mRNA extracted from one or more oligoclonal populations of cells, used for producing antibodies in bacterial or eukaryotic host cells, and then for screening such antibodies at the scope of identifying one or more antibodies that have a desired antigen specificity and/or biological activity.

Once cloned and characterized, the antibodies can be expressed as recombinant proteins in prokaryotic organisms (e.g. *E. coli*; Sorensen H and Mortensen K, 2005; Venturi et al., 2002), plants (Ma J K et al., 2005), or eukaryotic cells, in particular human, rodent, or other eukaryotic cell lines (e.g. CHO, COS, HEK293) that allow a high level of expression as transient or stable transformed cells (Schmidt F, 2004). This would be required in particular when the characterization of the antibodies has to be performed using more sophisticated assays, including in vivo assays. The host cells can be further selected on the basis of the level of recombinant expression of the cloned monoclonal antibody.

At this scope, the cloned antibody sequences can be modified using PCR or other recombinant DNA technologies at the DNA level only (e.g. eliminating or adding restriction sites, optimizing the codon usage, adapting transcription and/or translation regulatory sequences) or at both the DNA and protein level (e.g. adding other protein sequences or modifying internal amino acids). Moreover, fragments (Fv, Fab, F(ab)' or F(ab)") or fusion proteins based on these antibodies can be produced using recombinant DNA technologies.

For example, recombinant antibodies can also be modified at the level of structure and/or activity by choosing a specific Fc region to be fused to the variable regions (Furebring C et al., 2002), by adding stabilizing peptide sequences, (WO 01/49713), by generating recombinant single chain antibody fragments (Gilliland L K et al., 1996), or by adding radiochemicals or polymers to chemically modified residues (Chapman A et al., 1999).

Different vector systems have been used for generating stable pools of transfected cell lines (Aldrich T L et al., 2003; Bianchi A and McGrew J T, 2003). High level, optimized, stable expression of recombinant antibodies has been achieved (Schlatter S et al., 2005; Dinnis D and James D, 2005; Kretzmer G, 2002), thanks to the optimization of cell culture conditions (Grunberg J et al., 2003; Yoon S K et al., 2004) and by selecting or engineering clones with higher levels of antibody production (Bohm E et al., 2004; Borth N, 2002; Chen K et al., 2001; Butler M, 2005).

The purification of non-/recombinant antibodies from cell cultures can be performed using the technologies described and others streamlined in the literature (Hale G et al., 2004; Horenstein A L et al., 2003). However, clinical development and use should be based on the characterization of the antibody pharmacokinetics and pharmacodynamics (Lobo E et al., 2004) and compliancy to international requirements for the production and quality control of murine, human and engineered monoclonal antibodies for therapeutic and in vivo diagnostic use in humans (EUDRA document 3AB4a).

The Invention will now be described by means of the following Examples, which should not be construed as in any way limiting the present Invention.

EXAMPLES

Example 1

Effect of Methods for Cell Purification and Stimulation on the Viability and Proliferation of B Cells in Cell Culture Conditions Materials & Methods
Isolation and Maintenance of Human B Cells Fresh peripheral blood mononuclear cells (PBMCs) were purified from peripheral blood by conventional density gradient centrifugation on Ficoll/Hypaque. Depending on the experiment, the cells were then processed using PBMCs from a single donor or pooled PBMCs from five different donors, in order to evaluate an average response to the different experimental conditions and to limit differences due to donors variability.

Human B cells were isolated from PBMCs by immunomagnetic cell sorting using the VarioMACS technique (Miltenyi Biotec Inc.) as described by the manufacturer. In brief, PBMCs were suspended in PBS (Phosphate-Buffered Saline) supplemented with 0.5% BSA (Bovine Serum Albumin) and 2 mM EDTA (ethylenediamine-N,N,N',N'-tetraacetate) and incubated with different microbead-conjugated antibodies (directed to CD19, to CD22, or to CD27). The microbead-bound cells were then washed and passed over a column for their positive selection (LS column; Miltenyi cod. 30-042-401) under a magnetic field. Cells then were released from the microbeads using the MACS MultiSort releasing reagent (20

μl/ml) at 4° C. for 10 minutes, following manufacturer's instructions (Miltenyi Biotec Inc.).

IgG positive B cells were obtained by negative selection of IgM positive cells by cell sorting or by magnetic selection of IgG positive cells by using the VarioMACS technique (Miltenyi Biotec Inc.), following the manufacturer's instructions. For cell sorting, CD22 positive B cells (with or without previous stimulation) were incubated with optimal concentrations of anti-human IgM-FITC (Becton Dickinson n.555782) for 1 hour on ice. Cells were extensively washed with PBS then sorted into IgM positive and IgM negative cells under sterile conditions using a high-speed cell sorter (MoFlo® High-Performance Cell Sorter).

The selected cells were suspended and maintained in RPMI-1640 cell culture medium supplemented with 10% (v/v) heat-inactivated FCS (Fetal Calf Serum), 1 mM sodium pyruvate, 100 ug/ml streptomycin and 100 U/ml penicillin and cultured in 24-well plates at 37° C. and 5% CO2.

Stimulation of B Cells in Cell Culture

CpG2006 (5'-TCGTCGTTTTGTCGTTTTGTCGTT-3'; SEQ ID NO: 1) was purchased from Coley Pharmaceutical Group. Recombinant human Interleukin 2 (IL-2) was obtained by Roche. Recombinant human Interleukin 4 (IL-4) was obtained from Peprotech. Recombinant human CD40 ligand (soluble fragment comprising amino acids 108-261) was obtained from R & D Systems. *Staphylococcus aureus* Cowan strain (SAC) and lipopolysaccharides (LPS) were purchased from Sigma.

Measurement of B Cell Proliferation by $^3$H-Thymidine Uptake.

Cells ($2\times10^6$/ml) were seeded in 96-well plate (50 μl/well) in triplicate samples in the indicated culture conditions and labeled with $^3$H-thymidine (NET-027X Thymidine, methyl-3H; specific activity 20 Ci/mmol; PerkinElmer) that was added (0.5 μCi/well) 8-16 hours before the end of the experiment. Uptake of $^3$H-thymidine was measured by harvesting cells into glass fiber filters that were counted using a beta-counter (Wallach Instrument).

Analysis of Surface Marker Expression by FACS

Cells ($3\times10^5$/sample) were suspended in PBS with 0.5% bovine serum albumin and incubated for 30 minutes at 4° C. with the selected monoclonal antibodies against CD22 labeled with FITC. After washing, fluorescence was analyzed using a FACSCalibur flow cytometer and CellQuest software (Becton Dickinson). Back-ground binding activity of the monoclonal antibodies was estimated by means of isotype-matched negative control monoclonal antibodies. The number of cells analyzed was 10000.

FACS-Based Cell Sorting

Cell sorting was performed using a MoFlo® High-Performance Cell Sorter (Dako). Negative selection of IgG expressing cells was performed starting from cells ($10^7$/ml) that were incubated with anti-human monoclonal IgM-FITC (10 μl/$10^6$ cells; Becton Dickinson Cat. No. 555782) or anti-human polyclonal IgM-FITC (2 μl/$10^6$ cells; Jackson, Cat. No. 309-096-043) for 1 hour at 4° C. Cells were then washed and suspended (10-20×$10^6$/ml) in sorting buffer (PBS with 5 mM EDTA, 25 mM Hepes and 1% FCS). Cells were gated on the basis of morphological parameters (R1). CD22 positive, IgM negative B cells were selected inside the R1 area.

Results

The literature provides poor comparative information on the effect of the different approaches for purifying and stimulating B cells on cell viability and proliferation in cell culture conditions.

Interleukin 2 (IL-2) was used as a reference compound, given the well-described growth promoting effects of this cytokine on primary human B cells in cell culture (Banchereau J and Rousset F, 1992). A first comparison was made using primary B cells that were purified from human PBMCs on the basis of CD22 surface expression on their surface, and then co-stimulated with well-known polyclonal B cell stimulators: CpG2006, lipopolysaccharides (LPS), soluble CD40 ligand (CD40L), and *Staphylococcus aureus* Cowan strain (SAC).

Figure 2:
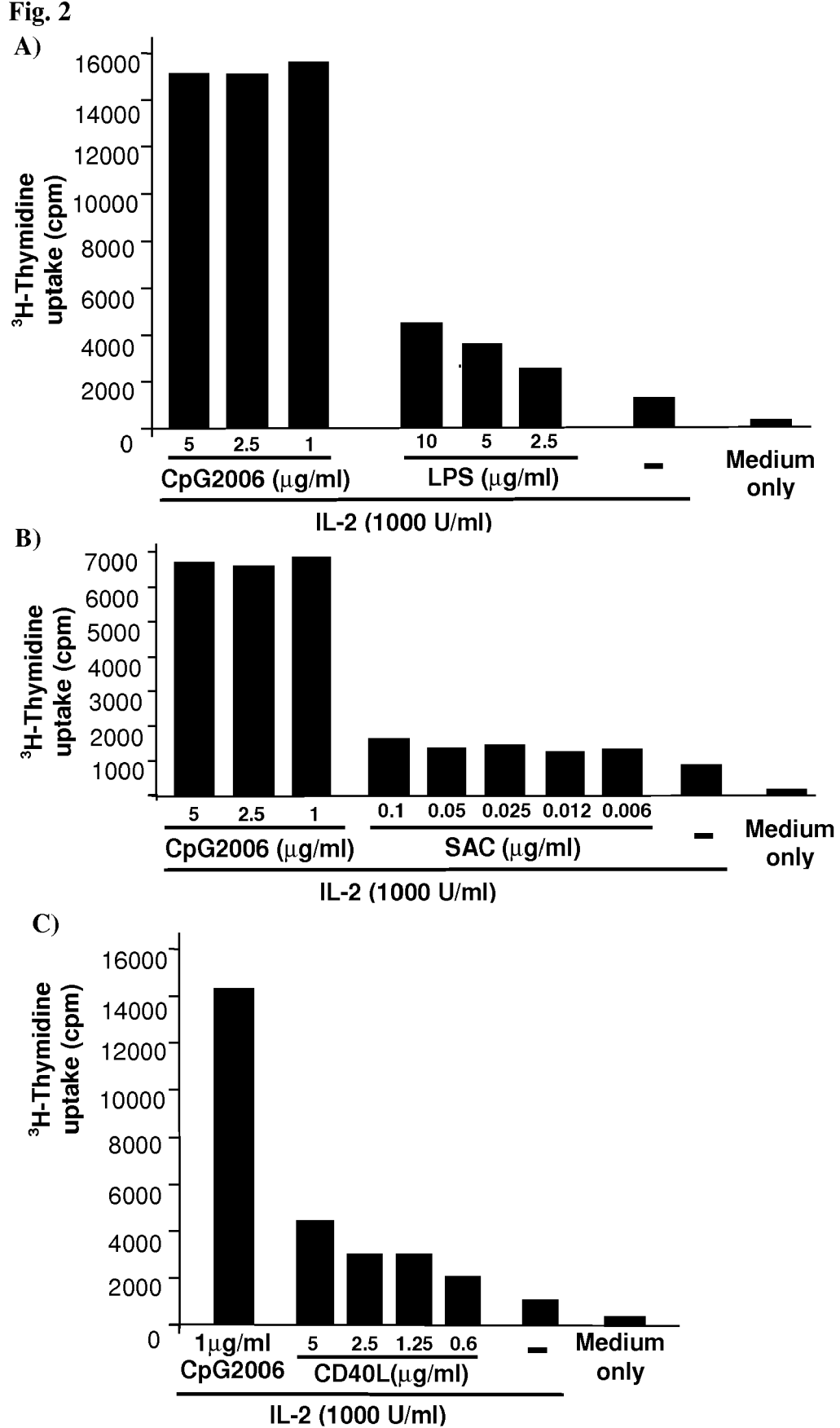
FIG. 2: Effect on the proliferation of primary B cells cultured in the presence of IL-2 (1000 U/ml) alone or combined with CpG2006, LPS, SAC or CD40L. Human CD22-positive B cells were purified by magnetic separation from PBMCs pooled from five donors. B cells were cultured for 4 days in the presence of the indicated concentrations of compounds. $^3$H-Thymidine was added to the culture only on the last day, incubating the cells with labelled nucleotide for 8-12 hours. Samples cultured with medium only, medium with IL-2, or medium with CpG2006 were present in all experiments. The effects of the combination of IL-2 with the stimulating agents LPS (A), SAC (B) and CD40L (C) were examined as indicated. The values of counts per minute (cpm) are reported as means of triplicate wells. The different absolute cpm values between (A), (B), and (C) are due to the differences in the specific activity of the $^3$H-thymidine batches used for each experiment.

A positive dose-response on cell proliferation was measured when LPS, SAC, and CD40L were added in cell culture, together with IL-2, in a 4 day $^3$H Thymidine uptake assay. However, the combination of CpG2006, added in concentrations generally described in the literature (Bemasconi N et al., 2003; Traggiai E et al., 2004), shows that this compound, when combined with IL-2, has a markedly higher potential to induce proliferation of B cells in cell culture (FIG. 2). Proliferation-inducing effects results, similar to those obtained with a combination of CpG2006 and IL-2, were obtained in this assay by combing soluble CD40L (at a concentration of least 0.5 μg/ml) with another cytokine, IL-4 (at least 20 ng/ml), suggesting that this combination of compounds can be used as a stimulating agent in the methods of the Invention, once that optimal kinetics and effects on IgG secretion are determined.

Given the extent of the effect identified with a combination of IL-2 and CpG2006, a titration of CpG2006 for optimal B cell proliferation and blast formation was performed using range of CpG2006 concentrations from 0 up to 2.5 μg/ml, while maintaining a constant concentration of IL-2.

Figure 3:
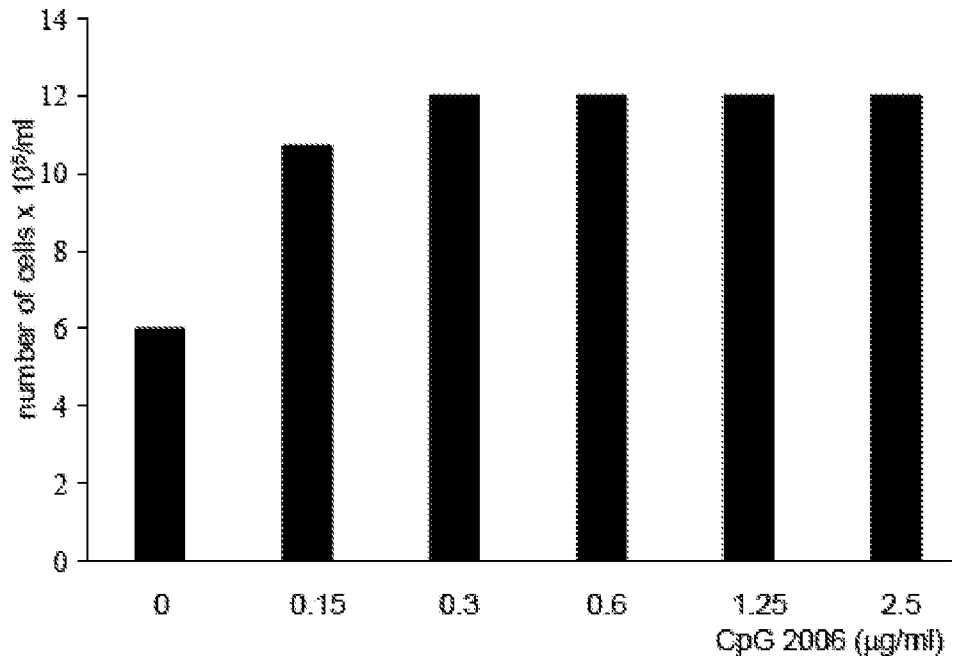
FIG. 3: Dose-dependent effect of CpG2006 on the proliferation of human CD22-positive B cells. Human CD22-positive B cells were purified by magnetic selection from PBMCs pooled from five donors. B cells were cultured with the indicated concentration of CpG2006 and IL-2 (1000 U/ml) for 2 days. The number of viable cells (A) was determined microscopically by trypan blue dye exclusion. In parallel, ten thousand events from each indicated culture condition were analyzed by flow cytometry (B), measuring both the percentage of viable cells (black bars) and blast cells (cells with higher forward and orthogonal scatter, white bars).
Figure 3:
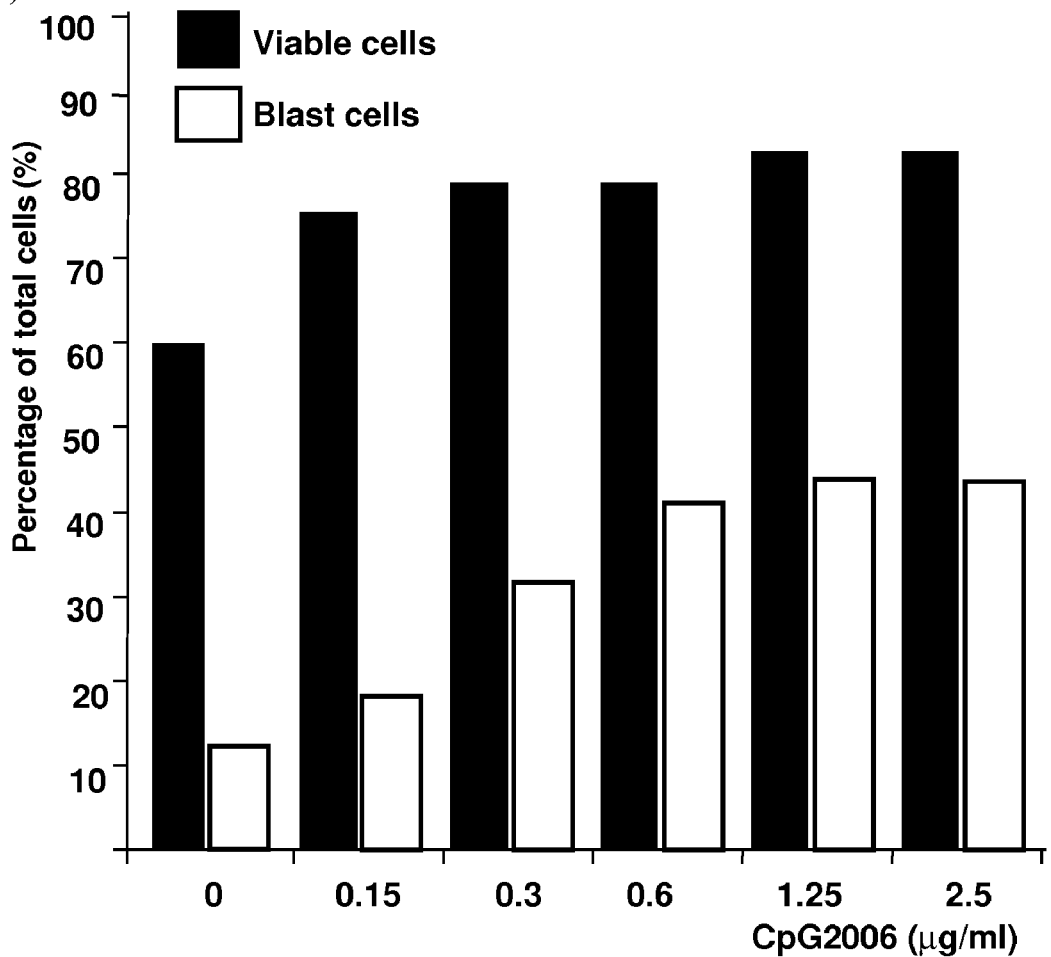

A significant CpG2006-induced proliferation of CD22 positive human B cells was detected at concentrations as low as 0.15 μg/ml, with a plateau achieved at 0.3 μg/ml (FIG. 3A). When the same populations of cells were analyzed by FACS for the percentage of viable cells and blasts (large cells with high forward scatter) the optimal CpG2006 concentration appears to be slightly higher (between 0.6 and 1.25 μg/ml) since a higher percentage of blast cells are generated at these concentrations (FIG. 3B).

This evidence on the CpG2006/IL-2 combination, while confirming previous results indicating that B cell stimulatory effects of CpG2006 can be obtained at concentrations below 1 μg/ml, shows that proliferation and blast formation of stimulated CD22 positive B cells can be obtained in a range of CpG2006 concentrations (0.3-1 μg/ml).

In these experiments, IL-2 was added at a constant concentration (1000 U/ml), but a similar dose-response can be performed with IL-2 at different concentrations, while CpG2006 concentration is constant, to further define the optimal concentration of IL-2 capable of inducing human B cell proliferation and blast formation in the presence of CpG2006. Subsequent experiments also showed IL-2 can be used in a range of concentrations between 100 U/ml and 1000 U/ml).

Thus, in addition to the choice of the polyclonal B cell stimulators, determining the concentration at which the specific compounds should be used (alone or in combination) is important for obtaining the desired effect on the cell proliferation. Responsiveness and proliferation of B cells to CpG2006-based activators and cytokines was shown for CD19/CD27 positive cells (Bemasconi et al., 2002; Jung J et al., 2002). However, at least some of the negative effects of CpG2006 on B cell viability known in the literature (Hartmann et al., 2000; Klinmann D et al., 1996; Fearon K et al., 2003) appear to be reduced by applying specific conditions, concentrations, and combinations of compounds.

The method for purifying primary B cells from biological samples can be a further element to be considered for establishing a process in which the viability and the proliferation potential of these primary B cells is not jeopardized by cell culture conditions and in vitro manipulations in the presence of stimulating agents.

Two cell surface markers are predominantly described in the literature as being useful for positively selecting human B cells, using for example solid supports: CD19 and CD22. The stimulation protocol combining IL-2 and CpG2006 was applied on human B cells purified with either CD19- or CD22-specific microbeads.

Figure 4:
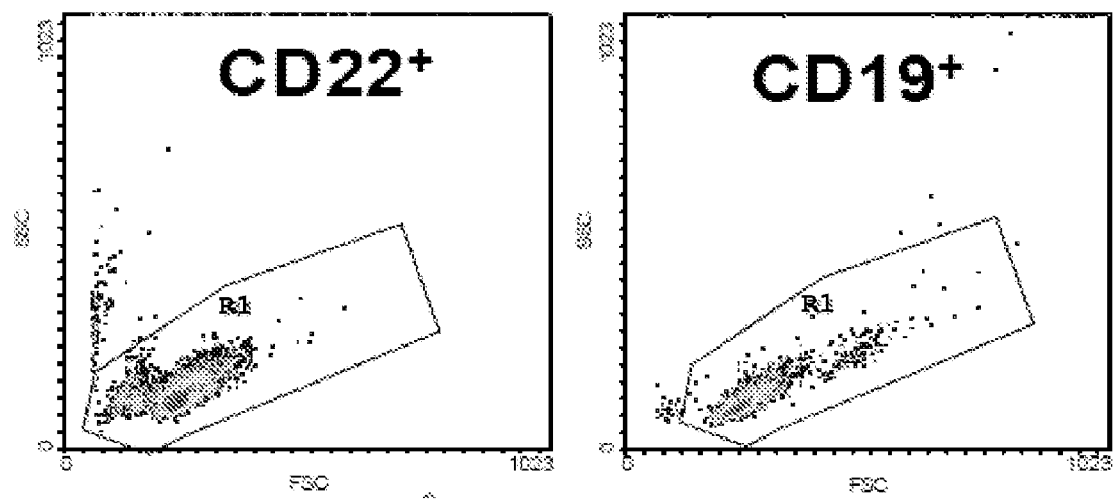
FIG. 4: FACS-based analysis of viability and blast formation of CD22 or CD19 positive B cells purified by magnetic separation of PBMCs pooled from five donors. The analysis was performed before (A) or after (B) a 4 day culture with a combination of CpG2006 (1 µg/ml) and IL-2 (1000 U/ml) (B). In each panel, 10,000 events were analyzed by forward scatter (horizontal axis) and orthogonal scatter (vertical axis), as a measure of size and granularity, respectively. Viable B cells are gated in the R1 region. Dead cells with lower forward scatter are aligned with the vertical axis, outside of R1. Cells undergoing blast differentiation have higher forward and orthogonal scatter.
Figure 4:
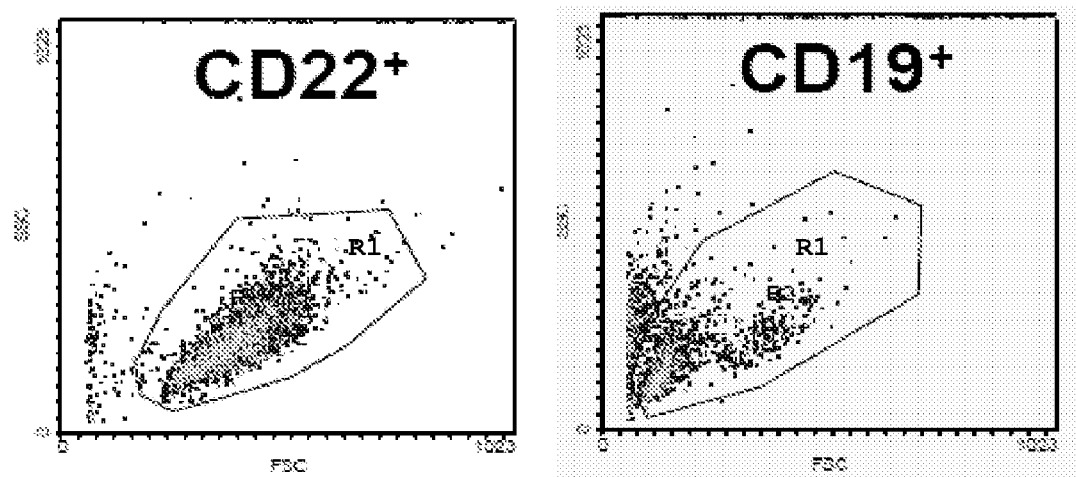

A FACS-based analysis of cell viability and blast formation was performed before and after the stimulation. The comparison between these two approaches for cell purification clearly showed that, immediately following the purification, the CD22 positive population of cells is more homogeneous than the CD19 positive population (FIG. 4A). This cell response to the purification approach is even more evident after 4 days of stimulation (FIG. 4B), when the CD22 positive population had a higher frequency of viable cells and a much greater proportion of large, activated cells than did the CD19 positive population. The increased viability of the B cells purified with microbeads loaded with the CD22 specific antibodies, rather than with CD19 specific antibodies, may be due to different downstream effects on the growth potential of those cells that are exerted by the two different selection means.

Moreover, CD22 positive B cells can be selected and stimulated by applying additional selection means, such as microbeads for the positive selection of IgG-expressing cells, or any other relevant B cell subset, such as CD27 positive memory B cells.

Once shown that the choice of means for both cell stimulation and selection affect cell viability and proliferation, a further element that may be involved is the kinetics of the cell viability and of the proliferation response of CD22 positive, human B cells to the isolated or combined stimulation with IL-2 and CpG2006.

Figure 5:
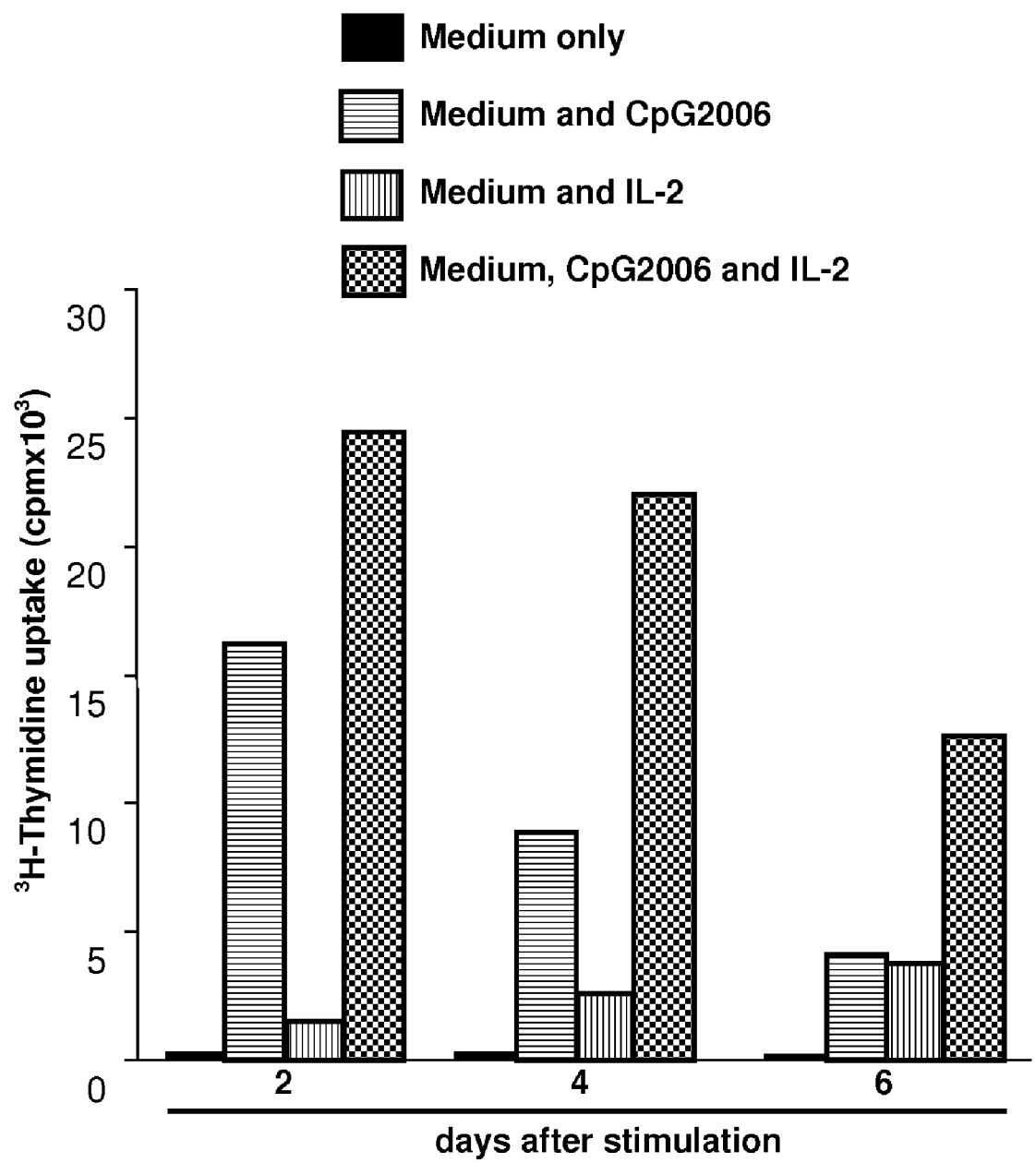
FIG. 5: Kinetics of cell proliferation and cell viability in B cells stimulated with a stimulating agent (a combination of CpG2006 and IL-2). Human CD22 positive B cells were selected by magnetic separation of PBMCs pooled from five donors. Cells were cultured in the presence of CpG2006 (1 µg/ml) and IL-2 (1000 U/ml) for the indicated time points. Proliferation was assessed by $^3$H thymidine incorporation.

Cell viability and proliferation was measured 2, 4, and 6 days after starting the stimulation, showing that the combined effect of CpG2006 (1 µg/ml) and IL-2 (1000 U/ml) provides a distinct kinetics. Maximal $^3$H-Thymidine incorporation induced by CpG2006 alone is observed as early as 2 days in culture and declines rapidly thereafter. The kinetics of the cell proliferation response to IL-2 alone is more gradual, with increasing $^3$H-Thymidine incorporation up to day 6 of culture. However, the combined stimulation with CpG2006 and IL-2 provide kinetics of $^3$H-Thymidine incorporation similar to that of CpG2006, but with a surprisingly enhanced effect at day 2, that continues until day 4 and declines by day 6 of culture (FIG. 5). In parallel, the total number of viable cells in cultures stimulated with CpG2006 and IL-2 was measured, again showing a higher number of viable cells at day 2 and day 4.

Thus, the advantage of combining the two stimulating agents is clearly more important when, especially at day 4 of culture, an equilibrium between the effects triggered separately by IL-2 and CpG2006, having kinetics of opposite direction, can be achieved. These data also suggest the possibility that similar, or even better, effects on cell proliferation and viability can be exerted on antibody-secreting cells not only by adding the stimulating agents simultaneously but also sequentially (i.e. one at the beginning of the stimulation phase and the other after some hours or days).

Example 2

Effect of Methods for Cell Purification and Stimulation on the Viability Proliferation, and Antibody Secretion of B Cells Immortalized Using EBV Materials & Methods
Selection and Analysis of B Cell Proliferation and Viability
The selection of human B cells, their stimulation, and the analysis were performed as indicated in Example 1, unless otherwise indicated.
Analysis of Surface Marker Expression by FACS
CD21 positive cells were detected by immunofluorescence and flow cytometry, using anti-CD21-PE conjugate (Caltag Laboratories, Cat. No. MHCD2104, batch 04061206), as indicated above for CD22.
Preparation of Epstein-Barr Virus (EBV) Supernatants
EBV-producing B95-8 marmoset lymphoma cells (ATCC No. CRL-1612; 5×10$^5$/ml) were grown in RPMI-1640 cell culture medium supplemented with 10% FCS (complete medium) for 4 days.
Exponentially growing B95-8 cells were stimulated with 100 nM phorbol esters (e.g. PMA; Sigma) for 2 hours (Oh H M et al., 2003), then extensively washed with HBSS (Hank's balanced salt solution; Sigma) to remove PMA in solution. The PMA-stimulated B95-8 cells were cultured in complete RPMI-1640 cell culture medium added with 10% FCS for 48 hours, and supernatant was collected, centrifuged and filtered through a 0.22 µm membrane.
The immortalization efficiency was evaluated on 3 distinct preparations of CD22 positive B cells from different blood donors. In all cases, a rapid immortalization was observed and polyclonal lymphoblastoid lines were obtained showing rapid replication. The immortalizations performed in parallel with a batch of virus prepared under conventional conditions, in the absence of PMA stimulation, showed a slower replication.
EBV-Mediated Immortalization of Human CD22 Positive, IgM Negative, Stimulated B Cells
Following 4 days of stimulation with IL-2 (1000 U/ml) and CpG2006 (1 µg/ml), the CD22 positive, IgM negative cells were extensively washed with fresh medium to remove the stimulating agents before being exposed to EBV supernatants.
The bulk immortalization of the cells was performed by incubating them (10$^6$/ml) with EBV supernatant (50% V/V in RPMI-1640 added with 10% FCS) for a minimum of 4 hours up to 18 hours, and then washed with fresh medium. Proliferation and viability of cells that are treated with 50% EBV supernatant for 4-18 hours is comparable to the proliferation and viability of cells that are treated with 30% EBV supernatant for 7 days.
The cells are then concentrated (10$^6$/ml in RPMI-1640 added with 10% FCS and IL-2, 1000 U/ml) and seeded on 0.5×10$^5$ irradiated (3000 rad), allogeneic PBMCs per well in a 24 well plate for a period of 8-16 days.
Qualitative and Quantitative Comparison of the Outcome of Different Methods for Human B Cell Immortalization Using EBV
The human B cells have been isolated as CD22 positive peripheral blood mononuclear cells (PBMCs) pooled from 5 normal donors by magnetic selection as described for Example 1 and then divided in three pools of cells each exposed to a different EBV-based method for B cell immortalization In the BASIC method, the IgG positive fraction of these cells were selected by cell sorting using a MoFlo high-speed cell sorter (MoFlo Cytomation) and anti-human-IgG FITC (Becton Dickinson). Then, $8 \times 10^5$ CD22 positive, IgG positive cells were cultured for 12 hours with EBV supernatant (prepared as described above), washed and cultured at the density of $1.5 \times 10^6$ cells/ml for 10 days at 37° C. in IMDM medium (Gibco-BRL) supplemented with L-glutamine, non-essential amino acids (NEAE) and 10% FCS, in the presence of irradiated allogeneic PBMC feeder layer.

In the COMBINED method, $8 \times 10^5$ CD22 positive IgG positive cells have been isolated as in the BASIC method and then cultured at the density of $1.5 \times 10^6$ cells/ml with CpG2006 (1 µg/ml) and IL-2 (200 U/ml), and EBV supernatant (prepared as described above) in IMDM medium (Gibco-BRL) supplemented with L-glutamine, NEAE, and 10% FCS for 10 days at 37° C. in the presence of irradiated allogeneic PBMC feeder layer.

In the SEQUENTIAL method, the CD22 positive PBMCs were first prestimulated with a combination of CpG2006 (1 µg/ml) and IL-2 (200 U/ml), in IMDM medium (Gibco-BRL) supplemented with L-glutamine, NEAE, and 10% FCS for 4 days at 37° C. The cells were then washed with PBS and IgG positive cells enriched by magnetic selection as described above. The prestimulated cells ($8 \times 10^5$ CD22 positive IgG positive PBMCs) were then infected with EBV supernatant (as in the BASIC method) for 12 hours at 37° C., washed and cultured at $1.5 \times 10^6$/ml in IMDM medium (with L-glutamine, NEAE and 10% FCS) for 10 days at 37° C., in the presence of irradiated allogeneic PBMC feeder layer Measurement of Cell Number and Viability by Propidium Iodide and Flow Cytometry The total number of B cells was measured by counting microscopically, and their viability by measuring the exclusion of the DNA intercalating, fluorescent dye propidium iodide using a FACSCalibur bench-top flow cytometer and CellQuest Software (Becton Dickinson Biosciences). Briefly, cells were exposed at room temperature to propodium iodide (PI, Sigma; 2.5 µg/ml final concentration in PBS) and analyzed by flow cytometry within 30 minutes. Viable cells were defined as those with a high forward and orthogonal scatter, characteristic of lymphocytes and lymphoblasts, and excluding PI. Cells that were stained with PI, and having a low forward scatter, represent dead cells and debris.

Analysis of Surface Expression of CD23

CD23 expression was measured in viable lymphoblasts that were electronically gated by FACS using direct immunofluorescence (R2 area) and flow cytometry with anti-human CD23-PE conjugate (Becton Dickinson, catalog no. 555711), as described for Example 1.

Measurement of Secreted IgG

Secretion of total human IgG in culture supernatants was measured using an ELISA (Immuno-Tek/Zeptometrics, cat. no. ZMC 0801182) according to the manufacturer's instructions. Briefly, culture supernatants were collected from the cultures and stored at 4° C. Samples of supernatant were serially diluted and compared to a purified human IgG standard curve included with the ELISA kit. The measurement reflects the total amount of IgG accumulated in cultures over the 10 day culture period.

Results

Since the scope of the whole process is to generate immortalized, antibody-secreting human cells in the most direct manner, EBV was chosen as the immortalizing agent, being quite straightforward to establish and apply using supernatant from cells infected by this virus. However, it is well known that only a fraction of the cells exposed to EBV are actually infected, possibly due to the limited expression of CD21, a receptor present on the cell surface that the virus uses for entering the cells (Jondal and Klein, 1973; Nemerow et al., 1985; Boyd and Fecondo, 1988). Therefore it was important to see if CD21 expression was positively or negatively affected by the selected means and conditions for cell stimulation and purification described above.

At this scope, the kinetics of proliferation of B cell populations selected on the basis of different cell markers (CD22 positive only, CD22 positive and CD27 positive, CD22 and IgG positive, CD22 positive and IgM negative) following a 4 day stimulation with IL-2 (1000 U/ml) and CpG2006 (1 µg/ml), and measuring the proportion of CD21 positive cells at different time points. In all the experiments, CD21 was expressed in >90% of the viable and proliferating cells, confirming also the possibility of using a double-selection approach in the context of the methods of the Invention.

Therefore, after demonstrating the strong positive effect on cell proliferation activity exerted by selected means and conditions for cell stimulation and purification, it was tested how this approach may provide as well an improvement in how B cells respond to an immortalizing agent. In fact, it is well known that, following the exposure of B cells to EBV, a substantial fraction of the cells stop growing and die within the first week of culture, followed by the resumption of proliferation by the EBV immortalized cells (James K and Bell G, 1987). Thus, it would be of great importance to understand if an adequate proportion of appropriately stimulated and selected human B cells not only can be immortalized with EBV, but also if these immortalized B cells are better able to overcome the critical period following the EBV immortalization.

Figure 6:
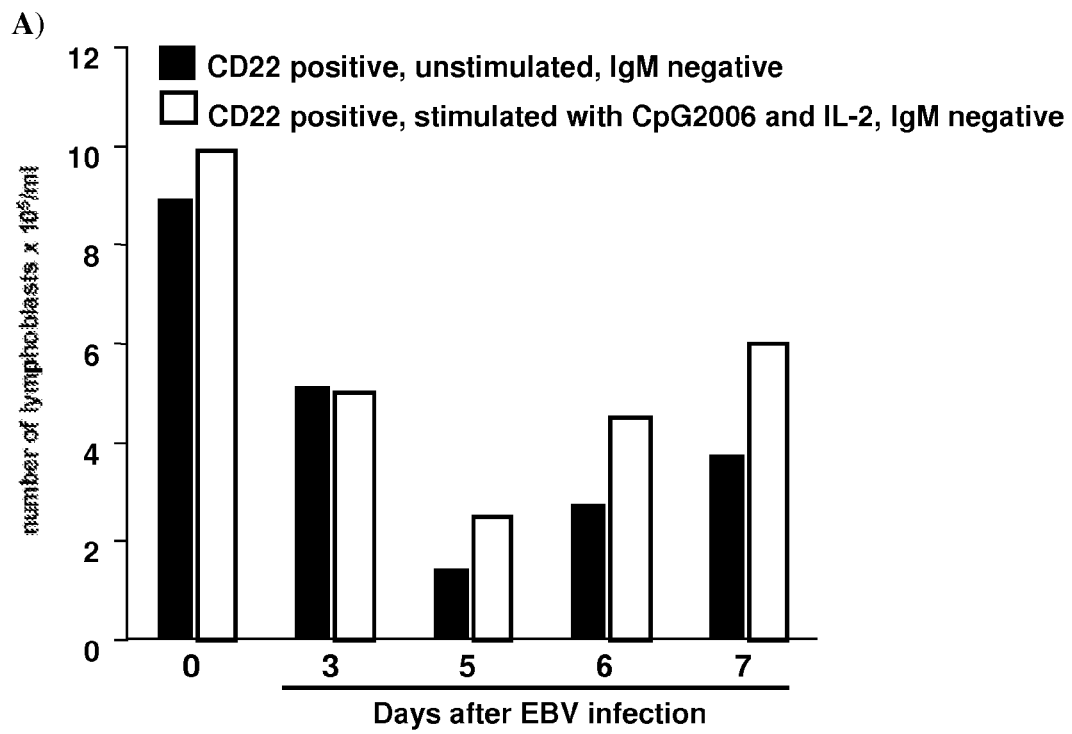
FIG. 6: Effects of the combination of CpG2006 and IL-2 on the EBV-mediated immortalization of human B cells. (A) CD22 positive B cells were purified from a pool of 5 donors by magnetic bead selection and cultured for 2 days in medium alone (black bars) or in medium containing CpG2006 (1 µg/ml) and IL-2 (1000 U/ml) (white bars). The cells were then washed and IgM positive cells were depleted by cell sorting. CD22 positive, IgM negative cells were immortalized by overnight culture with a 50% V/V of EBV-containing supernatant in the cell culture medium. The cell culture medium that contained EBV was removed and the cells were cultured in medium containing IL-2 (1000 U/ml) and irradiated allogeneic PBMCs as feeder layer for the indicated number of days. (B) CD22 positive, IgM negative B cells were purified from a pool of 5 donors by magnetic bead selection and immortalized by culture with a 30% V/V of culture medium with EBV, in the absence (black bars) or in the presence (white bars) of CpG2006 (1 µg/ml) and IL-2 (1000 U/ml), using irradiated allogeneic PBMCs as feeder layer. In both (A) and (B), the number of viable lymphoblasts (large cells) was evaluated microscopically by trypan blue dye exclusion.
Figure 6:
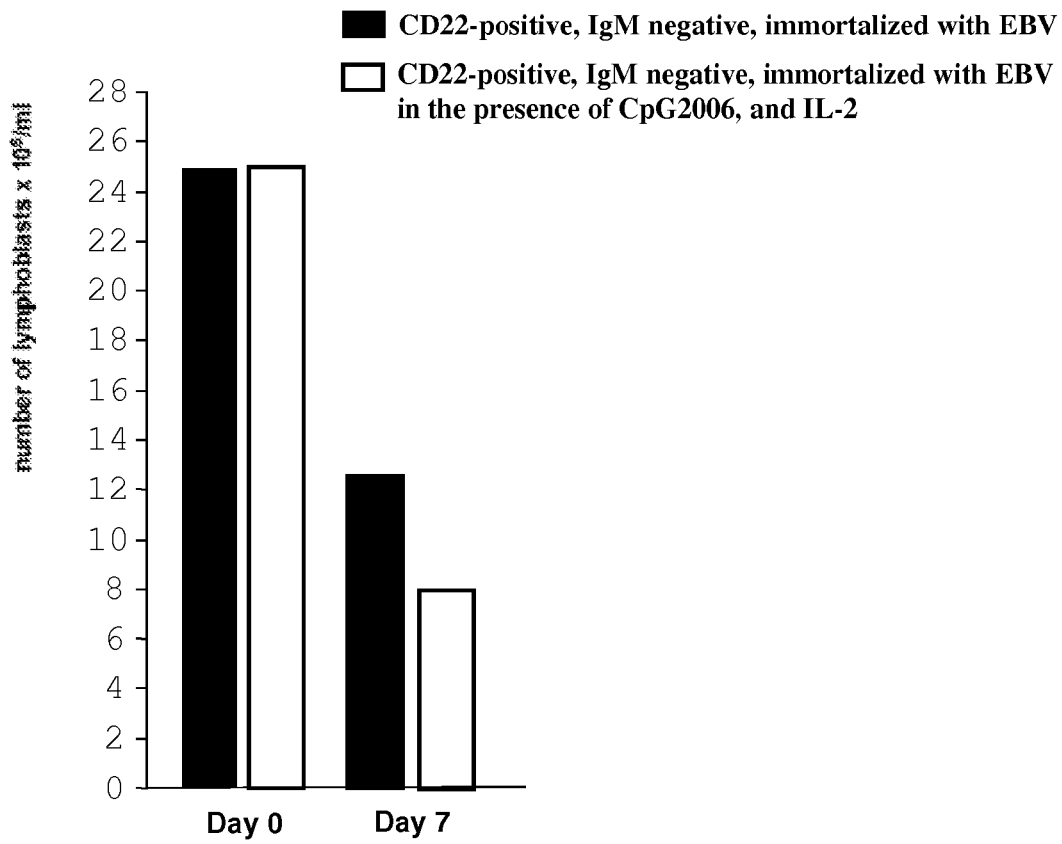

Human CD22 positive, IgM negative B cells, with or without prior stimulation with CpG2006 and IL-2, were exposed to EBV supernatant overnight, washed, and seeded with medium including IL-2 (1000 U/ml) on a feeder layer of irradiated allogeneic PBMCs. The proliferation of these cells was measured during the following days. In this way, it can be demonstrated that pretreatment of B cells with CpG2006 and IL-2 results in an enhancement in the speed and extent of resumed proliferation of B cells following EBV immortalization. This is most clearly demonstrated at day 7 following exposure to EBV supernatants, where almost 50% more cells are present in pre-stimulated cultures when compared to cells that were not pre-stimulated (FIG. 6A). This observation was confirmed also when pre-stimulated CD22 positive B cells were not additionally depleted of IgM positive cells.

Previous methods described the benefits of the use of polyclonal B cell activators during (and not only before) their immortalization using EBV supernatants, without a step for eliminating the activators from the cell culture (WO 91/09115; Hur D et al., 2005; Traggiai E et al., 2004; Tsuchiyama L et al., 1997; WO 04/076677). Thus, the number of cells in cultures of CD22 positive, IgM negative B cells that were exposed for 7 days to EBV supernatants in the presence or in the absence of CpG2006 (1 µg/ml) and IL-2 (1000 u/ml) was examined. However, the presence of CpG2006 and IL-2 during EBV immortalization resulted in decreased numbers of viable B cells, as can be concluded by counting the cells microscopically (FIG. 6B). This reduction is already significant when compared to cells exposed to EBV supernatants alone, but it is even more important when the data obtained with the separate pre-stimulation phase are considered (FIG. 6A).

These data suggest that a distinct stimulation phase in which cultures of human B cells are treated with stimulating agents (used singly or in combination, such as CpG2006 and IL-2) exerts a beneficial effect on the entire process of B cell selection and immortalization using EBV. This positive effect can be further improved by using additional specific combinations of stimulators (reduced concentrations of CpG2006 and/or IL-2, for instance) and/or by limiting the stimulation phase to a period of time (for example, between 2 and 4 days) in which the B cells show optimal proliferation activity and expression of relevant markers (such as CD21). The removal of the stimulating agents before the immortalization phase is instrumental for obtaining the best results from this method, being growth and viability of CD22 positive B cells negatively affected by the continuous and extensive presence of the stimulator agents combined with EBV supernatants.

The data presented above allows demonstrating not only the possibility to apply the method to a specific subset of human B cells determined on the basis of the expression of cell surface markers (CD21, CD23, CD24, CD27, and/or CD22, for instance), but also the feasibility to apply further selection criteria related to the antibody secreted by the B cells. In the present case, the use of technologies for eliminating cells expressing antibodies of a specific isotype (IgM) before proceeding to the immortalization.

Figure 7:
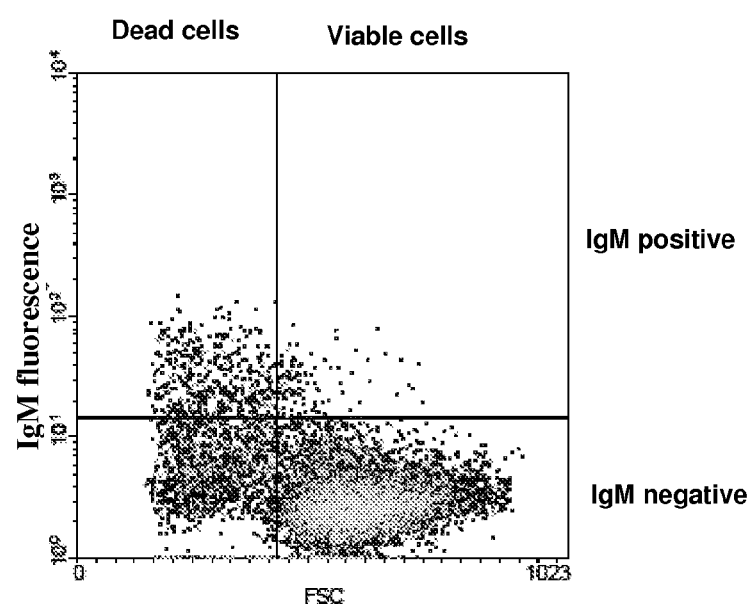
FIG. 7: Phenotype of CD22 positive, IgM negative B cells following 2 days of pre-stimulation with CpG2006 and IL-2, EBV immortalization, and culture for 10 days (with IL-2 and irradiated allogeneic PBMC feeder layer in the absence of EBV and CpG2006). (A) Ten thousands events were analyzed by FACS Dot-plot analysis where the vertical axis represents the level of IgM fluorescence and the horizontal axis indicates forward scatter (as a measure of the size of cells). The viable blast cells, with high levels of forward scatter, are all contained within the right hand quadrants. The IgM negative cells are indicated in the lower two quadrants, with viable blast cells that do not express IgM antibodies (and mostly expressing IgG antibodies) are present in the bottom right quadrant. (B) Immunodiffusion analysis performed using the supernatants of the EBV immortalized, CD22 positive, IgM negative B cells, as stimulated and selected according to (A). Spent medium was concentrated 5-fold before the assay. The assay evaluated the presence of total secreted human immunoglobulins (αhIg), human IgM (αhIgM), and human IgG (αhIgG) in the cell culture supernatant using isotype-specific antibodies.
Figure 7:
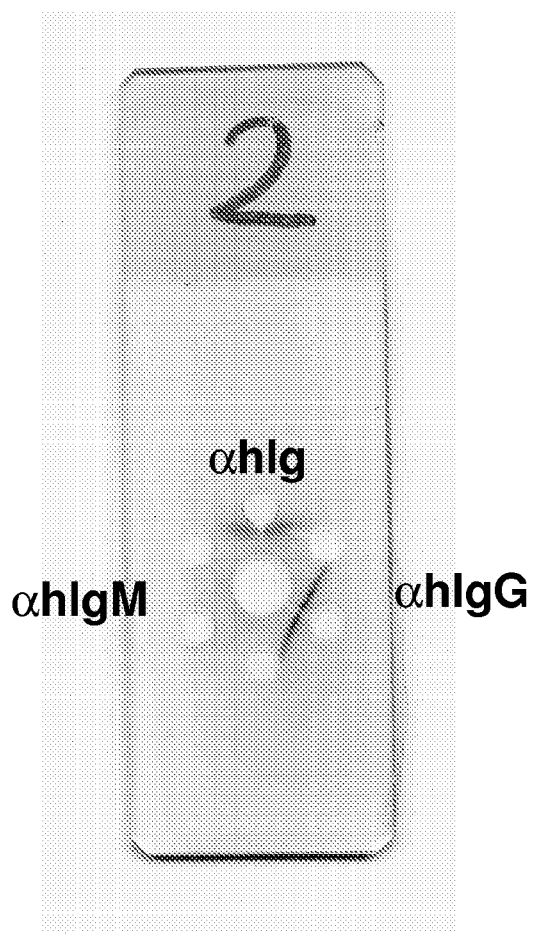

In fact, a FACS-based analysis of CD22 positive, CpG2006/IL-2-stimulated, IgM-depleted, EBV-immortalized B cells that was performed at 10 days after EBV infection confirmed that almost the totality of the viable cells (indicated by a higher forward scatter in the two right hand quadrants) continue to be IgM negative (bottom right quadrant), a phenotype that is more desirable for therapeutic antibody generation (FIG. 7A). A further demonstration that human immortalized, isotype-specific, B cell cultures can be generated and maintained using the methods of the Invention, was obtained by testing the supernatants of the B cells described above in an immunodiffusion assay, as performed in the literature by immunodiffusion (Mancini G et al., 1965), confirming that such B cells are essentially IgG-secreting cells (FIG. 7B).

This unexpected positive effect of coupling B cell specific stimulation and isotype-based B cell selection before EBV immortalization, can be further improved by including other means of B cell selection.

The efficiency of this approach can be measured on the basis of the cloning efficiency of CD22 positive, CpG2006/IL-2-stimulated, IgM negative B cells. The obtained cells are expanded in vitro in the presence of CpG2006 and IL-2 for 2-4 days, then enriched for the IgG positive subpopulation by positive or by IgM-based negative selection. The CD22 positive, IgM negative B cells are infected with EBV and cloned by limiting dilution in 96-well plates 1-4 weeks after infection. The cloning efficiency from the bulk culture can be evaluated by scoring the number of wells containing growing cells at each tested dilution of the bulk culture (e.g. 1:5, 1:10, 1:25, 1:50, 1:100, 1:200), or at each concentration of cells per well (e.g. 1, 5, 10, 20, 25, 50, 100, 200, or more cells per well).

One of the most important considerations when performing EBV immortalization is to maintain the viability of the cells to be used for subsequent cloning. This is particularly the case when attempting to identify antigen-specific B cells that may be present at a very low frequency (<1:1000) in the peripheral blood. It is well established that EBV is a polyclonal B cell stimulator, but that exposure of B cells to EBV results in an initial period of cell death in the culture (Sugimoto M et al., 2004).

Figure 8:
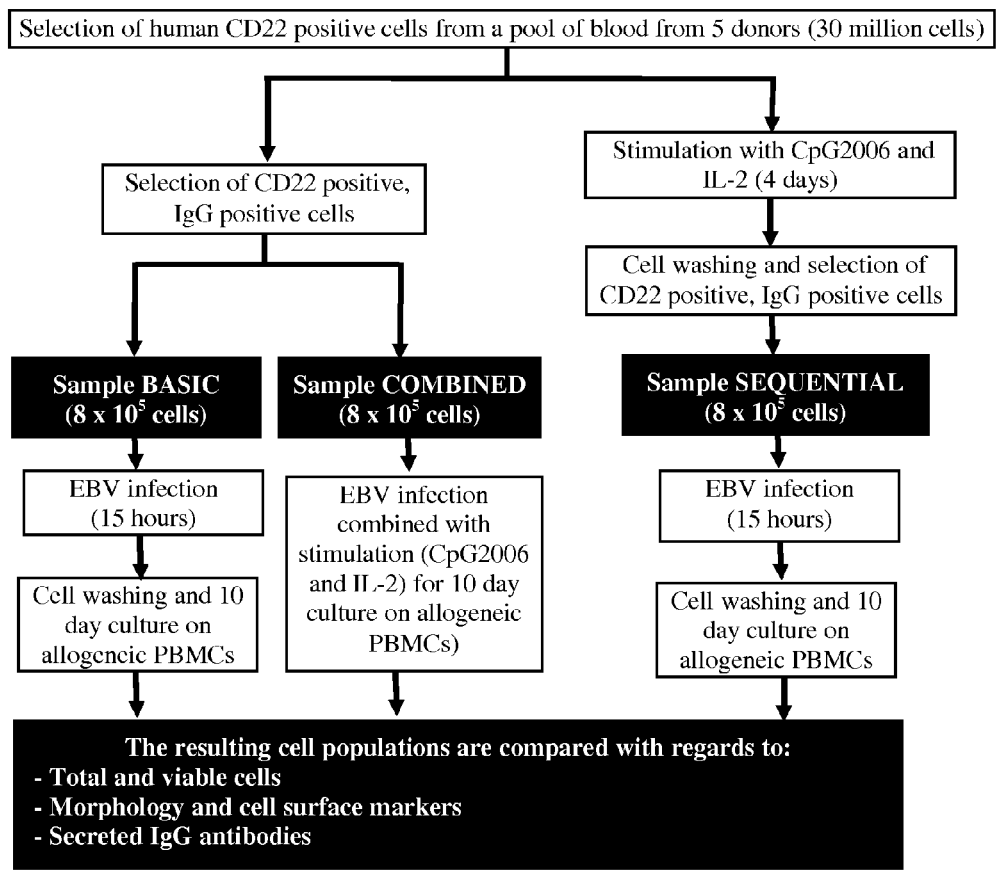
FIG. 8: Comparison of the polyclonal populations of cells obtained according to the BASIC, COMBINED, and SEQUENTIAL methods (A) overview of the procedure for preparing the polyclonal populations of cells according to the BASIC, COMBINED, and SEQUENTIAL methods. (B) The populations are compared in terms of total cell number (measured by flow cytometry) and of the fraction of viable cells (measured by propidium iodide exclusion and flow cytometry, as described in materials and methods).
Figure 8:
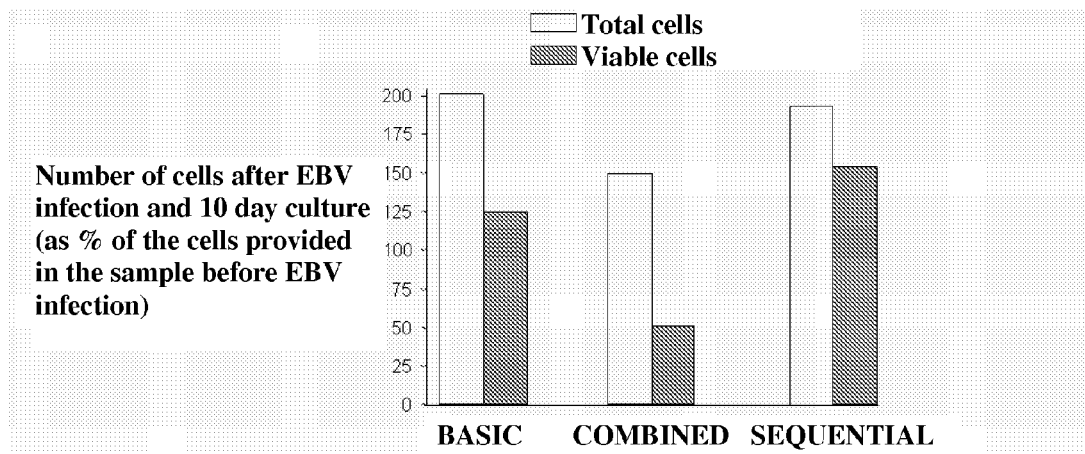

Further data in support of the Invention have been generated by comparing the outcome of three methods of EBV-mediated cell immortalization applied on the same starting population of CD22 positive peripheral blood mononuclear cells (PBMC) pooled from 5 normal donors (FIG. 8A).

In the BASIC method, a very simple approach was used in which CD22 positive, IgG positive cells were exposed only to EBV-containing supernatant for 12 hours, washed and cultured for 10 days in the appropriate cell culture media and on feeder cells. In the COMBINED method, the CD22 positive, IgG positive cells were simultaneously exposed to EBV and to polyclonal activating agents (CpG2006 and IL-2) in cell culture for 10 days, similarly to what described in the literature on the use of such compounds simultaneously (Traggiai E et al., 2004; Tsuchiyama L et al., 1997). For the SEQUENTIAL method, that is a possible way to apply the methods of the Invention, CD22 positive cells were first exposed to the combination of CpG2006 and IL-2 and washed. Then the IgG positive cells were purified and the CD22 positive, IgG positive cells exposed for 12 hours to EBV-containing supernatant, washed and cultured for 10 days, again in the appropriate cell culture media and on feeder cells.

Since the absolute number of CD22 positive, IgG positive cells were normalized for all conditions at the initiation of exposure to EBV, the data resulting from the analysis of cell cultures and supernatants measured at the end of the 10 day culture should provide a precise comparison of the three methods. In fact, both the BASIC and SEQUENTIAL methods provide an increase in the total cell number, resulting in nearly 2-fold (200%) of the starting cell number, more significant than that obtained using the COMBINED method resulting in 1.5-fold (150%). More importantly, when the number of viable cells was determined, the population of cells obtained using the SEQUENTIAL method showed an enhanced number of viable cells compared to both the BASIC method and, even more dramatically, the COMBINED method (FIG. 8B).

Then, more qualitative analysis of the populations of cells that were obtained using the three methods was performed using different criteria.

FACS analysis shows that, apart from all being populations of cells that express IgG, their composition is different, as a whole, and in particular in the area corresponding to the viable lymphoblasts that are growing and dividing (being negative for propidium iodide staining and with higher forward scatter; R2 area in FIG. 9). The population of cells that is obtained using the SEQUENTIAL method appears significantly more concentrated in this area when compared to that obtained using the BASIC method and, even more strikingly, to that obtained using the COMBINED method. Cells with higher levels of fluorescence due to the accumulation of propidium iodide, are dead or dying and both the populations obtained using the BASIC and the COMBINED methods have accumulated many more cells of this kind that will not be available for any further subcloning or screening assay (FIG. 9, left panel).

The population of viable lymhoblasts present in the samples was also analyzed for the expression of CD23, a cell surface marker that is present at a low level by most peripheral blood B cells but whose expression is commonly enhanced by activation (Azim T and Crawford D, 1988). It is important to put in evidence such index since a direct correlation between CD23 expression and IgG secretion has been demonstrated in populations of EBV immortalized human B cells (Wroblewski J et al., 2002). The level of expression of CD23 is shown on a log scale on the horizontal axis and the relative number of cells expressing a given amount of CD23 is shown on the vertical axis (FIG. 9, right panel). It is evident that both BASIC and SEQUENTIAL methods induce a high level of CD23 expression in a much larger proportion of cells than that observed in the population of cells obtained with the COMBINED method, where very few cells expressing high levels of CD23 are evident and an accumulation of cells that are negative or low for CD23 expression occurs.

The qualitative analysis of the population of cells produced according to the three methods described above from the same pool of primary B cells, provides important information regarding the specific positive features of the methods of the Invention. In fact, it has been confirmed that the separation of EBV immortalization from polyclonal stimulation, instead of having the cells exposed to the two types of agents simultaneously, provides a population of cells with improved viability, CD23 expression, and proliferation potential. Moreover, the FACS analysis shows that the methods of the Invention provide a population of cells that, in some aspects, resembles a population of cells obtained by BASIC method, but having a higher frequency of viable, blast-like cells (see FIG. 9, left panel).

This aspect seems to have additional important and surprising effects on a major element for comparing the different methods: the amount of IgG that the populations of cells accumulate in the cell culture supernatant in a relatively short period of cell culture (8-10 days). It is evident that any improvement in the levels of IgG secretion in the supernatants from these cultures affects positively their screening for antibodies, since it may shorten the period of time for isolating oligoclonal or monoclonal cell cultures expressing such antibodies.

Figure 10:
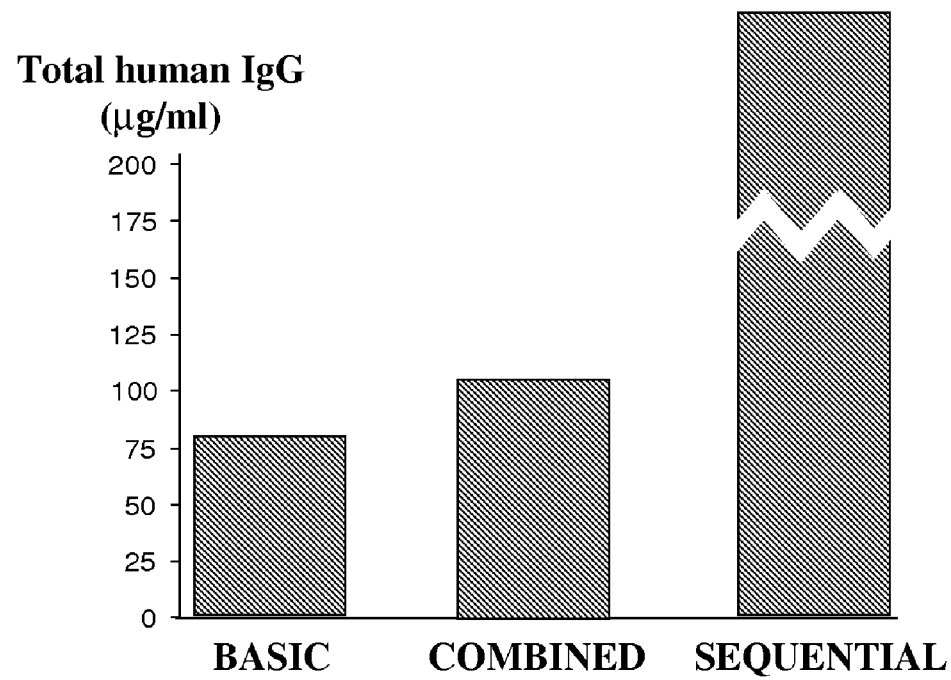
FIG. 10: Analysis of IgG secretion in cell cultures that were prepared using the BASIC, COMBINED or SEQUENTIAL methods. The cell-free supernatants were harvested after the 10 day culture (see FIG. 8A) and IgG concentration was measured in serial dilutions of supernatants using a total human IgG ELISA commercial kit. The absolute amount of IgG in each supernatant was measured by comparison to a standard curve of purified human IgG provided by the ELISA kit manufacturer, where the linear range reached a plateau at ~150 µg/ml. All dilutions of supernatant from the sequential process resulted in measurements beyond the linear range of the standard curve, and it can be extrapolated from these measurements only that the concentration of total IgG is beyond 200 µg/ml. For this reason, the result is depicted with a hashed line.

The comparison of the total IgG that is accumulated in cell cultures obtained using the three methods on the same initial population of cells, which has been also normalized quantitatively before the exposure to EBV, further confirms the advantages of the SEQUENTIAL method, based on the methods of the Invention. In fact, if the BASIC and COMBINED methods provide a similar concentration of total IgG (80-100 µg/ml), the supernatant of cells resulting from the SEQUENTIAL method provided cells expressing total IgG at a level well beyond the linear range of the ELISA kit (~150 µg/ml) for all dilution-factors tested (FIG. 10A).

Thus, not only a polyclonal population of cells obtained according to the methods of the Invention is made of cells actively proliferating and viable, but also express levels of total IgG that are sufficient to perform many different screening assays, without any possible interference of compounds such as polyclonal stimulating agents, finally accelerating the process for determining the presence of cells expressing IgG antibodies of interest.

Example 3

Selection, Stimulation, Immortalization, and Screening of Human B Cells Expressing IgG Antibodies Binding or Neutralizing Therapeutic Targets Materials & Methods
Generation of Human Immortalized B cells expressing IgG Antibodies The overview of the procedure is provided in FIG. 11. The conditions and the means were those defined in Examples 1 and 2
CMV Microneutralisation Assay Human embryo lung fibroblasts (HELF) are plated (2.0-2.5×10$^4$/well) onto flat-bottom wells of a 96-well plate in 100 µl of Eagle's minimal essential medium (MEM) supplemented with 10% fetal bovine serum (FCS), 1 mM sodium pyruvate (NaP), 2 mM glutamine, 100 U/ml penicillin and 100 µg/ml streptomycin (GPS) and cultured for 24 hours at 37° C.

Fifty µl of supernatant from each B cell culture/clone are incubated with the laboratory strain CMV (AD169; 500 pfu in 50 µl of MEM with 5% FCS; total volume of the mixture is 100 µl) in round-bottom wells of a 96-well plate for 1 hour at 37° C. The medium from HELF cultures are discarded and replaced with the viral mixture. The plates are then centrifuged at 2000 g for 30 minutes and incubated for 90 minutes at 37° C. in $CO_2$. The medium is then discarded, 100 µl of growth medium are added and the cultures are maintained in the incubator for further 72 hours.

The effect of B cell supernatants on CMV infecting activity is measured by staining human CMV Intermediate Early Antigen (IEA) by indirect immunoperoxidase staining of HELF cells. The cell monolayers are fixed with 50% acetone and 50% methanol (stored at −20° C.) solution for 1 minute at room temperature (RT) then washed with PBS. The cells are permeabilized in 0.1% Triton X-100 in PBS with 1% $H_2O_2$, 5 minutes on ice then washed with PBS. Endogenous peroxidase is blocked with PBS with 50% methanol and 0.6% $H_2O_2$, minutes at RT in the dark then washed with PBS. Fifty µl of Protein Blocking Agent (Ultra Tech HRP 500-600 Test; Streptavidin-Biotin Universal Detection System; PN IM2391) was added for 10 minutes at RT, then washed with PBS. Optimal concentrations of primary antibody (anti-human CMV IEA; Argene Biosoft; Ref No. 11-003) are added to wells for 60 minutes at RT. The wells are washed, then 50 µl of Biotinylated Secondary Antibody (Ultra Tech HRP 500-600 Test; Streptavidin-Biotin Universal Detection System; Ref. No. PN IM2391) are added to wells for 10 minutes at RT. The wells are then extensively washed with PBS and DAB substrate (MERCK; ref. no. 1.02924.0001) in 0.1% $H_2O_2$ added for 30-45 minutes at RT in the dark. The reaction is stopped by dilution with PBS and IEA positive nuclei are counted microscopically.

The B cell supernatants were also tested using human umbilical vein endothelial cells (HUVEC) and the clinical CMV strain VR1814.

As a negative control, B cell supernatants containing irrelevant IgG antibodies were used. As positive control, a commercial preparation of human IgG antibodies, derived from the serum of patients and specific for CMV (Cytotect; Biotest) was used (using progressive dilutions, starting at 125 µg/ml).
ELISA-Based Assays for Detecting CMV Binding Proteins A first assay was performed using a commercial quantitative enzyme-linked immunosorbent assay (ELISA) for the detection of specific IgG antibodies binding to a CMV protein extract in human serum or plasma. The commercial ELISA kit (BEIA CMV IgG Quant Kit; Bouty) has been used according to manufacturer's instructions and validated with a commercial mixture of IgG antibodies specific for CMV (Cytotect; Biotest) used at 50 U/ml.

Briefly, breakable strips covered with an inactivated CMV protein mixture (derived from the laboratory strain AD169) are placed into microplates and incubated with B cell supernatants diluted 1:81 (10 µl of supernatants added to 800 µl of sample diluents of the BEIA system), and the plate incubated at room temperature for 30 minutes. After a washing cycle, pre-diluted monoclonal anti-human IgG antibody conjugated with horseradish peroxidase (100 µl) is added and plate is incubated at room temperature for a further 30 minutes. After a second washing cycle, pre-diluted substrate-TMB solution (100 µl) is added and the plate is incubated at room temperature for additional 15 minutes. The reaction is stopped using the Stop Solution (100 µl/well) and the optical density is measured in bichromatism at 450/620 nanometers.

Additional assays were performed using ELISA established in the laboratory using specific peptides or recombinant CMV proteins immobilized on solid surfaces.

Recombinant CMV Antigen gB immunodominant region was produced as a recombinant fusion protein, together with Glutathione-S-Transferase (GST) and purified by affinity (GST-affinity purification; Biodesign Int, cat. No. R18102), or as a peptide. Recombinant CMV Antigen gH immunodominant region (VR1814 strain) was as well produced in $E.$ $coli$ and purified from the bacterial cell lysate on the basis of GST affinity. These ELISA were performed by applying a common ELISA protocol in a 96-well format with minor modifications. Briefly, the antigen is diluted in PBS at 2 µg/ml in PBS and 50 µl of this protein solution is used for coating each the well of an EIA polystyrene plate (Nunc, cat. No. 469949) by an overnight incubation at 4° C. The protein solution is eliminated and the wells are washed four times with 100 µl of Wash Buffer (PBS containing 0.05% of Tween 20). A treatment for blocking unspecific binding was performed by then dispensing 100 µl of PBS containing 1% of milk in each well and incubating the plate for 1 hour at 37° C. After performing four washing cycles with 150 µl of Wash Buffer, a 50 µl aliquot of cell culture supernatant from cell cultures was dispensed in each well, using as negative control 50 µl/well of the cell culture medium. After an incubation of 2 hours at 37° C., the plate was washed four times with 150 µl of Wash Buffer before dispensing 50 µl of a horseradish peroxidase-labelled anti-human IgG antibody (Fc-specific, goat anti-human IgG antibody; Sigma, cat. No. A0170) that has been diluted 1:30000 in Wash Buffer in each well. After an incubation of 1 hour at room temperature, the plate was washed four times with 150 µl of Wash Buffer before dispensing 50 µl/well of substrate-TMB solution (3,3',5,5' Tetramethylbenzidine; Sigma, cat no. T0440). After an incubation of 30 minutes at room temperature, the chromogenic reaction was stopped with 100 µl/well of Stop Solution (1N Sulphuric acid) and the optical density was measured at 450 nm.

ELISA-Based, HSP60 Binding Assay

The ELISA for detecting antibodies binding HSP-60 was established using EIA/RIA well strips that are coated with 50 ml of recombinant human HSP60 protein (Stressgen) diluted in NaHCO3 0.1M pH 9.6 at 1 µg/ml, and kept overnight at room temperature. Strips are washed 3 times with PBS with 0.05% Tween-20 pH 7.4 and non specific binding sites are blocked with PBS with 1% BSA and 5% sucrose for 30 minutes at room temperature. After 4 washes, strips were incubated for 3 hours at room temperature with a panel of primary antibodies: an anti-human HSP60 (diluted in PBS with 1% BSA at 5 or 10·g/ml; Santa Cruz Biologicals), a mouse IgG isotype negative control (5·g/ml in PBS with 1% BSA), an unrelated human recombinant IgG antibody (Herceptin, 5 µg/ml), cell culture medium only, and supernatants from EBV-immortalized human IgG secreting B cells. After 4 washes, strips were incubated with Horseradish Peroxidase-conjugated anti-mouse IgG or anti-human IgG (Dako) diluted in PBS with 1% BSA for 1 hour at room temperature. After 4 washes, substrate-TMB solution is added to the strips and allowed to develop a color reaction at room temperature. Plate is read at 450 nm.

Results

The methods of the Invention have been tested on human B cells obtained from donors whose blood has proved to be containing antibodies binding and/or neutralizing human viruses, in particular human cytomegalovirus (CMV), a beta-herpesvirus causing birth defects and highly pathogenic for immunocompromised patients (Landolfo S et al., 2003).

CMV is a good example of a viral target of clinical interest that can be neutralized by antibodies naturally secreted by human B cells selected, stimulated, and immortalized according to the methods of the Invention, as briefly summarized in FIG. 11. Moreover, amongst the different therapeutic strategies for CMV, the administration of intravenous CMV immune globulin (commercialized under the name of Cytotect or CytoGam) represents a solution only partially satisfactory for blocking CMV infection, in particular in immunocompromised patients where potent antivirals are often co-administered (Bonaros N E et al., 2004; Kocher A A et al., 2003; Kruger R M et al., 2003). These preparations are characterized for clinical uses but are simply derived from human pooled plasma with high titers of anti-CMV antibodies. The treatment of CMV infections would benefit from having more potent preparations comprising purified human monoclonal antibodies obtained by the expression in mammalian cells approved for regulatory purposes.

Human B cells expressing CMV-neutralizing antibodies can be obtained from donors selected on the basis of one or more immunological screening assays (such as immunoblot, ELISA or ELISPOT) or on antigen microarrays, that are available from commercial sources (Sorin Biomedica, Italy; BioMerieux, France).

Human B cells were isolated from the clinical samples of selected donors providing higher titers of anti-CMV antibodies in blood, as measured by ELISA, ELISPOT or neutralization assay. The cells were then subjected to the methods of Invention (FIG. 11). The resulting population of CD22 positive, IgM negative, EBV-immortalized, human B cells were screened using, directly or indirectly, the supernatants of cell cultures derived by subcloning the original population for detecting those containing CMV-neutralizing and/or CMV-binding IgG antibodies. The original B cells producing these antibodies can be then isolated in subsequent subcloning steps, at the scope of cloning and sequencing the DNA encoding for these antibodies.

Figure 12:
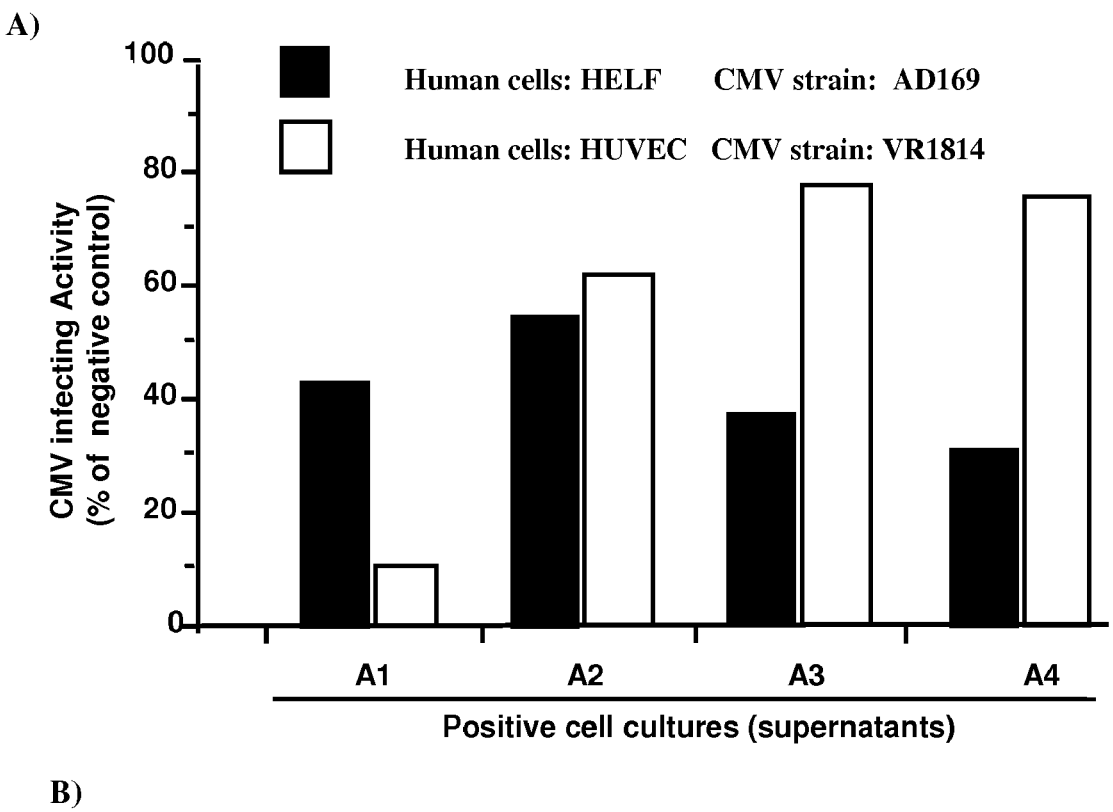
FIG. 12: Identification of EBV-immortalized, IgG-secreting human B cell cultures that have been obtained using the process streamlined in FIG. 11 for isolating IgG antibodies having different activities. (A) Supernatants from cultures of EBV immortalized B cells from a CMV seropositive donor were incubated with the indicated isolates of human cytomegalovirus (CMV) and then added to the indicated human cells. AD169 is a laboratory strain of human CMV. VR1814 is a clinical isolate of human CMV. HELF are human embryonic lung fibroblasts and HUVEC are human umbilical vein endothelial cells. The neutralizing activity of selected, human IgG antibody containing cell culture supernatants is expressed in term of decreased CMV infecting activity (representative of at least two assays). The data were obtained by measuring immunohistological staining for CMV immediate early antigen (IEA). The negative control was cell culture medium only. (B) Supernatants from EBV immortalized human B cell cultures were pooled (5 supernatants/pool) and tested in an ELISA to detect human IgG antibodies binding to human HSP60 protein. Data indicates the mean values of duplicate wells. The line indicates the reference value (3 times the levels observed with cell culture medium alone (RPMI-1640 and 10% FCS). The positive control samples (a commercial mouse anti-human antibody to HSP60, at indicated concentrations) and a negative control sample (mIgG, a non-specific mouse IgG) revealed with anti-mouse IgG. All other control samples (two negative controls with medium only or an unrelated human IgG, hIgG) and the samples containing the supernatants of the cell cultures were revealed with a commercial anti-human IgG antibody.
Figure 12:
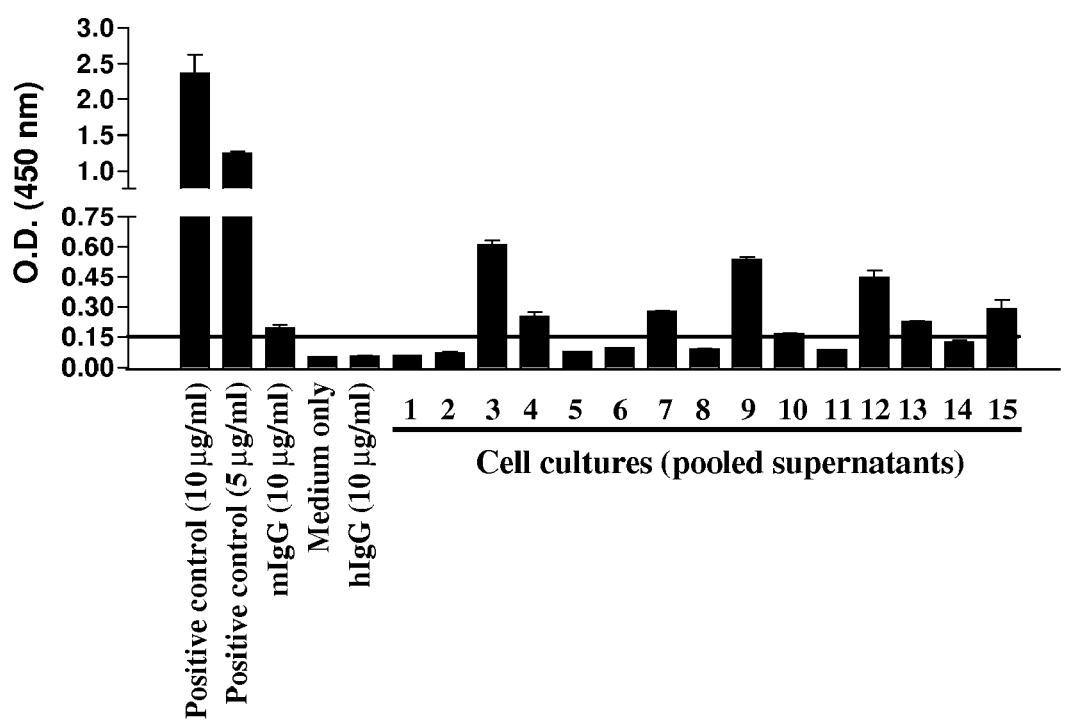

A first type of primary screening assay was applied on over 400 subcultures in 96-well plates, each well containing approximately a hundred B cells. The supernatants from these wells were screened in a CMV microneutralisation assay for the ability to block the infection of human cells with a laboratory strain (AD169) or a clinical strain (VR1814) of human CMV. Four out of 453 B cell cultures screened showed significant neutralizing activity in repeated experiments using a laboratory CMV isolate and one in particular showed neutralization of a clinical CMV isolate in repeat assays (FIG. 12A).

A second type of primary screening assay was applied on a population of B cells obtained from a different CMV-seropositive donor and again subjected to the methods of the Invention. In this case, the CMV-specific reactivity was detected using a commercially available ELISA that is more sensitive. CMV positive subcultures, such as those characterized above, can be used to start the subcloning process at the scope of identifying the cell cultures and sequences corresponding to the antibodies responsible of the CMV-neutralizing or binding activities detected using the primary screening assays.

These antibodies, as purified preparations from human B cell supernatants or expressed as recombinant proteins, can be further validated using organ- or cell-based in vitro assays known in the literature (Reinhardt B et al., 2003; Forthal D N et al., 2001; Goodrum F D et al., 2002). Moreover, relevant pre-clinical tests can be made in CMV-infected animals, in particular in models where human host cells can be transplanted into immunocompromised rodents (Gosselin J et al., 2005; Thomsen M et al., 2005). The CMV antigen/epitope recognized by these antibodies can be identified by different in vitro assays based, for example, on ELISA or Western Blot using CMV-specific truncated proteins or synthetic peptides, or on competition with other CMV-specific antibodies whose antigen/epitope is known (Greijer A et al., 1999; Schoppel K et al., 1996; Ohlin M et al., 1993).

Further screening assays can be performed using cell culture supernatants tested for the neutralization or the binding of human cytomegalovirus. In fact, the availability of a large repertoire of IgG-secreting cells allows the identification of a number of human IgG having binding specificity for distinct CMV epitopes or antigens that may be associated to CMV infection. For example it is known that the blood of atherosclerosis patients contains high levels of antibodies recognizing a fragment of the human heat-shock protein 60 (HSP60) that is similar to CMV proteins. In particular, one of these proteins called US28 is expressed on surface of endothelial cells and antibodies binding this protein can induce endothelial-cell apoptosis, suggesting the idea that CMV infection may trigger an autoimmune response implicated in atherosclerosis pathogenesis (Bason C et al., 2003).

Therefore, 65 pools of cell culture supernatants (each containing supernatant from 5 wells of the EBV-immortalized cells produced starting from primary B cells obtained from a CMV-seropositive individual) were screened for HSP60 immunoreactivity using an ELISA making use of recombinant human HSP60. Six pools showed a statistically significant reactivity 3 times above background on the ELISA in repeated experiments (FIG. 12B). These cultures of immortalized antibody-secreting cells can be subcloned in pools of cells, repeating the screening and subcloning process until cell cultures secreting human monoclonal IgG antibodies that bind human HSP60 are isolated.

A second type of primary screening assay was applied on a population of B cells obtained from a specific CMV-seropositive donor and again subjected to the methods of the Invention. In this case, the CMV-specific reactivity was detected in parallel using a panel of different tests at the scope of selecting, from a single population of primary B cells, oligoclonal or monoclonal populations of immortalized cells each expressing antibodies against distinct CMV-specific epitopes, and thus providing an overall representation of the immune reaction to CMV infection in an individual (FIG. 13).

The polyclonal population of EBV-immortalized cells was divided in approx. 4000 pools for establishing cell cultures, each containing statistically 20 cells, in 96-well plates, wherein each well contain an oligoclonal population of cells. However, given the low frequency of cells producing antibodies specific for a defined antigen, any of these cell cultures for which a CMV-specific IgG is detected in the supernatant is likely to be a monoclonal cell culture expressing a human monoclonal antibody.

The initial tests evaluated the CMV binding properties of the antibodies produced by the oligoclonal/monoclonal cell culture that are specific for either a mixture of CMV proteins or specific antigens known to be recognized by CMV neutralizing antibodies. Then, those being positive to at least one of these assays, were further evaluated in a CMV microneutralization assay.

Two specific CMV antigens were chosen for the initial screening of the oligoclonal/monoclonal populations of cells: the envelope glycoproteins gB and gH. These proteins, which play crucial roles in both viral attachment and fusion, are the targets for human CMV-neutralizing antibodies for which more detailed information are available. Sera from seropositive individuals as well as monoclonal antibodies directed against these glycoproteins inhibit HCMV infection of cell cultures in vitro. The effective role of antibodies directed against gB and gH in contributing to the virus-neutralizing capacity of human sera has been clearly shown by the correlation between anti-gB and anti-gH titers and overall neutralizing activity of convalescent human sera, as well as by the significant drop of the sera neutralizing capacity after adsorption of gB- and gH-specific antibodies. (reviewed In Cytomegaloviruses. Molecular Biology and Immunology. Reddehase, M. (ed.) Norfolk: Caister Academic Press (2006), and in particular Boehme K and Compton T p. 111-130, Mach M pp. 265-283).

As summarized in FIG. 13, using the oligoclonal cell cultures in which cells were actively proliferating (approximately 35% of the total wells in which cells were seeded), it was possible to identify wells that contained IgG reactive with CMV protein at least in one of assays specific for defined CMV proteins (gB- or gH-ELISA) or for a total CMV protein extract (BEIA CMV ELISA). In particular, some wells contained human IgG that neutralize CMV infection in vitro.

Figure 14:
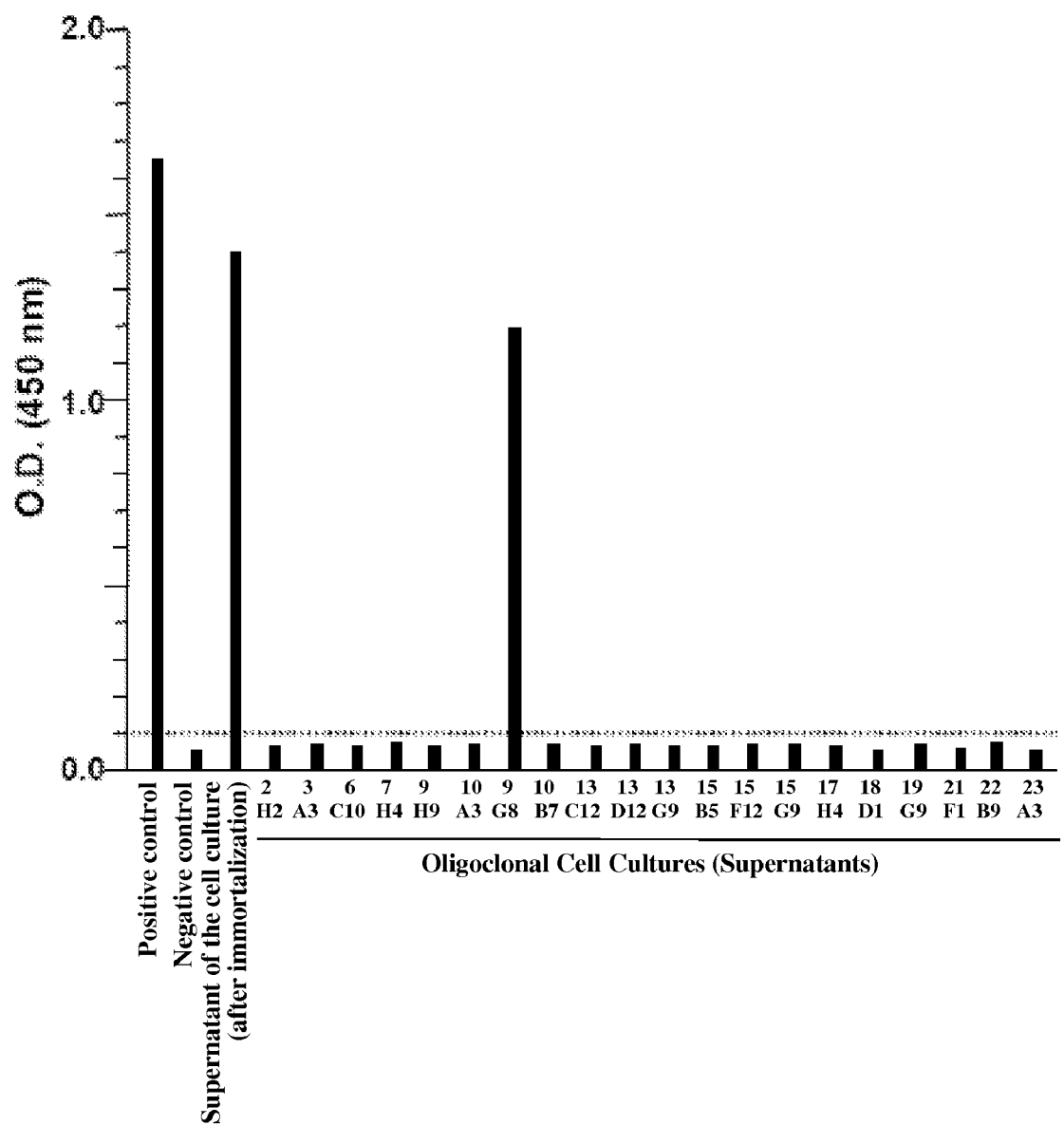
FIG. 14: Identification of EBV-immortalized, IgG-secreting human B cell cultures that have been obtained using the process streamlined in FIG. 13 for isolating IgG antibodies binding CMV proteins. CD22 positive, IgG positive B cells from a CMV donor having neutralizing activity in the serum were prepared using the SEQUENTIAL protocol as described in Example 2. The supernatant from the day cell culture (CMV5 bulk culture) generated by using the resulting population was collected and stored at 4° C. and tested with the BEIA-CMV ELISA kit described in materials and methods. Then, the cell culture was divided at 20 cells/well into 96-well plates and cultured in the presence of irradiated allogeneic PBMC feeder cells, CpG2006, and IL-2 for 4 weeks. The cell-free supernatants, which were prepared from wells containing populations of cells actively proliferating, were screened with the BEIA-CMV ELISA kit. The positive control (calibrator 2, 10 AU/ml) was included with the ELISA kit and used according to the manufacturer's instructions. The negative control was medium only (IMDM with L-glutamine, NEAE, 10% FCS, CpG2006, and IL-2). The results from 20 representative cell cultures are shown. The horizontal line shows the 2-fold cut-off value for the assay.

Amongst the eight oligoclonal cell cultures that were positive in the BEIA CMV ELISA only, the well named 9G8 contained a human IgG that was highly positive for CMV reactivity (FIG. 14). A sample containing ten thousand cells from well 9G8 was used to generate cDNA and sequences for variable regions of heavy and light chains of human IgG were specifically amplified by PCR. The products of the amplification reactions were cloned and sequenced and confirmed that 9G8 is a monoclonal cell culture secreting a novel human IgG binding to CMV having specific variable regions (FIG. 15). The DNA encoding for the variable region of this antibody also were used to determine the specific CDR sequences that, alone or in the combination provided by 9G8, can be used to generate antibodies binding to CMV.

Thus, a process comprising the methods of the Invention for immortalizing antibody-secreting cells can allow the identification of novel VH and VL sequences from oligoclonal cell cultures directly generated from the polyclonal population of cells that has been immortalized. Antibodies such as 9G8, or any protein containing one or more CDRs of this antibody (e.g. HCDR3 only; HCDR1, HCDR2, and HCDR3; LCDR1, LCDR2, and LCDR3) can be useful in CMV-related clinical and experimental applications, in particular for CMV detection in biological samples.

The methods of the Invention were also used to immortalize primary B cells obtained from HIV-1, HSV-1 and/or HSV-2 seropositive individuals.

For example, six HSV-1/HIV-1 seropositive individuals was selected because their plasma showed high titers of IgG antibodies binding HSV-1 proteins using a commercial ELISA kit (Bouty BEIA HSV-1; cat no. 20921). PBMCs from these individuals were pooled and immortalized using the same method described above for the PBMCs obtained from the donor CMV5.

The initial 70 million PBMCs lead to a population of 1.9 million CD22 positive, IgM negative cells that still secreted an amount of HSV-1 specific IgG antibodies sufficient to be detected in the supernatant of the cell culture not only using the ELISA kit but also using an in vitro assay for detecting antibodies neutralizing HSV-1 infection that is based on null mutant virus in which the gC coding sequence was replaced by the lacZ gene (Laquerre S et al., 1998).

This polyclonal population of cells was, in part, used in screening assays for identifying cells secreting the antibodies having the HSV-1 neutralizing activity, by seeding hundreds of oligoclonal cell cultures, each containing statistically 50-100 cells, immediately after the preparation of the cell culture. In addition, aliquots of cell culture obtained after the immortalization were frozen in vials, as commonly done with established mammalian cell lines. Some of these vials were thawed after some months, the cells were cultured for a few days as the initial polyclonal cell culture, and then used for preparing thousands of oligoclonal cell cultures, each containing statistically 5 cells.

The HSV-1 neutralization assay was performed in both types of oligoclonal cell cultures (i.e. obtained by immediately seeding 50-100 cell per well or obtained by seeding 5 cell per well after thawing vials containing aliquots of the original polyclonal population of cells) and both processes lead to the identification of oligoclonal cell cultures expressing human IgG antibodies that neutralize in vitro HSV-1.

In particular, cells that secrete HSV-1 neutralizing antibodies obtained from the latter process were identified in more than 20 of such oligoclonal cell cultures. Even though the antibodies may prove to be identical in several of these cell cultures, the large number of positive wells and the possibility to directly identify the sequences of such antibodies by RT-PCR technology provide means to test many alternative oligoclonal cell cultures (possibly growing at different speeds) for later selection. In fact, not only the sequence of the antibodies can be identified and characterized, but the monoclonal antibodies of interest can be directly purified for testing the activity without the need to clone and express them as recombinant proteins, accelerating the identification of human monoclonal antibodies of most interest.

CONCLUSIONS

The results presented in the Examples show the multiple advantages of the methods of the Invention and significant improvements over the prior art.

The appropriate sequence of selection, stimulation, and immortalization steps provides particularly useful polyclonal populations of cells that, being isolated on the basis of the isotype but independently from the specific antigen-binding properties of the antibodies secreted by them, can be used for detecting antibodies having different properties from the cells obtained from a single donor, or pools of donors.

In fact, the methods of the Invention provide polyclonal, oligoclonal or monoclonal populations of cells that can be screened and selected using different criteria that are applied in parallel or serially. As shown in Example 2, the diversity of the antibody repertoire in a subject is captured by the methods of the Invention in a manner that a large number of viable and proliferating cells that secrete antibodies at high levels, suitable for extensive screening analysis, is provided. Moreover, the more uniform composition of the resulting population of cells allows access, without the need for additional selection or sorting of the cells, to an extremely wide (if not complete) panel of antibody diversity that is provided by a donor in an unbiased manner. As shown in the consecutive screening for anti-CMV and anti-HSP60, if a specific assay is performed on serum to make the choice of the donor for the cells to be immortalized, the resulting population of cells can be later used for dissecting the immune response in search for antibodies having a large spectrum of properties.

Moreover, it is possible to directly generate and make use of cell cultures seeded at very low cell density for the identification of monoclonal antibodies. The resulting cell cultures can also be maintained and screened in parallel either for applying different cell culture conditions (e.g. feeder cells, medium, growth factors) or for testing a panel of antigens and biological activities (as shown for the cells obtained from donor CMV5), but always starting from a single population of cells.

Finally, this approach is suitable for generating polyclonal populations of immortalized antibody-secreting cells that can be used for both performing a selection amongst hundreds or thousands of oligoclonal cell cultures in an automated manner, and for generating a series of vials to be frozen, each containing an aliquot of the population of cells obtained by the methods of the Invention.

In particular, these cells can be considered as a library of antibody-secreting cells that can be thawed and tested as desired, as shown in the example making use of cells obtained from an HSV-1 seropositive donor, at the scope of analyzing more extensively, or re-analyzing, the population of immortalized cells for the desired antibody specificity. Thus the identification and the production of monoclonal antibodies having the desired properties can be achieved even for targets that were not considered (or not even known) when donor was chosen or when the populations of cells were immortalized and stored in frozen aliquots.

REFERENCES

Abel K et al., Clin Diagn Lab Immunol. 2005, 12: 606-21.
Akira S and Takeda K, Nat Rev Immunol. 2004; 4: 499-511.
Aldrich T L et al., Biotechnol Prog. 2003, 19: 1433-8.
Ambach A et al., Mol. Immunol. 2004, 40: 1307-14.
Azim T and Crawford D. Int J. Cancer. 1988, 42: 23-8.
Banchereau J and Rousset, F. Adv Immunol. 1992, 52: 125-262.
Bason C et al., Lancet. 2003, 362: 1971-7.
Bass H and Darke C, Cell Prolif. 2004, 37:443-4.
Bernasconi N et al., Science 2002, 298: 2199-2202.
Bernasconi N et al., Blood 2003, 101: 4500-4504.
Bianchi A and McGrew J. Biotechnol Bioeng. 2003, 84: 439-44.
Bishop G A and Busch L K, Microbes Infect. 2002, 4: 853-7.
Bohm E et al., Biotechnol Bioeng. 2004, 88:699-706.
Bonaros N E et al., Transplantation. 2004, 77: 890-7.
Borrebaeck C et al., PNAS 1988; 85: 3995-9.
Borrebaeck C, J Immunol Meth 1989, 123: 157-165.
Borst J et al., Curr Opin Immunol. 2005, 17: 275-81.
Borth N, Biotechnol Bioeng 2002, 77: 118.
Boyd A and Fecondo J, Immunol Cell Biol. 1988; 66: 159-165.
Bourke E et al., Blood. 2003, 102: 956-63.
Bradbury A et al., Trends Biotechnol. 2003, 21:275-81 and 312-7
Bron D et al., PNAS 1984; 81: 3214-7.
Butel J, Carcinogenesis. 2000; 21: 405-26.
Butler M, Appl Microbiol Biotechnol. 2005, 68:283-91.
Carsetti R, Methods Mol. Biol. 2004, 271: 25-35.
Carter P, Nat Rev Immunol. 2006, 6: 343-57.
Casali P et al., Science. 1986, 234:476-9.
Chambers R, Curr Opin Chem. Biol. 2005, 9:46-50.
Chan M et al., J Immunol 1986, 136:106-112.
Chapman A P et al., Nat. Biotechnol. 1999, 17: 780-3.
Chardes T et al., FEBS Lett. 1999, 452: 386-94.
Chatenoud L, Methods Mol. Med. 2005, 109: 297-328.
Chen C et al., J Surg Res. 2001, 100: 166-70.
Chen K et al., Biotechnol Bioeng. 2001, 72:55-61.
Coban C et al., J Exp Med. 2005, 201: 19-25.
Cognasse F. et al., Clin Chem Lab Med. 2005, 43:22-31.
Cole S et al., Mol Cell Bioch 1984, 62: 109-120.
Craxton A et al., Blood. 2003, 101: 4464-71.
Crotty S and Ahmed R. Semin Immunol. 2004, 16: 197-203.

Crotty S et al., J Immunol Meth 2004, 286: 111-122.
Damania B, Nat Rev Microbiol. 2004, 2: 656-68.
Danczyk R et al., Biotechnol Bioeng. 2003, 20, 84:215-23.
Dattamajumdar A K et al., Immunogenetics. 1996; 43:141-51.
Davenport C et al., FEMS Microbiol Immunol. 1992, 4: 335-43.
Dessain S K et al., J Immunol Methods. 2004, 291: 109-22.
Dinnis D and James D, Biotechnol Bioeng. 2005, 91: 180-9.
Dunman P M and Nesin M, Curr Opin Pharmacol. 2003, 3: 486-96.
Eaton-Bassiri A et al., Infect Immun. 2004; 72: 7202-11.
Essono S et al., J Immunol Methods. 2003; 279: 251-66.
EUDRA document 3AB4a; http colon-slash-slash ec.europa.eu/enterprise/pharmaceuticals/eudralex/vol-3/pdfs-en/3ab4aen.pdf
Evans L et al., J Immunol 1988, 140: 941-943.
Fang J et al., Nat. Biotechnol. 2005, 23: 584-90.
Fearon D and Carroll M, Ann Rev Immun. 2000; 18:393-422.
Fearon K et al., Eur J Immunol 2003, 33: 2114-2122.
Forthal D N et al., Transpl Infect Dis. 2001, 3 Suppl 2:31-4.
Furebring C et al., Mol. Immunol. 2002, 38: 833-40.
Gay, N J et al., Nat Rev Immunol. 2006, 9:693-698
Gilliland L K et al., Tissue Antigens. 1996, 47: 1-20.
Giudicelli, V. et al., Nucl. Acids Res. 2004, 32: W435-440.
Goodrum F D et al., PNAS. 2002, 99:16255-60.
Gosselin J et al., J. Immunol. 2005, 174:1587-93.
Greijer A et al., J Clin Microbiol. 1999, 37:179-88.
Grunberg J et al., Biotechniques. 2003, 34: 968-72.
Gursel I et al., J. Immunol. 2001, 167: 3324-8.
Gursel M et al., J Leukoc Biol. 2002, 71: 813-20.
Haan K et al., J. Virol. 2001, 75: 3016-20.
Haab B B, Mol Cell Proteomics. 2005, 4: 377-83.
Hale G et al., Q J Nucl Med Mol. Imaging. 2004, 48:258-66.
Hartmann G et al., J Immunol 2000; 164: 1617-1624.
Hartmann G and Krieg A, J. Immunol. 2000, 164: 944-53.
Hayashi E et al., J. Immunol. 2005, 174(11):6639-47.
He B et al., J. Immunol. 2004, 172: 3268-79.
Heinrichs A et al., J Immunol Methods. 1995, 178: 241-51.
Hemmi H et al., Nature. 2000; 408: 740-5.
Henault M et al., 2005 J Immunol Methods. 2005; 300: 93-9.
Hoet R et al., Nat Biotechnol 2005, 23:344-348.
Horenstein A L et al., J Immunol Methods. 2003, 275:99-112.
Humme S et al., PNAS. 2003, 100: 10989-94.
Hur D et al., Cell Prolif. 2005, 38: 35-45.
Huse K et al., J Biochem Biophys Methods. 2002, 51:217-31.
Hwang W and Foote J, Methods. 2005, 36:3-10.
Ifversen P et al., Hum Antibodies Hybridomas. 1993, 4: 113-123.
Imadome K et al., PNAS. 2003, 100: 7836-40.
James K and Bell G, J Immunol Methods. 1987, 100:5-40.
Jarrin A and Andrieux A, Methods Mol. Biol. 1999, 96:21-8.
Jensen L B et al., J Immunol Methods. 2004, 284: 45-54.
Jondal M and Klein G, J Exp Med 1973, 138: 1365-1378.
Jovelin F et al., Biotechniques. 1995, 19: 378-82.
Jung J et al., J Immunol 2002, 169: 2368-2373.
Kandimalla E R et al., PNAS. 2005, 102: 6925-30.
Keller M A and Stiehm E R, Clin Microbiol Rev. 2000, 13: 602-14.
Kellermann S and Green L, Curr Opin Biotechnol. 2002, 13: 593-7.
Kern F et al., Trends Immunol. 2005, 26: 477-84.
Kilger E et al., EMBO J. 1998, 17: 1700-9.
Kim S J et al., Mol. Cells. 2005, 20: 17-29.
Klinman D et al., PNAS 1996, 93: 2879-2883.
Klinman D, Nat Rev Immunol. 2004; 4: 249-58.
Kocher A A et al., J Heart Lung Transpl. 2003, 22:250-7.
Kohler G and Milstein C, Nature 1975, 256: 495-497.
Konishi K et al., J Gen Virol. 2001, 82: 1451-6.
Kretzmer G, Appl Microbiol Biotechnol. 2002, 59: 135-42.
Krieg A et al., Nature. 1995; 374: 546-9.
Krieg A, Annu Rev Immunol. 2002, 20: 709-60.
Kruger R M et al., J Heart Lung Transpl. 2003, 22:754-63.
Laffy E and Sodoyer R, Hum. Antibodies. 2005, 14: 33-55.
Lal S P et al., Drug Discov Today. 2002, 7(Suppl):S143-9.
Landolfo S et al., Pharmacol Ther. 2003, 98: 269-97.
Laquerre S et al., J. Virol. 1998, 72: 6119-30.
Laroche-Traineau J et al., Hum Antib Hybrid. 1994, 5 165-177.
Li H et al., Biochem Biophys Res Commun 1995, 207: 985-93.
Li J et al., Proc Natl Acad Sci USA. 2006, 103: 3557-62.
Lightwood D et al., J Immunol Methods. 2006, 316: 133-43.
Ling N, J Immunol Methods. 2000, 238: 3-15.
Lobo E et al., J Pharm Sci. 2004, 93: 2645-68.
Ma J K et al., Vaccine. 2005, 23: 1814-8.
Mancini G et al., Immunochemistry. 1965, 2: 235-254.
Mancini N et al., New Microbiol. 2004, 27: 315-28.
McHeyzer-Williams L and McHeyzer-Williams M, Annu Rev Immunol. 2005, 23: 487-513.
Mezzasoma L et al., Clin Chem. 2002; 48: 121-30.
Morgenthaler N et al., J. Clin Endocrinology. 1996, 81: 3155-3161.
Mulder A et al., Hum Immunol. 1993; 36: 186-92.
Murray A et al., J Chromatogr Sci. 2002, 40: 343-9.
Nemerow G et al., J Virol 1985, 55:347-351.
Nicholas J, Mol. Pathol. 2000, 53: 222-37.
Niedbala W and Kurpisz M, Immunol Lett. 1993, 35:93-100.
Niedbala W and Stott D, Hybridoma 1998; 17: 299-304.
Nisnevitch M and Firer M A, J Biochem Biophys Methods. 2001; 49: 467-80.
Nitschke L, Curr Opin Immunol. 2005, 17: 290-7.
Norderhaug L et al., J Immunol Methods. 1997, 204:77-87.
Oh H et al., Cell Prolif. 2003, 36: 191-97.
Ohlin M et al., J. Virol. 1993, 67: 703-10.
Olivo P, Clin Microbiol Rev. 1996, 9: 321-34.
Olsson L and Kaplan H, PNAS 1980, 77:5429-5431.
Park C H et al., J Cell Biochem. 2004, 91: 777-85.
Pavlou A and Belsey M, Eur J Pharm Biopharm. 2005; 59: 389-96.
Peng S, Curr Opin Immunol. 2005, 17: 230-6.
Posner M et al., J. Immunol. 1991; 146: 4325-4332.
Potera C, Genetic Eng News. 2005, 25, 10 (available at http colon-slash-slash www.trellisbio.com/article GEN 051505.pdf)
Poul M A et al., Immunotechnology. 1995, 1: 189-96.
Radons J et al., J Immunol Methods. 2005, 303: 135-41.
Raff H et al., J Exp Med. 1988, 168: 905-17.
Ranjan D et al., Cell Biochem Funct. 2006, 24: 147-152.
Reinhardt B et al., J Virol Methods. 2003, 109: 1-9.
Rickinson A, Philos Trans R Soc Lond B Biol Sci. 2001, 356: 595-604
Roque A C et al., Biotechnol Prog. 2004, 20: 639-5
Schlatter S et al., Biotechnol Prog. 2005, 21: 122-33.
Schlee M et al., J. Virol. 2004, 78: 3941-52.
Schmidt F, Appl Microbiol Biotechnol. 2004, 65: 363-72
Schneider P, Curr Opin Immunol. 2005, 17: 282-9.
Schoppel K et al., Virology. 1996, 216: 133-45.
Sen G et al., Cell Immunol. 2004; 232: 64-74.
Sorensen H and Mortensen K, J. Biotech. 2005, 115: 113-28.
Speck P et al., J Gen Virol. 1999, 80: 2193-203.
Steenbakkers P et al., Hum Antibod Hybrid. 1993, 4: 166-173.
Steenbakkers P et al., Mol Biol Rep. 1994, 19: 125-134.

Sugimoto M et al., Cancer Res. 2004, 64: 3361-4.
Sun L et al., J Immunol Methods. 2003, 282: 45-52.
Takeshita F et al., J. Immunol. 2001, 167: 3555-8.
Tangye S et al., J. Immunol. 2003, 170: 261-9.
Tanner J E and Menezes J, Blood. 1994, 84: 3956-64.
Thomas T M et al., Hybrid Hybridomics. 2003, 22: 47-53.
Thomsen M et al., Tissue Antigens. 2005, 66: 73-82.
Thorley-Lawson D A, Nat Rev Immunol. 2001, 1(1):75-82.
Torres M et al., J. Immunol. 2005, 174: 2132-42.
Traggiai E et al., Nat Med 2004, 10:871-875.
Tsuchiyama L et al., Hum Antibodies. 1997, 8:43-7.
Ulevitch R, Nat Rev Immun. 2004, 4: 512-520.
Venturi M et al., J Mol Biol 2002, 315:1-8
Verdoliva A et al., J Immunol Methods. 2002, 271: 77-8.
Viau M and Zouali M, Clin Immunol. 2005, 114: 17-26.
Wallis R et al., J Clin Invest 1989, 84: 214-219.
Wen et al., Eur J. Immunol. 1987, 17: 887-92.
Wendel-Hansen V et al., Leukemia. 1994, 8: 476-84.
Wroblewski J et al., J Immunol Meth. 2002, 264:19-28
Yamaguchi H et al., PNAS 1987, 84: 2416-2420.
Yoon S K et al., Biotechnol Prog. 2004, 20: 1683-8.

The invention claimed is:

1. A method for immortalizing a population of cells that secrete antibodies of one or more specific isotypes comprising the following steps in sequence:

Selecting the population of cells that expresses antibodies from one or more biological samples in an antigen-independent manner and on the basis of expression of at least a cell surface marker;

Stimulating said population of selected cells with at least a stimulating agent in cell culture conditions;

Eliminating said stimulating agent from the cell culture;

Selecting the population of stimulated cells that expresses antibodies of one or more isotypes from said cell culture;

Exposing said population of selected and stimulated cells to an immortalizing agent in cell culture conditions;

Eliminating said immortalizing agent from said cell culture;

Wherein the immortalizing agent is a viral immortalizing agent.

2. The method of claim 1, wherein said population of cells of step (a) are human B cells and the cell surface marker is CD22, CD19, or CD27.

3. The method of claim 1, wherein said stimulating agent is chosen from:
   A combination of a CpG-based oligonucleotide and a cytokine;
   A combination of an agonist of a cell membrane receptor of the TNF receptor family and a cytokine;
   And the viral immortalizing agent is Epstein-Barr virus.

4. The method of claim 1, wherein the population of cells of step d) expresses IgG antibodies.

5. The method of claim 1, further comprising isolating a cell culture that produces a monoclonal antibody that specifically binds to an antigen, the steps comprising:
   (a) dividing the population of cells in a cell culture, each cell culture containing at least 20 cells;
   (b) screening a supernatant of said cell culture for antigen-binding specificity and/or biological activity;
   (c) identifying the cell culture exhibiting said antigen specificity and/or biological activity as a cell culture of interest.

6. The method of claim 5, further comprising purifying the monoclonal antibody.

7. The method of claim 6, further comprising determining the amino acid sequence of the monoclonal antibody.

8. The method of claim 5, wherein said antigen-binding specificity and/or biological activity is directed to a human, mammalian, viral, bacterial, plant, parasite, organic, or inorganic antigen.

* * * * *

SEQUENCE LISTING

<160> NUMBER OF SEQ ID NOS: 11

<210> SEQ ID NO 1
<211> LENGTH: 24
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: CpG oligonucleotide

<400> SEQUENCE: 1
tcgtcgtttt gtcgttttgt cgtt                                          24

<210> SEQ ID NO 2
<211> LENGTH: 528
<212> TYPE: DNA
<213> ORGANISM: Homo sapiens

<400> SEQUENCE: 2
atggggtcaa ccgccatcct cgccctcctc ctggctgttc tccaaggagt ctgtgccgag      60
gtgcagctgg tgcagtctgg ggcagaggtg aaaaagcccg gggagtctct gaagatctcc     120
tgtaagggtt ctggatacac ctttgacagc tactggatcg gctgggtgcg ccagatgccc     180
gggaaaggcc tggagtggat ggggatcatc tatcctggtg actctgatac cagatacagc     240
ccatccttcc aaggccaggt caccatctca gccgacaagt ccatcagcac cgcctctttg     300
cagtggagca gcctgagggc ctcggacacc gccatgtatt actgtgcgag acatacatac     360
cccggaccga atagtggcta cgactacttt gagtactggg gccagggaac cctggtcacc     420
gtctcctcag cctccaccaa gggcccatcg gtcttccccc tggcaccctc ctccaagagc     480
acctctgggg gcacagcggc cctgggctgc ctggtcaagg actacttc                 528

<210> SEQ ID NO 3
<211> LENGTH: 176
<212> TYPE: PRT
<213> ORGANISM: Homo sapiens

<400> SEQUENCE: 3

Met Gly Ser Thr Ala Ile Leu Ala Leu Leu Leu Ala Val Leu Gln Gly
1               5                   10                  15

Val Cys Ala Glu Val Gln Leu Val Gln Ser Gly Ala Glu Val Lys Lys
            20                  25                  30

Pro Gly Glu Ser Leu Lys Ile Ser Cys Lys Gly Ser Gly Tyr Thr Phe
        35                  40                  45

Asp Ser Tyr Trp Ile Gly Trp Val Arg Gln Met Pro Gly Lys Gly Leu
    50                  55                  60

Glu Trp Met Gly Ile Ile Tyr Pro Gly Asp Ser Asp Thr Arg Tyr Ser

```
                65                  70                  75                  80
Pro Ser Phe Gln Gly Gln Val Thr Ile Ser Ala Asp Lys Ser Ile Ser
                    85                  90                  95

Thr Ala Ser Leu Gln Trp Ser Ser Leu Arg Ala Ser Asp Thr Ala Met
                100                 105                 110

Tyr Tyr Cys Ala Arg His Thr Tyr Pro Gly Pro Asn Ser Gly Tyr Asp
                115                 120                 125

Tyr Phe Glu Tyr Trp Gly Gln Gly Thr Leu Val Thr Val Ser Ser Ala
            130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

<210> SEQ ID NO 4
<211> LENGTH: 5
<212> TYPE: PRT
<213> ORGANISM: Homo sapiens

<400> SEQUENCE: 4

Ser Tyr Trp Ile Gly
1               5

<210> SEQ ID NO 5
<211> LENGTH: 17
<212> TYPE: PRT
<213> ORGANISM: Homo sapiens

<400> SEQUENCE: 5

Ile Ile Tyr Pro Gly Asp Ser Asp Thr Arg Tyr Ser Pro Ser Phe Gln
1               5                   10                  15

Gly

<210> SEQ ID NO 6
<211> LENGTH: 15
<212> TYPE: PRT
<213> ORGANISM: Homo sapiens

<400> SEQUENCE: 6

His Thr Tyr Pro Gly Pro Asn Ser Gly Tyr Asp Tyr Phe Glu Tyr
1               5                   10                  15

<210> SEQ ID NO 7
<211> LENGTH: 423
<212> TYPE: DNA
<213> ORGANISM: Homo sapiens

<400> SEQUENCE: 7
ttcctcctgc tactctggct cccagatacc accggagaaa ttgtgttgac acagtctcca     60
gccaccctgt ctttgtctcc aggagaaaga gtcaccctct cctgcagggc cagtcagagt    120
gtttacaact acttagcctg gtaccaacag aaacctggcc aggctcccag gctcctcatc    180
tatgatgcat ccaacagggc cactggcatc ccagccaggt tcagtggcag tgggtctggg    240
acagacttca ctctcaccat cagcagccta gagcctgaag attttgcagt ttattactgt    300
cagctgcgtc agggacgttc ggccaaggga ccaaggtgg agatcaaacg aactgtggct    360
gcaccatctg tcttcatctt cccgccatct gatgagcagt tgaaatctgg aactgcctct    420
gtt                                                                  423
```

```
<210> SEQ ID NO 8
<211> LENGTH: 141
<212> TYPE: PRT
<213> ORGANISM: Homo sapiens

<400> SEQUENCE: 8

Phe Leu Leu Leu Leu Trp Leu Pro Asp Thr Thr Gly Glu Ile Val Leu
1               5                   10                  15

Thr Gln Ser Pro Ala Thr Leu Ser Leu Ser Pro Gly Glu Arg Val Thr
            20                  25                  30

Leu Ser Cys Arg Ala Ser Gln Ser Val Tyr Asn Tyr Leu Ala Trp Tyr
        35                  40                  45

Gln Gln Lys Pro Gly Gln Ala Pro Arg Leu Leu Ile Tyr Asp Ala Ser
    50                  55                  60

Asn Arg Ala Thr Gly Ile Pro Ala Arg Phe Ser Gly Ser Gly Ser Gly
65                  70                  75                  80

Thr Asp Phe Thr Leu Thr Ile Ser Ser Leu Glu Pro Glu Asp Phe Ala
                85                  90                  95

Val Tyr Tyr Cys Gln Leu Arg Arg Gly Thr Phe Gly Gln Gly Thr Lys
            100                 105                 110

Val Glu Ile Lys Arg Thr Val Ala Ala Pro Ser Val Phe Ile Phe Pro
        115                 120                 125

Pro Ser Asp Glu Gln Leu Lys Ser Gly Thr Ala Ser Val
    130                 135                 140

<210> SEQ ID NO 9
<211> LENGTH: 11
<212> TYPE: PRT
<213> ORGANISM: Homo sapiens

<400> SEQUENCE: 9

Arg Ala Ser Gln Ser Val Tyr Asn Tyr Leu Ala
1               5                   10

<210> SEQ ID NO 10
<211> LENGTH: 7
<212> TYPE: PRT
<213> ORGANISM: Homo sapiens

<400> SEQUENCE: 10

Asp Ala Ser Asn Arg Ala Thr
1               5

<210> SEQ ID NO 11
<211> LENGTH: 6
<212> TYPE: PRT
<213> ORGANISM: Homo sapiens

<400> SEQUENCE: 11

Gln Leu Arg Arg Gly Thr
1               5
```